(12) United States Patent
Hartwig et al.

(10) Patent No.: US 6,562,989 B2
(45) Date of Patent: May 13, 2003

(54) CATALYST FOR AROMATIC C—O, C—N, AND C—C BOND FORMATION

(75) Inventors: John F. Hartwig, Durham, CT (US); Quinetta Shelby, Chicago, IL (US); Noriyasu Kataoka, New Haven, CT (US)

(73) Assignee: Yale University, New Haven, CT (US)

( * ) Notice: Subject to any disclaimer, the term of this patent is extended or adjusted under 35 U.S.C. 154(b) by 57 days.

(21) Appl. No.: 09/922,525

(22) Filed: Aug. 3, 2001

(65) Prior Publication Data

US 2003/0008768 A1 Jan. 9, 2003

Related U.S. Application Data

(60) Provisional application No. 60/223,507, filed on Aug. 7, 2000.

(51) Int. Cl.$^7$ .......................... C07F 17/00; C07F 15/02; B01J 31/00; C07C 261/00; C07C 271/00

(52) U.S. Cl. .......................... 556/21; 544/178; 548/490; 549/462; 556/28; 560/24; 502/154; 502/155

(58) Field of Search ..................... 556/21, 28; 544/178; 548/490; 549/462; 502/154, 155; 560/24

(56) References Cited

U.S. PATENT DOCUMENTS

| | | | |
|---|---|---|---|
| 5,795,985 A | 8/1998 | Husler et al. | 544/106 |
| 5,847,166 A | 12/1998 | Buchwald et al. | 549/355 |
| 6,133,464 A | 10/2000 | Pugin et al. | 556/14 |
| 6,166,226 A | 12/2000 | Buchwald et al. | 549/355 |
| 6,169,192 B1 | 1/2001 | Pugin et al. | 556/11 |
| 6,191,284 B1 | 2/2001 | Knoched et al. | 548/402 |

OTHER PUBLICATIONS

"Organic Chemistry, Reaction Between Isoprene and Aniline On Complex", Petrushkina et al., A.N. Nosmeyanov Institute of Organoelemental Compounds, Russian Academy of Sciences, No. 8, Aug. 1992, pp. 1794–1798.

Dzhemilev, U.M., et al., "The Reaction of Butadiene With Morpholine As Catalyzed By Nickel Complexes", Bulletin of the Academy of Sciences of the USSR Division of Chemical Science, vol. 25, No. 8, Aug. 1976, pp. 1691–1694.

Dzhemilev, U.M., et al., "Reaction of Secondary Amines With Cyclic 1,3–Dienes, Catalyzed By Nickel Complexes", Bulletin of the Academy of Sciences of the USSR Division of Chemical Science, vol. 25, No. 10, Oct. 1976, pp. 2190–2191.

Dzhemilev, U.M., et al., "Reaction Of Cycloaliphatic Secondary Amines With Butadiene Catalyzed By Nickel Catalysts", Bulletin of the Academy of Sciences of the USSR Division of Chemical Science, vol. 27, No. 5, Part 1, May 1978, pp. 923–927.

Dzhemilev, U.M., et al., "Synthesis Of Unsaturated Amines From Butadiene And Allylamines In Presence Of Palladium And Nickel Complexes", Bulletin of the Academy of Sciences of the USSR Division of Chemical Science, vol. 27, No. 6, Part 2, Jun. 1978, pp. 1230–1232.

Zakharkin, L.I., et al., "Telomerization Of Isoprene With Piperidine On Complex Palladium Catalysts", Bulletin of the Academy of Sciences of the USSR Division of Chemical Science, vol. 32, No. 4, Part 2, Apr. 1983, pp. 805–809.

Zakharkin, L.I., et al., "Telomerization Of Isoprene With N–Methylaniline On Complex Palladium Catalysts", Bulletin of the Academy of Sciences of the USSR Division of Chemical Science, vol. 35, No. 6, Part 1, Jun. 1986, pp. 1219–1222.

Dzhemilev, U.M., et al., "Amination Of Unsaturated Hydrocarbons By Secondary Amines, Catalyzed By Complexes Of Nickel And Palladium", Bashkir Branch, Academy of Sciences of the USSR, vol. 15, No. 6, pp. 1164–1169, Jun. 1979, pp. 1041–1045.

Zakharkin, M.I., et al., "Telomerization Of Isoprene With Phthalimide At Complex Palladium Catalysts", A.N. Nesmeyanov Institute of Heteroorganic Compounds Academy of Sciences of the USSR, Moscow, vol. 23, No. 8, Aug. 1987, pp. 1654–1656.

Primary Examiner—Porfirio Nazario-Gonzalez
(74) Attorney, Agent, or Firm—Todd E. Garabedian; Wiggin & Dana LLP

(57) ABSTRACT

The present invention is directed to a transition metal catalyst, comprising a Group 8 metal and a ligand having the structure

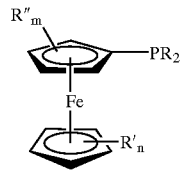

wherein R, R' and R" are organic groups having 1–15 carbon atoms, n=1–5, and m=0–4. The present invention is also directed to a method of forming a compound having an aromatic or vinylic carbon-oxygen, carbon-nitrogen, or carbon-carbon bond using the above catalyst. The catalyst and the method of using the catalyst are advantageous in preparation of compounds under mild conditions of approximately room temperature and pressure.

38 Claims, No Drawings

CATALYST FOR AROMATIC C—O, C—N, AND C—C BOND FORMATION

This application claims the benefit of U.S Provisional Application Ser. No. 60/223,507 filed Aug. 7, 2000.

STATEMENT OF GOVERNMENT SUPPORT

This invention was made in part with government support under grant number R29-GM55382 from the National Institutes of Health. The government has certain rights in this invention.

BACKGROUND OF THE INVENTION

1. Field of the Invention

The present invention relates to transition metal catalysts for aromatic or vinylic C—O, C—N, and C—C bond formation, and more particularly to transition metal catalysts for aromatic or vinylic C—O, C—N, and C—C bond formation that include ferrocenyl ligands and a transition metal atom such as platinum, palladium, or nickel. The present invention also relates to method of forming compounds containing aromatic C—O, C—N, and C—C bonds using the transition metal catalysts.

2. Brief Description of the Related Art

Mild, aromatic or vinylic substitution to form C—O, C—N, and C—C bonds is a difficult transformation. For reactions of unactivated aryl halides, direct, uncatalyzed substitutions and copper-mediated couplings typically require temperatures of 100° C. or greater (Bacon, R. G. R.; Rennison, S. C. *J. Chem. Soc.* (C) 1969, 312–315; Marcoux, J. F.; Doye, S.; Buchwald, S. L. *J. Amn. Chem. Soc.* 1997, 119, 10539–10540; Kalinin, A. V.; Bower, J. F.; Riebel, P.; Snieckus, V. *J. Org. Chem.* 1999, 64, 2986–2987).

Alternative approaches have suffered similar drawbacks and disadvantages. For example, diazotization and displacement with oxygen or nitrogen nucleophiles is generally limited in scope and uses stoichiometric amounts of copper in its mildest form (March, J. In *Advanced Organic Chemistry* John Wiley and Sons: New York, 1985; pp 601). Recently, palladium catalysts for the formation of diaryl and alkyl aryl ethers from unactivated aryl halides have been shown to be useful in these reactions (Mann, G.; Incarvito, C.; Rheingold, A. L.; Hartwig, J. F. *J. Am. Chem. Soc.* 1999, 121, 3224–3225). However, this system for C—O bond-formation as well as similar systems (Aranyos, A.; Old, D. W.; Kiyomori, A.; Wolfe, J. P.; Sadighi, J. P.; Buchwald, S. L. *J. Am. Chem. Soc.* 1999, 121, 4369–4378) required temperatures similar to those for copper-mediated processes (Bacon, R. G. R.; Rennison, S. C. *J. Chem. Soc.* (C) 1969, 312–315; Marcoux, J. F.; Doye,. S.; Buchwald, S. L. *J. Am. Chem. Soc.* 1997, 119, 10539–10540; Kalinin, A. V.; Bower, J. F.; Riebel, P.; Snieckus, V. *J. Org. Chem.* 1999, 64, 2986–2987; Boger, D. L.; Yohannes, D. *J. Org. Chem.* 1991, 56, 1763; Fagan, P. J.; Hauptman, E.; Shapiro, R.; Casalnuovo, A. *J. Am. Chem. Soc.* 2000, 122, 5043–5051). In addition, several catalysts have been shown to induce aromatic C—N bond-formation from aryl halides and sulfonates. Yet, the termperatures, for general reactions remain high in many cases, and the selectivities for formation of the desired aniline derivative instead of the undesired arene or diarylamine are often lower than optimal for synthetic applications.(Wolfe, J. P.; Buchwald, S. L. *J. Org. Chem.* 2000, 65, 1444; Wolfe, J. P.; Buchwald, S. L. *J. Org. Chem.* 2000, 65, 1158; Huang, J.; Grassa, G.; Nolan, S. P. *Org. Lett.* 1999, 1, 1307; Hartwig, J. F.; Kawatsura, M.; Hauck, S. I.; Shaughnessy, K. H.; Alcazar-Roman, L. M. *J. Org. Chem.* 1999, 64, 5575; Stauffer, S. I.; Hauck, S. I.; Lee, S.; Stambuli, J.; Hartwig, J. F. *Org. Lett.* 2000, 2, 1423) Finally, catalysts have been developed for aromatic or vinylic C—C bond formation, but again the conditions for these reactions are often harsh.(Suzuki, A. *J. Organomet. Chem.* 1999, 576, 147; Buchwals, S. L.; Fox, J. M. *The Strem Chemiker,* 2000, 18, 1; Zhang, C; Huang, J.; Trudell, M. L.; Nolan, S. P. *J. Org. Chem.* 1999, 64, 3804; Beletskaya, I. P. Cheprakov, A. V. *Chem. Rev.* 2000, 100, 3009; Littke, A. F.; Fu, G. C. *J. Org. Chem.* 1999, 64, 10; Shaughnessy, K. H.; Hartwig, J. F. *J. Am. Chem. Soc.* 1999, 121, 2123) In particular for each of these three classes of reactions, the bond-forming processes are especially difficult to conduct under mild conditions with high selectivity when using chloroarenes.

Unfortunately, reaction conditions such as those described above are quite harsh and require special equipment and techniques to accomplish even small scale syntheses. In addition, larger scale reactions of these reactions, such as those used in large-scale pharmaceutical manufacturing, are generally impractical and expensive due to these extreme reaction conditions. What is needed in the art is a catalytic method of aromatic or vinylic carbon-oxygen, carbon-nitrogen, and carbon-carbon bond formation that occurs under mild conditions (e.g., room temperature and atmospheric pressure) and that is easily scalable for large-scale synthesis, for example, in the pharmaceutical industry. The present invention is believed to be an answer to that need.

SUMMARY OF THE INVENTION

In one aspect, the present invention is directed to a transition metal catalyst, comprising a Group 8 metal and a ligand having the structure

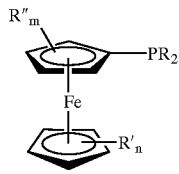

wherein R, R' and R" are organic groups having 1–15 carbon atoms, n=1–5, and m=0–4.

In another aspect, the present invention is directed to a method of forming a compound having an aromatic or vinylic carbon-oxygen, carbon-nitrogen, or carbon-carbon bond, comprising the step of reacting a first substrate and a second substrate in the presence of a transition metal catalyst, wherein the first substrate comprises an aryl halide reagent or an aryl sufonate reagent, and the second substrate comprises an alcohol reagent, an alkoxide reagent, a silanol reagent, a siloxide reagent, an amine reagent, an organoboron reagent, an organozinc reagent, an organomagnesium reagent, a malonate reagent, a cyanoacetate reagent, or an olefinic reagent, and wherein the transition metal catalyst comprises a Group 8 metal and a ligand having the structure

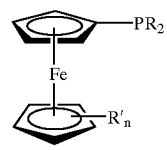

wherein R and R' are organic groups having 1–15 carbon atoms, and n=1–5; under reaction conditions effective to form the compound, wherein the compound has an aromatic carbon-oxygen, carbon-nitrogen, or carbon-carbon bond between the first substrate and the second substrate.

In yet another aspect, the present invention is directed to a method of forming a compound having an aromatic carbon-oxygen, carbon-nitrogen, or carbon-carbon bond, comprising the step of reacting a first substrate and a second substrate in the presence of a transition metal catalyst, wherein the first substrate comprises a selected aryl halide reagent or an aryl sufonate reagent and the second substrate is selected from the group consisting of NaO—$C_6H_4$—OMe, NaO-tBu, NaO—Si-(tBu)$Me_2$, HO—$C_6H_4$—OMe, HO-tBu, HO—Si-(tBu)$Me_2$, primary amines, secondary amines, alkyl amines, benzylic amines, aryl amines including morpholine, dibutylamine, aniline, n-butylamine, n-hexylamine, methylaniline, aminotoluene; organoboron reagents, organozinc reagents, organomagnesium reagents, indoles, ethyl cyanoacetate, diethyl malonate, methyl acrylate, and combinations thereof, and wherein the transition metal catalyst comprises a Group 8 metal selected from the group consisting of palladium, platinum, and nickel, and a ligand having the structure

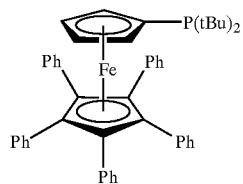

in a solvent selected from the group consisting of aromatic hydrocarbons, chlorinated aromatic hydrocarbons, ethers, water, aliphatic alcohols, and combinations thereof, under reaction conditions effective to form the compound, wherein the compound has an aromatic carbon-oxygen, carbon-nitrogen, or carbon-carbon bond between the first substrate and the second substrate.

These and other aspects will become apparent upon reading the following detailed description of the invention.

DETAILED DESCRIPTION OF THE INVENTION

It now has been surprisingly found, in accordance with the present invention, that a solution is provided to the problem of providing a general and efficient catalytic method of aromatic or vinylic carbon-oxygen, carbon-nitrogen, and carbon-carbon bond formation between two substrates that occurs under mild conditions (e.g., room temperature and atmospheric pressure). The present inventors have solved this problem by utilizing a catalyst that includes a transition metal catalyst comprising a Group 8 metal and a substituted ferrocenylphosphineligand. The catalyst is useful in a general and efficient process of formation of reaction products containing an aromatic carbon-oxygen, carbon-carbon, or carbon-nitrogen bond. Production of carbon-oxygen, carbon-carbon, or carbon-nitrogen bonds between substrates under mild conditions is particularly advantageous in the pharmaceutical industry where active starting substrates can be rapidly degraded by harsh chemical coupling conditions. The aromatic carbon-oxygen, carbon-carbon, or carbon-nitrogen bonds are formed under mild conditions and in the presence of the catalyst using a variety of starting substrates, most notably aryl halide reagents, aryl sulfonate reagents, alkoxide reagents, siloxide reagents, alcohol reagents, silanol reagents, amine reagents, organoboron reagents, organomagnesium reagents, organozinc reagents, malonate reagents, cyanoacetate reagents, and olefinic reagents. In addition to forming an aromatic carbon-oxygen bond between two distinct substrates, the catalyst and method of the present invention is also useful in intramolecular reactions, such as intramolecular etherification, amination, or vinylation where a single compound comprises each of the two substrates.

As defined herein, the term "substrate" includes distinct compounds possessing the above reactive groups (for example, aryl halides, aryl sulfonates, alkoxides, alcohols, siloxides, silanols, amines or related compounds with an N—H bond, organoborons, organomagnesiums, organozincs, malonates, cyanoesters, and olefinic compounds) as well as a single compound that includes reactive groups such as aryl halides, aryl sulfonates, alkoxides, alcohols, siloxides, silandls, amines or related compounds with an N—H bond, organoboron, organomagnesium, organozinc, malonate, cyanoester, and olefinic groups, such that an intramolecular reaction can take place in the presence of the catalyst of the present invention. As defined herein, the term "aromatic" refers to a compound whose molecules have the ring structure characteristic of benzene, naphthalene, phenanthroline, anthracene, related heterocycles such as pyridines, pyrimidines, thiophenes, furans, pyrroles, and the like. The phrase "aromatic carbon-oxygen, carbon-nitrogen, or carbon-carbon bond" refers to a covalent bond between a carbon atom of an aromatic or heteroaromatic ring of a first substrate, and an oxygen, nitrogen, or carbon atom of a second substrate. The terms "amine" and "amine reagent" are broadly defined herein to encompass primary amines, secondary amines, alkyl amines, benzylic amines, aryl amines, as well as related compounds with N—H bonds, including carbamates and cyclic or heterocyclic amine compounds.

As indicated above, the transition metal catalyst of the present invention includes a transition metal atom complexed with a ferrocenyl ligand. In one embodiment, the ferrocenyl ligand portion of the catalyst is represented by the formula:

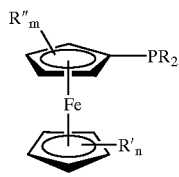

wherein R, R', and R" are organic groups having 1–15 carbon atoms, n=1–5, and m=0–4. Within the ferrocenyl ligand, R can be any organic group possessing 1–15 carbon atoms, preferably 2–8 carbon atoms, and more preferably 2–5 carbon atoms. In one preferred embodiment, R possesses 4 carbon atoms, and is a tertiary butyl group (tBu). R' can also be any organic group possessing 1–15 carbon atoms, with or without additional substitutents such as halides, and the like. More preferably, R' possesses 1–10 carbon atoms, and most preferably 2–8 carbon atoms. In one embodiment, R' may be phenyl, MeO—$C_6H_4$, $F_3C$—$C_6H_4$, methyl, or o-tolyl. In addition, the number of R' groups preferably ranges from 1–5, most preferably either 4 or 5. R" can also be any organic group possessing 1–15 carbon atoms. Preferable substituents for R" include methyl, ethyl, propyl, aminoalkyl, 1-dialkylaminoethyl, 1-alkoxyethyl, phenyl, methoxyphenyl, halophenyl, naphthyl, and the like. The number of R" groups ranges from 0–4.

In one preferred embodiment, the transition metal catalyst is a palladium complex with a ferrocenyl ligand having the formula:

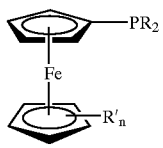

wherein R' is phenyl, MeO—C$_6$H$_4$, F$_3$C—C$_6$H$_4$, methyl, or o-tolyl, R is tert-butyl, and n is 4 or 5.

In one particularly preferred embodiment, the transition metal catalyst is a palladium complex with a ferrocenyl ligand having the formula:

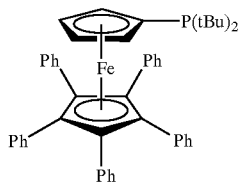

The transition metal atom or ion is required to be a Group 8 transition metal, that is, a metal selected from iron, cobalt, nickel, ruthenium, rhodium, palladium, osmium, iridium, and platinum. More preferably, the Group 8 metal is palladium, platinum, or nickel, and most preferably, palladium. The Group 8 metal may exist in any oxidation state ranging from the zero-valent state to any higher variance available to the metal. The catalyst may be formed from a mixture of P(C$_5$H$_4$FeC$_5$H$_5$)(t-Bu)$_2$, Pd(OAc)$_2$, NaO-t-Bu and PhCl according to Equation 1.

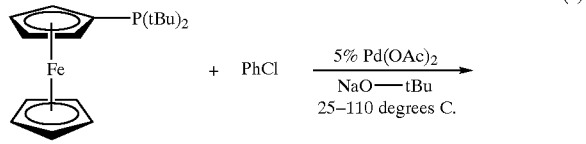

(1)

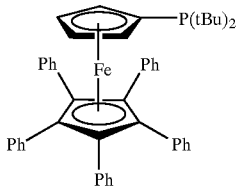

In the presence of a Group 8 metal, such as iron, cobalt, nickel, ruthenium, rhodium, palladium, osmium, iridium, or platinum, the ferrocenyl ligand is formed into an active catalyst that is useful in catalyzing reactions that form carbon-oxygen, carbon-nitrogen, or carbon-carbon bonds between the substrates.

The transition metal catalyst may be synthesized first and thereafter employed in the reaction process. Alternatively, the catalyst can be prepared in situ in the reaction mixture. If the latter mixture is employed, then a Group 8 catalyst precursor compound and the ferrocenyl ligand are independently added to the reaction mixture wherein formation of the transition metal catalyst occurs in situ. Suitable precursor compounds include alkene and diene complexes of the Group 8 metals, preferably, di(benzylidene)acetone (dba) complexes of the Group 8 metals, as well as, monodentate phosphine complexes of the Group 8 metals, and Group 8 carboxylates or halides. In the presence of the ferrocenyl ligand, in situ formation of the transition metal catalyst occurs. Non-limiting examples of suitable precursor compounds include [bis-di(benzylidene)acetone]palladium (0) as shown in Eq. 1, tetrakis-(triphenylphosphine)-palladium (0), tris-[di(benzylidene)acetone]palladium (0), tris-[di(benzylidene)acetone]-dipalladium (0), palladium acetate, palladium chloride, and the analogous complexes of iron, cobalt, nickel, ruthenium, rhodium, osmium, iridium, and platinum.

Any of the aforementioned catalyst precursors may include a solvent of crystallization. Group 8 metals supported on carbon, preferably, palladium on carbon, can also be suitably employed as a precursor compound. Preferably, the catalyst precursor compound is bis-[di(benzylidene)acetone]palladium(0).

As indicated above, the present invention is also directed to a method of forming a compound having an aromatic carbon-oxygen, carbon-carbon, or carbon-nitrogen bond, comprising the step of reacting a first substrate and a second substrate in the presence of the transition metal catalyst described above. Each of these steps and components are described in more detail below.

Aryl halides that are useful as reagents include any compounds in which a halide atom is covalently bound to an aryl ring structure, such as a benzene ring or a heteroaromatic ring. Nonlimiting examples of suitable aryl halide reagents include bromobenzene, chlorobenzene, methoxy bromo- or chlorobenzene, bromo- or chloro toluene, bromo- or chloro benzophenone, bromo- or chloro nitrobenzene, halopyridines, halopyrazines, halopyrimidines, and the like. The structures of several examples of useful aryl halides are shown in Table A below:

TABLE A

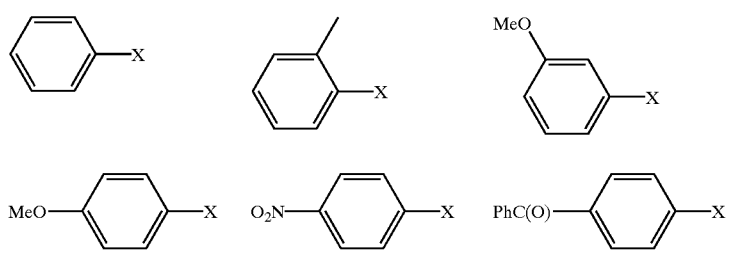

TABLE A-continued

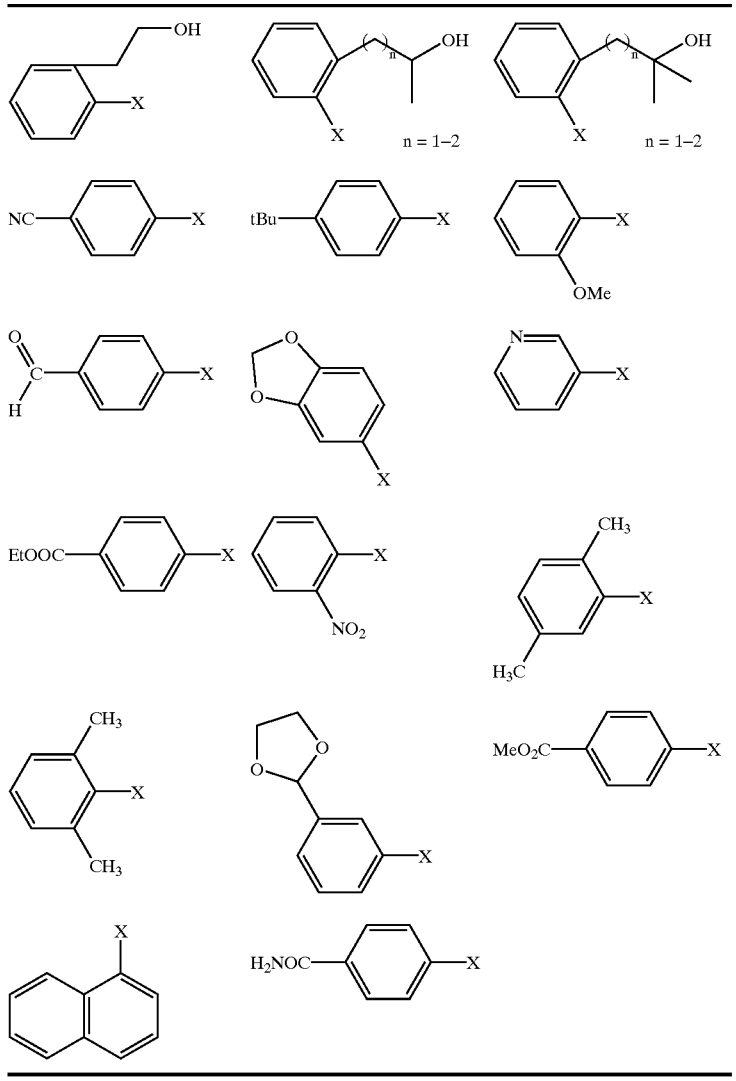

In each of the structures shown in Table A, X may be any halogen, for example, bromine, chlorine, flourine, or iodine. Additionally, X may be a sulfonate group, such that aryl sulfonates may also be used in the method of the present invention.

As indicated above, the second substrate may be an alcohol reagent, an alkoxide reagent, a silanol reagent, a siloxide reagent, an amine reagent, an organoboron reagent, an organozinc reagent, an organomagnesium reagent such as a Grignard reagent, a malonate reagent, a cyanoacetate reagent, an olefinic reagent, or combinations of these. Non-limiting examples of useful alkoxide reagents include NaO—$C_6H_4$—OMe and NaO-tBu. Nonlimiting examples of useful siloxide reagents include NaO—Si-(tBu)Me$_2$. Non-limiting examples of amine reagents include compounds with N—H bonds, including carbamates and cyclic or heterocyclic amine compounds such as pyrrole, indole, and the like. Examples of amine and related N—H reagents that are useful in the method of the present invention include, but are not limited to, morpholine, dibutylamine, aniline, n-butylamine, n-hexylamine, methylaniline, aminotoluene, t-butylcarbamate, indole, benzophenone hydrazone and benzophenone imine.

Useful organoboron reagents include arylboronic acids, such as o-tolylboronic acid, phenylboronic acid, p-trifluoromethylphenylboronic acid, p-methoxyphenylboronic acid, o-methoxyphenylboronic acid, 4-chlorophenylboronic acid, 4-formylphenylboronic acid, 2-methylphenylboronic acid, 4-methoxyphenylboronic acid, 1-naphthylboronic acid, and the like. Useful organozinc reagents include n-butylzinc chloride, secbutylzinc chloride and phenylzinc chloride. Useful organomagnesium reagents include butylmagnesium bromide and phenylmagnesium chloride. Useful olefinic reagents include vinylarenes such as styrene and acrylic acid derivatives such as n-butyl acrylate and methyl acrylate. All of these reagents may be used as the limiting substrate or in excess quantities and are preferably used in quantities of 0.2–5 equivalents relative to the aromatic halide or sulfonate.

The method of the present invention optionally takes place in the presence of a base. Any base may be used so long as the process of the invention proceeds to the product. Non-limiting examples of suitable bases include alkali metal hydroxides, such as sodium and potassium hydroxides; alkali metal alkoxides, such as sodium t-butoxide; metal carbonates, such as potassium carbonate, cesium carbonate, and magnesium carbonate; phosphates such as trisodium or tripotassium phosphate; alkali metal aryl oxides, such as potassium phenoxide; alkali metal amides, such as lithium amide; tertiary amines, such as triethylamine and tributylamine; (hydrocarbyl)ammonium hydroxides, such as benzyltrimethylammonium hydroxide and tetraethylammonium hydroxide; and diaza organic bases, such as 1,8-diazabicyclo [5.4.0]-undec-7-ene and 1,8-diazabicyclo-[2.2.2.]-octane, and organic or alkali metal fluorides such as tetrabutylamonium fluoride or potassium fluoride. Preferably, the base is an alkali hydroxide, alkali alkoxide, alkali carbonate, alkali phosphate or alkali fluoride, more preferably, an alkali alkoxide, and most preferably, an alkali metal $C_{1-10}$ alkoxide.

The quantity of base which may be used can be any quantity which allows for the formation of the product. Preferably, the molar ratio of base to arylating compound ranges from about 1:1 to about 5:1, and more preferably between about 1:1 and 3:1.

As an alternative embodiment of this invention, the catalyst may be anchored or supported on a catalyst support, including a refractory oxide, such as silica, alumina, titania, or magnesia; or an aluminosilicate clay, or molecular sieve or zeolite; or an organic polymeric resin.

The quantity of transition metal catalyst which is employed in the method of this invention is any quantity which promotes the formation of the desired product. Generally, the quantity is a catalytic amount, which means that the catalyst is used in an amount which is less than stoichiometric relative to either of the substrates. Typically, the transition metal catalyst ranges from about 0.01 to about 20 mole percent, based on the number of moles of either the first substrate or the second substrate used in the reaction. Preferably, the quantity of transition metal catalyst ranges from about 0.01 to about 2 mole percent, and more preferably from about 0.1 to about 2 mole percent, based on the moles of either substrate. In addition, the ratio of ferrocenyl ligand to Group 8 metal is preferably in the range from about 3:1 to about 0.25:1, more preferably from about 0.5:1 to about 2:1, and most preferably from about 0.8:1 to about 3:1.

The method described herein may be conducted in any conventional reactor designed for catalytic processes. Continuous, semi-continuous, and batch reactors can be employed. If the catalyst is substantially dissolved in the reaction mixture as in homogeneous processes, then batch reactors, including stirred tank and pressurized autoclaves, can be employed. If the catalyst is anchored to a support and is substantially in a heterogeneous phase, then fixed-bed and fluidized bed reactors can be used. In the typical practice of this invention, the substrates, the catalyst, and any optional base are mixed in batch, optionally with a solvent, and the resulting mixture is maintained at a temperature and pressure effective to prepare the aromatic product containing a C—O, C—C, or C—N covalent bond.

Any solvent can be used in the process of the invention provided that it does not interfere with the formation of the product. Both aprotic and protic solvents and combinations thereof are acceptable. Suitable aprotic solvents include, but are not limited to, aromatic hydrocarbons, such as toluene and xylene, chlorinated aromatic hydrocarbons, such as dichlorobenzene, and ethers, such as dimethoxyethane, tetrahydrofuran or dioxane. Suitable protic solvents include, but are not limited to, water and aliphatic alcohols, such as ethanol, isopropanol, and cyclohexonol, as well as glycols and other polyols. The amount of solvent which is employed may be any amount, preferably an amount sufficient to solubilize, at least in part, the reactants and base. A suitable quantity of solvent typically ranges from about 1 to about 100 grams solvent per gram reactants. Other quantities of solvent may also be suitable, as determined by the specific process conditions and by the skilled artisan.

Generally, the reagents may be mixed together or added to a solvent in any order. Air is preferably removed from the reaction vessel during the course of the reaction, however this step is not always necessary. If it is desirable or necessary to remove air, the solvent and reaction mixture can be sparged with a non-reactive gas, such as nitrogen, helium, or argon, or the reaction may be conducted under anaerobic conditions. The process conditions can be any operable conditions which yield the desired product. Beneficially, the reaction conditions for this process are mild. For example, a preferred temperature for the process of the present invention ranges from about ambient, taken as about 22° C., to about 150° C., and preferably, from about 25° C. to about 70° C. The process may be run at subatmospheric pressures if necessary, but typically proceeds sufficiently well at about atmospheric pressure. The process is generally run for a time sufficient to convert as much of the substrates to product as possible. Typical reaction times range from about 30 minutes to about 24 hours, but longer times may be used if necessary.

The product can be recovered by conventional methods known to those skilled in the art, including, for example, distillation, crystallization, sublimation, and gel chromatography. The yield of product will vary depending upon the specific catalyst, reagents, and process conditions used. For the purposes of this invention, "yield" is defined as the mole percentage of product recovered, based on the number of moles of starting reactants employed. Typically, the yield of product is greater than about 25 mole percent. Preferably, the yield of product is greater than about 60 mole percent, and more preferably, greater than about 75 mole percent.

EXAMPLES

The following examples are intended to illustrate, but in no way limit the scope of the present invention. All parts and percentages are by weight and all temperatures are in degrees Celsius unless explicitly stated otherwise.

General Methods

Reactions were loaded in a drybox and were conducted using 4 mL vials that were sealed with a cap containing a PTFE septum. $^1$H and $^{13}$C-NMR spectra were recorded on a Bruker DPX 400 MHz spectrometer or a General Electric QE 300 MHz spectrometer with tetramethylsilane or residual protiated solvent used as a reference. Toluene was distilled from sodium and benzophenone and stored in the drybox. Elemental analyses were performed by Atlantic Microlabs Inc., Norcross, Ga. Chromatographic purifications were performed by flash chromatography using silica gel (200–400 mesh) from Naeland International Corporation. Yields refer to isolated yields of compounds of greater than 95% purity as determined by capillary gas chromatography (GC). Yields reported are an average of two or more runs. GC analyses were conducted on a HP-5890 series II with HP3395 as intelligent recorder. GC/MS spectra were recorded on an HP-5890 instrument equipped with an HP5971A Mass Spectral Analyzer. Both GC and GC/MS analyses used an HP-1 methyl silicone column. Reagents were purchased from commercial suppliers, or prepared by standard procedures known in the art. 2-(2-Bromophenyl) methyl acetate, sodium tert-butyl-dimethylsiloxide, and {Pd $(P(C_5H_4FeC_5H_5)(t-Bu)_2)(C_6H_4-2-Me)(OC_6H_4-4-OMe)\}_2$ (Entry 1 in Table 1) were prepared by literature procedures (Palucki, M.; Wolfe, J. P.; Buchwald, S. L. *J. Am. Chem. Soc.* 1996, 118, 10333–10334; Mann, G.; Hartwig, J. F. *J. Org. Chem.* 1997, 62, 5413–5418; Mann, G.; Incarvito, C.; Rheingold, A. L.; Hartwig, J. F. *J. Am. Chem. Soc.* 1999, 121, 3224–3225).

A. Ligand Preparation

Example 1

Synthesis of $P(C_5H_4FeC_5H_5)(t-Bu)_2$

To a solution of $CP_2Fe$ (10.00 g, 53.80 mmol) in THF (25 mL) at 0° C. was added t-BuLi (31.60 mL, 53.80 mmol) over 5 min. The solution was stirred for 20 min, after which time the solvent was removed under vacuum. The residue was redissolved in a mixture of pentane (100 mL) and THF (5mL) and ClP(t-Bu)$_2$ (5.330 g, 29.50 mmol) was added. The mixture was stirred for 3 h, after which time degassed MeOH (1 mL) was added. The solvents were then removed in vacuo. The product was purified by filtration through a plug of silica gel under nitrogen. Unreacted ferrocene was eluted all at once with pentane, and the phosphine was then eluted all at once with diethyl ether. Crystallization from pentane of the material obtained from silica gel yielded 7.58 g (78%) of product. $^1$H NMR (C$_6$D$_6$) δ 1.23 (d, 10.9 Hz, 18 H), 4.04 (s, 5H), 4.08 (m, 2H), 4.17 (m, 2H), 4.17 (m, 2H); $^{13}$C{$^1$H} NMR (C$_6$D$_6$): δ 31.05 (d, 13.9 Hz), 32.78 (d, 22.9 Hz), 69.20 (d, 2.7 Hz), 69.79, 73.23 (d, 12.3 Hz), 79.10 (d, 31.2 Hz); $^{31}$P{$^1$H} NMR (C$_6$D$_6$): δ 27.54 (s); Anal. Calc'd. for C$_{18}$H$_{27}$FeP: H: 8.24, C: 65.47; Found: H: 8.34, C: 65.51.

Example 2

Synthesis of P(C$_5$H$_4$FeC$_5$Ph$_5$)(t-BU)$_2$

A mixture of P(C$_5$H$_4$FeC$_5$H$_5$)(t-BU)$_2$ (1.000 g, 3.030 mmol), Pd(OAc)$_2$ (0.035 g, 0.156 mmol), and NaO-t-Bu (2.93 g, 30.5 mmol) was dissolved in PhCl (34.10 g, 303.0 mmol) and heated to 110° C. for 18 h. The solution was filtered through Celite, and PhCl was removed in vacuo. Silica gel chromatography eluting with pentane/Et$_2$O (80/1) gave 1.466 g (68%) of P(C$_5$H$_4$FeC$_5$Ph$_5$)(t-Bu)$_2$ as a pink/red solid. $^1$H (C$_6$D$_6$): δ 1.07 (d, 11.0 Hz, 18H, CMe$_3$), 4.42 (t, 1.7 Hz, 2H, C$_5$H$_4$), 4.67 (d, 1.0 Hz, 2H, C$_5$H$_4$), 6.95–6.97 (m, 15H, m,p-C$_6$H$_5$), 7.44–7.48 (m, 10H, o-C$_6$H$_5$). $^{13}$C{$^1$H} NMR (C$_6$C$_6$): δ 31.31 (d, 13.8 Hz, CMe$_3$), 33.31 (d, 24.8 Hz, CMe$_3$), 76.41 (d, 2.6 Hz, C$_5$H$_4$), 78.58 (d, 11.4 Hz, C$_5$H$_4$), 85.49 (d, 41.6 Hz, ipso-C$_5$H$_4$), 88.38 (s, C$_5$Ph$_5$), 126.67 (s, C$_5$Ph$_5$), 127.47 (s, C$_5$Ph$_5$), 133.23 (s, C$_5$Ph$_5$), 136.32 (s, C$_5$Ph$_5$). $^{31}$P{$^1$H} NMR (C$_6$D$_6$): δ 25.49 (s). Anal. Calc'd. for C$_{48}$H$_{47}$FeP: C, 81.12; H, 6.67. Found: C, 81.41; H, 6.54.

Example 3

Synthesis of P(C$_5$H$_4$FeC$_5$HPh$_4$)(t-Bu)$_2$

A mixture of P(C$_5$H$_4$FeC$_5$H$_5$)(t-Bu)$_2$ (0.500 g, 1.500 mmol), Pd(OAc)$_2$ (0.0175 g, 0.078 mmol), and NaOC$_6$H$_4$-4-OCH$_3$ (2.230 g 15.30 mmol) was dissolved in PhCl (17.10 g, 152.0 mmol) and heated at 110° C. for 18 h. The solution was filtered through Celite, and PhCl was removed in vacuo. The solid materials were redissolved in THF, concentrated, and layered with pentane at −35° C. A bulk sample that was analytically pure was not available, but a sample of roughly 80% purity containing orange crystals of the tetraphenylferrocenyl phosphine was obtained (0.451 g, 47.4%). $^1$H (C$_6$D$_6$): δ 1.09 (d, 11.1 Hz, 18H, CMe$_3$), 4.01 (broad s, 2H, C$_5$H$_4$), 4.33 (t, 1.7 Hz, 2H, C$_5$H$_4$), 5.01 (s, 1H, C$_5$HPh$_4$), 6.93–7.14 (m, 12H, m,p-C$_5$HPh$_4$), 7.30 (dd, 7.2 Hz, 0.9 Hz, 4H, o-C$_5$HPh$_4$), 7.66 (dd, 7.7 Hz, 1.7 Hz, 4H, o'-C$_5$HPh$_4$). $^{13}$C{$^1$H} δ 31.00 (d, 13.6 Hz, CMe$_3$), 33.01 (d, 22.4 Hz, CMe$_3$), 76.51 (s, CHC$_4$Ph$_4$), 77.15 (s, C$_5$H$_4$), 78.31 (d, 9.7 Hz, C$_5$H$_4$), 81.86 (d, 33.6 Hz, ipso-C$_5$H$_4$), 87.50 (s, CHC$_4$Ph$_4$), 88.12 (s, CHC$_4$Ph$_4$), 126.70 (s, C$_5$HPh$_4$), 127.68 (s, C$_5$HPh$_4$), 127.90 (s, C$_5$HPh$_4$), 130.99 (s, C$_5$HPh$_4$), 131.05 (s, C$_5$HPh$_4$), 132.68 (s, C$_5$HPh$_4$), 136.66 (s, C$_5$HPh$_4$), 137.87 (s, C$_5$HPh$_4$). $^{31}$P{$^1$H} NMR (C$_6$D$_6$): δ 25.34 (s). HRMS: m/e Calc'd., 634.2452; Found, 634.2444.

Example 4

Evaluation of Induction Period Using P(C$_5$H$_4$FeC$_5$H$_5$)(t-BU)$_2$ or P(C$_5$H$_4$FeC$_5$Ph$_5$)(t-Bu)$_2$ as Ligand Pd(dba)$_2$ (0.0287 g, 0.0500 mmol) and either P(C$_5$H$_4$FeC$_5$H$_5$)(t-BU)$_2$ (0.0248 g, 0.0750 mmol) or P(C$_5$H$_4$FeC$_5$Ph$_5$)(t-BU)$_2$ (0.0054 g, 0.0075 mmol) were dissolved in toluene (12.5 mL) and heated at 75° C. for 15 min when using P(C$_5$H$_4$FeC$_5$H$_5$)(t-BU)$_2$ or at 40° C. for 1 h when using P(C$_5$H$_4$FeC$_5$Ph$_5$)(t-Bu)$_2$. These solutions displayed $^{31}$P NMR (C$_7$H$_8$) chemical shift of δ 56.2 for [Pd(FcP-t-Bu$_2$)$_2$] or δ 61.1 for what was presumed to be [Pd(Ph$_5$FcP-t-Bu$_2$)$_2$] or [Pd(Ph$_5$FcP-t-Bu$_2$)(dba)$_n$]. o-Bromotoluene (0.1200 mL, 1.000 mmol), NaOC$_6$H$_4$-4-OMe (0.1651 g, 1.130 mmol), and dodecane as internal standard (0.227 mL, 1.000 mmol) were then added to the Pd(0) solution, and the reaction mixture was heated again at 75° C. when using P(C$_5$H$_4$FeC$_5$H$_5$)(t-Bu)$_2$ or at 40° C. when using P(C$_5$H$_4$FeC$_5$Ph$_5$)(t-Bu)$_2$. An aliquot of the reaction solution was removed every 10–15 min for the first 5 h then 30 min thereafter until the o-bromotoluene reacted completely. The amount of o-bromotoluene and 2-(4-methoxyphenyl)methylphenylether relative to the dodecane internal standard in each aliquot was measured by GC methods. Similar experiments were conduced at room temperature using P(C$_5$H$_4$FeC$_5$Ph$_5$)(t-Bu)$_2$ as ligand and using $^1$H NMR to monitor product formation and reagent decay. Similar results were obtained, although reaction times were longer and product yields were slightly higher and more similar to those of isolated material.

B. Alkoxide and Siloxide Reactions with Aryl Halides

General Procedure for the Palladium Catalyzed Etherification of Aryl Halides

The reaction conditions and results are shown in Table 1.

TABLE 1

Aromatic C—O Bond Formation Catalyzed by 5 mol % Pd(dba)$_2$/Ph$_5$FcP(t-Bu)$_2$.

| Entry | Aryl Halide | Product | | Temp, Time | Yield |
|---|---|---|---|---|---|
| 1 | ⟨phenyl⟩—Br | ⟨phenyl⟩—OR | R = O-t-Bu | RT, 17 h | 96% |
| 2 | ⟨o-tolyl⟩—Br | ⟨o-tolyl⟩—OR | R = O-t-Bu | RT, 14 h | 79% |
| 3 | | | R = OTBS | RT, 16 h | 99% |
| 4 | | | R = OC$_6$H$_4$-4-OMe | RT, 70 h | 99% |

TABLE 1-continued

Aromatic C—O Bond Formation Catalyzed by 5 mol % Pd(dba)₂/Ph₅FcP(t-Bu)₂.

| Entry | Aryl Halide | Product | | Temp, Time | Yield |
|---|---|---|---|---|---|
| 5 | MeO-C₆H₄-X (3-isomer) X = Br | MeO-C₆H₄-OR | R '2 O-t-Bu | RT, 19 h | 77% |
| 6 | X = Cl | | R = OTBS | 80° C., 12 h | 79% |
| 7 | | | R = O-t-Bu | 80° C., 6 h | 92% |
| 8 | | | R = OTBS | 80° C., 12 h | 78% |
| 9 | MeO-C₆H₄-Br (4-isomer) | MeO-C₆H₄-OR | R = O-t-Bu | 80° C., 12 h | 67% |
| 10 | PhC(O)-C₆H₄-X X = Br | R'C(O)-C₆H₄-OR | R = O-t-Bu | RT, 6 h | 98% |
| 11 | X = Br | | R = OTBS | RT, 21 h | 94% |
| 12 | O₂N-C₆H₄-X X = Cl | O₂N-C₆H₄-OR | R = O-t-Bu | RT, 4 h | 98% |
| 13 | X = Br | | R = O-t-Bu | RT, 9 h | 98% |
| 14 | X = Cl | | R = O-t-Bu | RT, 5 h | 93% |
| 15 | 2-(2-bromophenyl)ethanol | 2,3-dihydrobenzofuran | | 80° C., 0.5 h | 58% |
| 16 | | | | n = 1, RT, 5 h | 59% |
| 17 | | | | n = 2, RT, 0.5 h | 64% |
| 18 | | | | n = 1, RT, 15 h | 77% |
| 19 | | | | n = 2, RT, 10 min | 93% |

In Table 1, reactions were conducted in toluene solvent with 0.5 mmol aryl halide substrate and when conducted as an intermolecular process 1.2 equivalents of alkoxide (sodium tert-butoxide) or siloxide (sodium tert-siloxide) in 2 mL of toluene were added as described in the Examples that follow. Isolated yields are an average of at least two runs.

General Procedure for the Palladium-Catalyzed Etherification of Aryl Halides Using tert-BuONa A typical procedure is given for the reaction of Entry 1 in Table 1. A 4 mL vial was charged with bromobenzene (63 mg, 0.40, mmol), Pd(dba)₂ (11.5 mg, 0.02 mmol), Ph₅FcP(t-BU)₂ (14.2 mg, 0.02 mmol) and sodium t-butoxide (47 mg, 0.48 mmol). Anhydrous toluene (2 mL) was added, and the vial was sealed with a cap containing a PTFE septum and removed from the drybox. The reaction mixture was stirred at room temperature for 23 h. The reaction solution was then adsorbed onto silica gel, and the product was isolated by eluting with ethyl acetate/hexanes (0 to 10% gradient) to give 58 mg (97%) of t-butoxybenzene.

Example 5 tert-Butoxybenzene (Table 1, Entry 1)

97% yield. ¹H NMR (300 MHz, CDCl₃): δ 7.28 (t, 2H, J=7.5 Hz), 7.90 (t, 1H, J=7.5 Hz), 7.11 (d, 2H, J=7.5 Hz), 1.37 (s, 9H). ¹³C NMR (100 MHz, CDCl₃): δ 155.33, 128.79, 124.21, 123.29, 78.33, 28.86.

Example 6

2-tert-Butoxytoluene (Table 1, Entry 2)

79% yield, eluted from silica gel using ethyl acetate/hexane (0 to 10% gradient). ¹H NMR (300 MHz, CDCl₃): δ 7.20–6.95 (m, 4H), 2.28 (s, 3H), 1.42 (s, 9H) ¹³C NMR (100 MHz, CDCl₃): δ 154.35, 132.03, 130.84, 126.02, 122.54, 122.18, 78.87, 29.18, 17.21. GC/MS: m/z 149 (M⁺)

Example 7

3-tert-Butoxyanisole (Table 1, Entries 4, 5, and 7)

77% yield from 3-Bromoanisole and 92% yield from 3-Chloroanisole, eluted from silica gel using ethyl acetate/hexane (0 to 10% gradient). ¹H NMR (300 MHz, CDCl₃): δ 7.17 (t, 1H, J=8.1 Hz), 6.64 (t, 2H, J=8.4 and 2.1 Hz), 6.58 (d, 1H, J=2.1 Hz), 3.79 (s, 3H), 1.38 (s, 9H). ¹³C NMR (100 MHz, CDCl₃): δ 160.10, 156.58, 129.04, 116.31, 110.03, 108.71, 78.48, 55.15, 28.86. GC/MS: m/z 180 (M⁺)

Example 8

4-tert-Butoxyanisole (Table 1, Entry 9)

81% yield, eluted from silica gel using ethyl acetate/hexane (0 to 10% gradient). ¹H NMR(300 MHz, CDCl₃): δ

6.94 (d, 2H, J=9.0 Hz), 6.81 (d, 2H, J=9.0 Hz), 3.79 (s, 3H), 1.32 (s, 9H). $^{13}$C NMR (100 MHz, CDCl$_3$): δ 155.72, 148.55, 125.30, 113.75, 77.98, 55.42, 28.67. GC/MS: m/z 180 (M$^+$).

Example 9

4-tert-Butoxybenzophenone (Table 1, Entries 10 and 12)

98% yield from 4-Bromo-benzophenone and 98% yield from 4-Chlorobenzophenone, eluted from silica gel using ethyl acetate/hexane (0 to 10% gradient). $^1$H NMR (300 MHz, CDCl$_3$): δ 7.78 (app. d, 4H, J=8.4 Hz), 7.57–7.45 (m, 3H), 7.06 (app. d, 2H, J=6.9, 1.8 Hz), 1.44 (s, 9H) $^{13}$C NMR (100 MHz, CDCl$_3$): δ 195.70, 159.96, 138.03, 131.92, 131.68, 131.64, 129.72, 128.12, 122.11, 79.54, 28.87. GC/MS: m/z 254 (M$^+$).

Example 10

4-tert-Butoxy-1-nitrobenzene (Table 1, Entries 13, 14)

98% yield from 4-Bromo-1-nitrobenzene and 93% yield from 4-Chloro-1-nitrobenzene, eluted from silica gel using ethyl acetate/hexane (0 to 10% gradient). $^1$H NMR (300 MHz, CDCl$_3$): δ 8.16 (d, 2H, J=9.0 Hz), 7.05 (d, 2H; J=9.0 Hz), 1.46 (s, 9H). $^{13}$C NMR (100 MHz, CDCl$_3$): δ 161.87, 142.35, 125.16, 121.62, 80.56, 28.78.

General Procedure for the Palladium Catalyzed Etherification of Aryl Halides with Sodium t-Butyldimethylsiloxide The reaction conditions and results are shown in Table 1. A by typical procedure is given for the reaction of Entry 3 in Table 1.

A 4 mL vial was charged with 2-bromotoluene (86 mg, 0.50 mmol), Pd(dba)$_2$ (14.0 mg, 0.025 mmol), Ph$_5$FcP(t-Bu)$_2$ (18.0 mg, 0.025 mmol) and sodium tert-butyl-dimethylsiloxide (92 mg, 0.60 mmol). Anhydrous toluene (2 mL) was added to the vial, and the vial was sealed with a cap containing a PTFE septum and removed from the drybox. The reaction mixture was stirred at room temperature for 48 h. The reaction solution was then adsorbed onto silica gel, and the product was isolated by eluting with ethyl acetate/hexanes (0 to 10% gradient) to give 110 mg (99%) of 2-(tert-butyl-dimethylsilyloxy)toluene.

Example 11

2-(tert-Butyl-dimethylsilyloxy)toluene (Table 1, Entry 3)

99% yield. $^1$H NMR (300 MHz, CDCl$_3$): δ 7.17–6.80 (m, 4H), 2.24 (s, 3H), 1.05 (s, 9H), 0.25 (s, 6H). $^{13}$C NMR (100 MHz, CDCl$_3$): δ 153.85, 130.92, 128.91, 126.55, 120.93, 118.47, 25.78, 18.25, 16.80, –3.46. GC/MS: m/z 222 (M$^+$).

Example 12

3-(tert-Butyl-dimethylsilyloxy)anisole (Table 1, Entries 6 and 8)

79% yield from 3-bromoanisole and 67% yield from 3-chloroanisole, eluted from silica gel using ethyl acetate/hexanes (0 to 10% gradient). $^1$H NMR (300 MHz, CDCl$_3$): δ 7.15 (m, 1H), 6.57–6.43 (m, 3H), 3.80 (s, 3H), 1.02 (s, 9H), 0.24 (s, 6H). $^{13}$C NMR (100 MHz, CDCl$_3$): δ 160.59, 156.74, 129.61, 112.50, 106.73, 106.23, 55.13, 25.62, 18.14, –3.58. GC/MS: m/z 238 (M$^+$).

Example 13

4-(tert-Butyl-dimethylsilyloxy)benzophenone (Table 1, Entry 11)

94% yield, eluted from silica gel using ethyl acetate/hexanes (0 to 10% gradient). $^1$H NMR (300 MHz, CDCl$_3$): δ 7.82–7.77 (m, 4H), 7.61–7.56 (m, 1H), 7.51–7.47 (m, 2H), 6.94–6.92 (m, 2H), 1.02 (s, 9H), 0.27 (s, 6H). $^{13}$C NMR (100 MHz, CDCl$_3$): δ 195.65, 159.91, 138.16, 132.43, 131.78, 130.63, 129.72, 128.14, 119.67, 25.57, 18.22, –3.45. GC/MS: m/z 312 (M$^+$).

General Procedure for the Palladium Catalyzed Intramolecular Etherification

The reaction conditions and results are shown in Table 1. A typical procedure is given for the reaction of Entry 19 in Table 1.

A 4 mL vial was charged with 4-(2-bromophenyl)-2-methyl-2-butanol (97 mg, 0.40 mmol), Pd(dba)$_2$ (11.5 mg, 0.02 mmol), Ph$_5$FcP(t-Bu)$_2$ (14.2 mg, 0.02 mmol) and sodium t-butoxide (46 mg, 0.48 mmol). Anhydrous toluene (2 mL) was added into the vial, and the vial was sealed with a cap containing a PTFE septum and removed from the drybox. The reaction mixture was stirred at room temperature for 10 min. The reaction solution was adsorbed onto silica gel and isolated by eluting with 5% ethyl acetate in hexanes to give 60 mg (93%) of 2,2-dimethylchroman as a colorless oil.

Example 14

2,2-Dimethylchroman (Table 1, Entry 19)

93% yield. $^1$H NMR (300 MHz, CDCl$_3$): δ 7.10–7.06 (m, 2H), 6.86–6.78 (m, 2H), 2.80 (dd, 2H, J=6.6, 6.9 Hz), 1.82 (dd, 2H, J=6.6, 6.9 Hz), 1.35 (s, 6H). $^{13}$C NMR (100 MHz, CDCl$_3$): δ 22.21, 26.65, 32.55, 73.86, 116.98, 119.33, 120.67, 126.98, 129.20, 153.73. GC/MS: m/z 162 (M$^+$).

Example 15

2,2-Dimethyl-2,3-dihydrobenzo[b]furan (Table 1, Entry 18)

77% yield, eluted from silica gel using 5% ethyl acetate in hexanes. $^1$H NMR (300 MHz, CDCl$_3$): δ 7.15 (m, 2H), 6.85 (t, 1H, J=7.2 Hz), 6.77 (d, 1H, J=8.1 Hz), 3.04 (s, 2H), 1.51 (s, 6H). $^{13}$C NMR (100 MHz, CDCl$_3$): □158.79, 127.91, 127.03, 125.10, 119.87, 109.46, 86.42, 42.82, 28.17. GC/MS: m/z 148 (M$^+$).

Example 16

2-Methyl-2,3-dihydrobenzo[b]furan (Table 1, Entry 16)

59% yield, eluted from silica gel using 5% ethyl acetate in hexanes. $^1$H NMR (300 MHz, CDCl$_3$): δ 7.19–7.11 (m, 2H), 6.78–6.88 (m, 2H), 4.94 (m, 1H), 3.34 (dd, 1H, J=8.7, 15.3 Hz), 2.84 (dd, 1H, J=7.5, 15.6 Hz), 1.50 (d, 3H, J=6.0 Hz). $^{13}$C NMR (100 MHz, CDCl$_3$): δ 159.46, 127.91, 126.99, 124.92, 120.11, 109.27, 79.43, 37.09, 20.71. GC/MS: m/z 134 (M$^+$).

Example 17

2-Methylchroman (Table 1, Entry 17)

64% yield, eluted from silica gel using 5% ethyl acetate in hexanes. $^1$H NMR (300 MHz, CDCl$_3$): δ 7.14–7.07 (m, 2H), 6.88–6.82 (m, 2H), 4.18 (m, 1H), 2.86 (m, 2H), 2.04 (m, 1H), 1.80 (m, 1H), 1.43 (d, 3H, J=6.3 Hz). $^{13}$C-NMR (100 MHz, CDCl$_3$): δ 154.97, 129.50, 127.20, 121.78, 119.92, 116.62, 72.11, 29.16, 24.85, 21.37. GC/MS: m/z 148 (M$^+$).

Example 18

2,3-Dihydrobenzo[b]furan (Table 1, Entry 15)

58% yield, eluted from silica gel using 5% ethyl acetate in hexanes. $^1$H NMR (300 MHz, CDCl$_3$): δ 7.22 (d, 1H, J=7.2 Hz), 7.14 (app.t, 1H, J=7.5 Hz), 6.85 (app.q, 2H, J=7.5 Hz), 4.58 (app.t, 2H, J=8.7 Hz), 3.24 (app.t, 2H, J=8.7 Hz). $^{13}$C NMR (100 MHz, CDCl$_3$): δ 159.96, 127.87, 127.27, 124.85, 120.29, 109.30, 70.96, 29.70. GC/MS: m/z 120 (M$^+$).

Preparation of Substrates for Intramolecular Etherification

Example 19

2-Methyl-1-(2-bromophenyl)-2-propanol (Table 1, Entry 18)

This material was prepared by literature procedures (Bacon, R. G. R.; Rennison, S. C. *J. Chem. Soc.* (C) 1969, 312–315). $^1$H NMR (300 MHz, CDCl$_3$): δ 7.59 (d, 1H, J=7.8 Hz), 7.37 (dd, 1H, J=7.6, 1.8 Hz), 7.27 (m, 1H), 7.11 (t, 1H, J=7.8, 1.8 Hz), 3.03 (s, 2H), 1.53 (bs, 1H), 1.30 (s, 6H). $^{13}$C NMR (100 MHz, CDCl$_3$): δ 137.66, 133.02, 132.38, 128.10, 127.10, 125.95, 69.83, 47.93, 29.50, 29.43. Anal. Calc'd. for C$_{10}$H$_{13}$BrO: C, 52.42; H, 5.72. Found: C, 52.20; H, 5.63.

Example 20

1-(2-Bromophenyl)-2-propanol (Table 1, Entry 16)

To a solution of 2-(2-bromophenyl)methyl acetate (4.4 g, 19.21 mmol) in 50 mL of anhydrous toluene was added slowly at −78° C. under a nitrogen atmosphere 13.6 mL (20.1 mmol) of a 1 M solution of DIBAL in Toluene. After 2 h, anhydrous methanol (7.8 mL) was added slowly to avoid increasing the temperature and to avoid rapid evolution of gas. The solution was allowed to stand at −78° C. for 1 hr. The mixture was then warmed to room temperature and stirred for an additional 30 min. The solution was diluted with ether (200 mL), washed with brine, and dried with MgSO$_4$. After evaporating the solvent, 2-(2-bromophenyl) methylaldehyde was obtained (3.42 g, 89% yield) as a colorless oil. This aldehyde was used without further purification. $^1$H NMR (300 MHz, CDCl$_3$): δ 9.78 (s, 1H), 7.64 (d, 1H, J=8.1 Hz), 7.34–7.18 (m, 3H), 3.89 (s, 2H). To a solution of methyl magnesium chloride (8.8 mL, 25.65 mmol) in anhydrous THF was added at −20° C. a solution of 2-(2-bromophenyl)methylaldehyde in anhydrous ether (50 mL). The mixture was stirred at −20° C. for 0.5 h and at room temperature for 1 h. The resulting solution was carefully poured into a mixture of ether (100 mL) and water (100 mL). The organic layer was separated, washed with brine, and dried with anhydrous magnesium sulfate. After evaporation of the solvent, 1-(2-bromophenyl)-2-propanol was purified by flash chromatography on silica gel using ethyl acetate/hexanes (5 to 10%) as eluent to afford 2.67 g (73% yield) of colorless oil. $^1$H NMR (300 MHz, CDCl$_3$): δ 7.57 (d, 1H, J=7.8 Hz), 7.27 (d, 2H, J=4.2 Hz), 7.12 (m, 1H), 4.12 (m, 1H), 2.98 (dd, 1H, J=13.5, 4.8 Hz), 2.85 (dd, 1H, J=13.5, 8.1 Hz), 1.59 (bs, 1H), 1.29 (d, 3H, J=6.3 Hz). $^{13}$C NMR (100 MHz, CDCl$_3$): δ 138.11, 132.99, 131.68, 128.16, 127.38, 124.87, 67.47, 45.62, 22.97. Anal. Calc'd. for C$_9$H$_{11}$BrO: C, 50.26; H, 5.15. Found: C, 50.06; H, 5.06.

Example 21

2-Bromophenethyl Alcohol (Table 1, Entry 15)

To a solution of 2-bromophenylacetic acid (3.96 g, 18.42 mmol) in 60 mL of anhydrous THF was added slowly at room temperature 24.0 mL (23.95 mmol) of a 1 M solution BH$_3$/THF. After finishing the addition of BH$_3$/THF, the solution was stirred at room temperature for 1 h and then heated at 100° C. for 2 h. After this time, the solution was cooled to room temperature, and a mixture of THF and water (20 mL) was added. Potassium carbonate was then added, along with 60 mL of ether. The organic layer was separated from the mixture, and this layer was washed with water (60 mL), aqueous NaHCO$_3$ (60 mL), and brine (60 mL) before it was dried over magnesium sulfate, filtered, and concentrated to give the crude product. This crude product was purified by silica gel flash chromatography eluting with hexanes and a 5 to 10% gradient of ethyl acetate to give 3.47 g (94%) as a colorless oil. 1H NMR (300 MHz, CDCl$_3$): δ 7.57 (d, 1H, J=7.8 Hz), 7.31–7.21 (m, 2H), 7.14–7.08 (m, 1H), 3.90 (app. t, 2H, J=6.6, 6.9 Hz), 3.05 (app. t, 2H, J=6.6 Hz), 1.51 (bs, 1H). $^{13}$C NMR (100 MHz, CDCl$_3$): δ 137.76, 132.95, 131.25, 128.19, 127.44, 124.67, 62.04, 39.30. Anal. Calc'd. for C$_8$H$_9$BrO: C, 47.79; H, 4.51. Found: C, 47.75; H, 4.50.

Example 22

4-(2-Bromophenyl)-2-methyl-2-butanol (Table 1, Entry 19)

This material was prepared by literature procedures (Bacon, R. G. R.; Rennison, S. C. *J. Chem. Soc.* (C) 1969, 312–315). $^1$H NMR (400 MHz, CDCl$_3$): δ 7.54 (d, 1H, J=7.2 Hz), 7.31–7.24 (m, 2H), 7.09–7.06 (m, 1H), 2.87–2.82 (m, 2H), 1.80–1.75 (m, 2H), 1.43 (bs, 1H), 1.34 (s, 6H). $^{13}$C-NMR (100 MHz, CDCl$_3$): δ 141.71, 132.78, 130.24, 127.54, 127.52, 124.34, 70.91, 44.00, 31.30, 29.19. Calcd for C$_{11}$H$_{15}$BrO: C, 54.34; H, 6.22. Found: C, 54.52; H, 6.30.

Example 23

4-(2-Bromophenyl)-2-butanol (Table 1, Entry 17)

This material was prepared by literature procedures (Bacon, R. G. R.; Rennison, S. C. *J. Chem. Soc.* (C) 1969, 312–315). $^1$H NMR (400 MHz, CDCl$_3$): δ 7.55 (d, 1H, J=7.6 Hz), 7.28–7.23 (m, 2H), 7.11–7.05 (m, 1H), 3.92–3.86 (m, 1H), 2.95–2.77 (m, 2H), 1.83–1.75 (m, 2H), 1.55 (bs, 1H), 1.28 (d, 3H, J=6.0 Hz). $^{13}$C-NMR (100 MHz, CDCl$_3$): δ 141.31, 132.78, 130.35, 127.57, 127.47, 124.36, 67.48, 39.23, 32.42, 23.57.

B. Amination Reactions of Aryl Halides

General Methods, Procedure A

A typical procedure is given for the reaction of Entry 1 in Table 2. A 4 ml vial was charged with bromobenzene (171 mg, 1.10 mmol), diphenylamine (169 mg, 1.00 mmol), Pd(dba)$_2$ (5.9 mg, 1 mol %), Ph$_5$FcP(t-Bu)$_2$(7.1 mg, 2 mol %), and sodium tert-butoxide (144 mg, 1.50 mmol). Anhydrous toluene (1 ml) was added into the mixture, and the vial was then sealed with a cap containing PTFE septum. The reaction mixture was stirred at room temperature for 1 h.

dAfter the starting aryl halide was consumed detected, as determined by GC, the reaction solution was directly absorbed onto silica gel, and the product was isolated by eluting with hexane/ethyl acetate to give 244 mg (99%) of triphenylamine as a white solid. Reaction of chlorobenzene (62 mg, 0.55 mmol) with diphenylamine (85 mg, 0.50 mmol) proceeded at 80° C. over 21 h to give triphenylamine (121 mg, 98%).

N,N,N-triphenylamine $^1$H-NMR (400 MHz, CDCl$_3$): δ 7.26 (t, 6H, J=7.2 Hz), 7.11 (d, 6H, J=7.6 Hz), 7.02 (app. t, 3H, J=7.2 and 7.6 Hz). $^{13}$C{$^1$H}-NMR (100 MHz, CDCl$_3$): δ 147.83, 129.17, 124.14, 122.63. GC/MS (EI): m/z 245 (M$^+$).

General Methods, Procedure B

A typical procedure is given for the reaction of Entry 6 in Table 7. A 4 ml vial was charged with 4-tert-butylbromiobenzene (108 mg, 0.51 mmol), Pd(OAc)$_2$ (3.1 mg, 1 mol %), Ph$_5$FcP(t-Bu)$_2$ (7.1 mg, 2 mol %), and sodium tert-butoxide (60 mg, 0.60 mmol). Anhydrous toluene was added, and the vial was sealed with a cap containing PTFE septum and removed from the drybox. 80 μl of n-hexylamine was added to the vial through the septum using syringe. Reaction mixture was then heated to 100° C. for 2 h to give the title compound (113 mg, 95%) as a colorless oil:

The reaction conditions and results are shown in Tables 2–9.

TABLE 2

Amination Reaction of Aryl Halides with Secondary Amines using Pd/Ph$_5$FcP(tBu)$_2$ Catalyst

| Entry | Halide | amine | Product | Condition | Yield (%) |
| --- | --- | --- | --- | --- | --- |
| 1 | PhBr | NHPh$_2$ | NPh$_3$ | 1 mol % (Pd/L) NaOtBu/Toln. RT, 1 hr | 99 |
| 2 | PhCl | ↑ | ↑ | 1/2 mol % (Pd/L) NaOtBu/Toln. 100° C., 21 hr | 98 |
| 3 | 4-MeO-C$_6$H$_4$-Cl | ↑ | 4-MeO-C$_6$H$_4$-NPh$_2$ | 1 mol % (Pd/L) NaOtBu/Toln. RT to 80° C. | 99 |
| 4 | 2-CH$_3$-C$_6$H$_4$-Br | ↑ | 2-CH$_3$-C$_6$H$_4$-NPh$_2$ | 1 mol % (Pd/L) NaOtBu/Toln. RT, 4 hr | 99 |
| 5 | 2-CH$_3$-C$_6$H$_4$-Cl | ↑ | ↑ | 1/2 mol % (Pd/L) NaOtBu/Toln. 100° C., 21 hr | 99 |
| 6 | 4-NC-C$_6$H$_4$-Cl | ↑ | 4-NC-C$_6$H$_4$-NPh$_2$ | 1/2 mol % (Pd/L) NaOtBu/Toln. 50° C., 21 hr | 96 |
| 7 | 2-OMe-C$_6$H$_4$-Cl | ↑ | 2-OMe-C$_6$H$_4$-NPh$_2$ | 0.5/1.0 mol % (Pd/L) NaOtBu/Toln. 100° C. | 99 |

TABLE 3

Amination Reaction of Aryl Halides with Secondary Amines using Pd/Ph₅FcP(tBu)₂ Catalyst

| Entry | Halide | amine | Product | Condition | Yield (%) |
|---|---|---|---|---|---|
| 1 | 2-bromotoluene | morpholine (HN-morpholine) | 2-methylphenyl-morpholine | 1 mol % (Pd/L) NaOtBu/Toln. | 40 |
| 2 | 4-chloroanisole | ↑ | 4-methoxyphenyl-morpholine | 2 mol % (Pd/L) NaOtBu/Toln. RT to 80° C. | 85 |
| 3 | 3-bromoanisole | ↑ | 3-methoxyphenyl-morpholine | 1/2 mol % (Pd/L) NaOt-Bu/Toln. 100° C., 21 hr | 96 |
| 4 | 4-bromo-t-butylbenzene | ↑ | 4-t-butylphenyl-morpholine | 1/2 mol % (Pd/L) NaOt-Bu/Toln. 70° C., 27 hr | 82 |
| 5 | 4-chlorotoluene | ↑ | 4-methylphenyl-morpholine | 1/2 mol % (Pd/L) NaOt-Bu/Toln. 70° C., 27 hr | 98 |
| 6 | 4-chlorobenzonitrile | ↑ | 4-cyanophenyl-morpholine | 1/2 mol % Pd(dba)₂/L NaOtBu, toln. 45° C., 24 hr | 82 |

TABLE 4

Amination Reaction of Aryl Halides with Secondary Amines using Pd/Ph₅FcP(tBu)₂ Catalyst

| Entry | Halide | amine | Product | Condition | Yield (%) |
|---|---|---|---|---|---|
| 1 | 4-bromo-t-butylbenzene | dibutylamine (HN(Bu)₂) | 4-t-butyl-N,N-dibutylaniline | 1 mol % (Pd/L) NaOtBu/Toln. RT to 60° C. | 89 |

TABLE 4-continued

Amination Reaction of Aryl Halides with Secondary Amines using Pd/Ph₅FcP(tBu)₂ Catalyst

| Entry | Halide | amine | Product | Condition | Yield (%) |
|---|---|---|---|---|---|
| 2 | 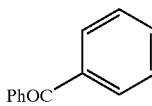 | ↑ | 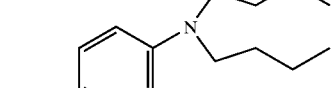 | 1 mol % (Pd/L) NaOtBu/Toln. RT, 17 hr | 99 |
| 3 | 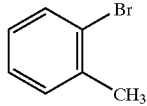 | ↑ | 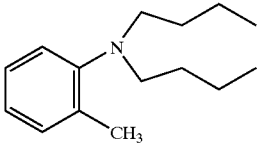 | 1 mol % (Pd/L) NaOtBu/Toln. RT, 17 hr | 37 |
| 4 | 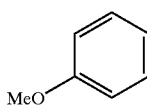 | ↑ | 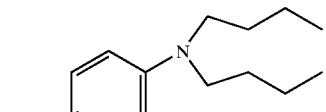 | 1/2 mol % (Pd/L) NaOt-Bu/Toln. 100° C., 17 hr | 91 |
| 5 | 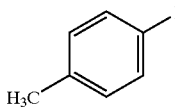 | ↑ | 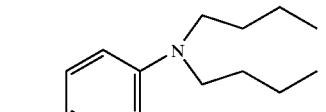 | 1/2 mol % (Pd/L) NaOt-Bu/Toln. 40° C., 24 hr | 93 |
| 6 | 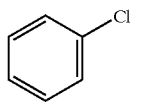 | ↑ | 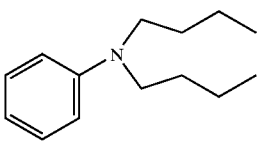 | 1/2 mol % (Pd/L) NaOt-Bu/Toln. 100° C., 24 hr | 95 |
| 7 | 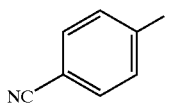 | ↑ | 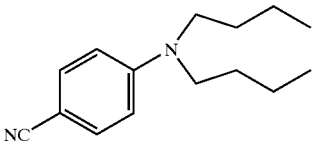 | 1/2 mol % (Pd/L) K₃PO₄/Toln. 100° C., 6 hr | 94 |
| 8 | 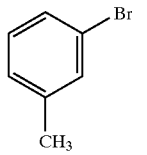 | ↑ | 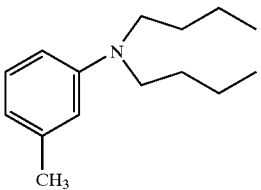 | 1/2 mol % (Pd/L) NaOt-Bu/Toln. | 99 |

TABLE 5

Amination Reaction of Aryl Halides with Secondary Amines using Pd/Ph₅FcP(tBu)₂ Catalyst

| Entry | Halide | amine | Product | Condition | Yield (%) |
|---|---|---|---|---|---|
| 1 | 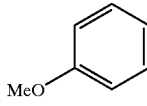 | 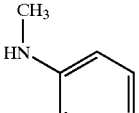 | 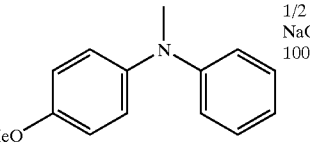 | 1/2 mol % (Pd/L) NaOtBu/Toln. 100° C., 25 hr | 96 |

TABLE 5-continued

Amination Reaction of Aryl Halides with Secondary Amines using Pd/Ph₅FcP(tBu)₂ Catalyst

| Entry | Halide | amine | Product | Condition | Yield (%) |
|---|---|---|---|---|---|
| 2 | 2-chlorotoluene | ↑ | N-methyl-N-phenyl-2-methylaniline | 1/2 mol % (Pd/L) NaOtBu/Toln. 100° C., 28 hr | 95 |
| 3 | 4-bromobenzonitrile | ↑ | 4-(N-methyl-N-phenylamino)benzonitrile | 1/2 mol % (Pd/L) NaOtBu/Toln. 40° C., 19 hr | 93 |
| 4 | 4-bromo-t-butylbenzene | ↑ | 4-t-butyl-N-methyl-N-phenylaniline | 1/2 mol % (Pd/L) NaOtBu/Toln. 100° C., 19 hr | 98 |

TABLE 6

Amination Reaction of Aryl halides with primary-amines (aniline) using by Pd/Ph₅FcP(t-Bu)₂ catalyst

| Entry | Halide | amine | Product | Condition | Yield (%) |
|---|---|---|---|---|---|
| 1 | 4-chloroanisole | H₂N-Ph | 4-methoxy-N-phenylaniline | 1/2 mol % (Pd/L) NaOtBu/Toln. 70° C., 15 hr | 95 |
| 2 | 2-chlorotoluene | ↑ | 2-methyl-N-phenylaniline | 1/2 mol % (Pd/L) NaOtBu/Toln. 70° C., 15 hr | 97 |
| 3 | 4-chlorobenzonitrile | ↑ | 4-(phenylamino)benzonitrile | 1/2 mol % (Pd/L) NaOtBu/Toln. 70° C. | 73 |
| 4 | chlorobenzene | ↑ | diphenylamine | 1/2 mol % (Pd/L) NaOtBu/Toln. 70° C., 15 hr | 86 |
| 5 | bromobenzene | ↑ | ↑ | 1 mol % (Pd/L) NaOtBu/Toln. RT, 4 hr | 98 |

TABLE 7

Amination Reaction of Aryl halides with primary-amines using Pd/Ph₄FcP(t-Bu)₂ catalyst

| Entry | Halide | amine | Product | Condition | Yield (%) |
|---|---|---|---|---|---|
| 1 | 4-Cl-C₆H₄-OMe | H₂N-n-hexyl | 4-MeO-C₆H₄-NH-n-Hex | 2/4 mol % (Pd/L) NaOtBu/Toln. 100° C., 15 hr | 75 |
| 2 | 2-Cl-C₆H₄-CH₃ | ↑ | 2-CH₃-C₆H₄-NH-n-Hex | 1/2 mol % (Pd/L) NaOtBu/Toln. 70° C., 8 hr | 92 |
| 3 | 4-Cl-C₆H₄-CN | ↑ | 2-CH₃-C₆H₄-NH-n-Hex | 1/2 mol % (Pd/L) K₃PO₄/DME 100° C., 13 hr | 92 |
| 4 | 4-Cl-C₆H₄-CN | ↑ | 4-NC-C₆H₄-NH-n-Hex | 1/2 mol % (Pd/L) NaOtBu/Toln. 70° C., 8 hr | 78 |
| 5 | 4-Cl-C₆H₄-OC(O)Ph | ↑ | 4-PhOC-C₆H₄-NH-n-Hex | 1/2 mol % (Pd/L) NaOtBu/Toln. 50° C., 13 hr | 93 |
| 6 | 4-Br-C₆H₄-t-Bu (1.0/1.2) | ↑ | ↑ | 1/2 mol % (Pd/L) NaOtBu/Toln. 100° C. | 94 |
| 7 | 3-X-C₆H₄-OMe, X = Br | ↑ | 3-MeO-C₆H₄-NH-n-Hex | 1/2 mol % (Pd/L) NaOtBu/Toln. RT | 85 |
| 8 | X = Cl | ↑ | ↑ | 1/2 mol % (Pd/L) NaOtBu/Toln. 100° C. | 95 |
| 9 | 2,5-(CH₃)₂-4-Cl-C₆H₃ | ↑ | 2,5-(CH₃)₂-C₆H₃-NH-n-Hex | 1/2 mol % (Pd/L) NaOtBu/Toln. 100° C. | 87 |
| 10 | 2,6-(CH₃)₂-Cl-C₆H₃ | ↑ | 2,6-(CH₃)₂-C₆H₃-NH-n-Hex | 2/4 mol % (Pd/L) NaOtBu, Toln. 100° C. | 97 |
| 11 | 2-Cl-C₆H₄-OMe | ↑ | 2-MeO-C₆H₄-NH-n-Hex | 1/2 mol % (Pd/L) NaOtBu, Toln. 100° C. | 97 |

TABLE 7-continued

Amination Reaction of Aryl halides with primary-amines using Pd/Ph₅FcP(t-Bu)₂ catalyst

| Entry | Halide | amine | Product | Condition | Yield (%) |
|---|---|---|---|---|---|
| 12 | 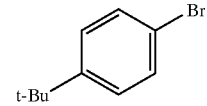 | ↑ | #1 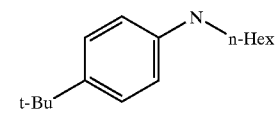 | 1/2 mol % (Pd/L) NaotBu, Toln. 100° C., 4 hr | 99 |

1 ArX/amine = 2.2/1.0

TABLE 8

Amination Reaction of Aryl halides with primary-amines using Pd/Ph₅FcP(t-Bu)₂ catalyst

| Entry | Halide | amine | Product | Condition | Yield (%) |
|---|---|---|---|---|---|
| 1 | 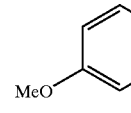 |  | 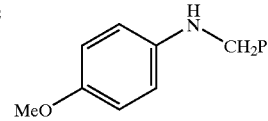 | 1/2 mol % (Pd/L) NaOtBu/Toln. 100° C., 24 hr | 93 |
| 2 | 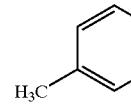 | ↑ | 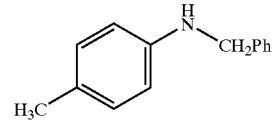 | 1/2 mol % (Pd/L) NaOtBu/Toln. 100° C., 24 hr | 90 |
| 3 | 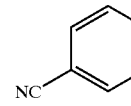 | ↑ | 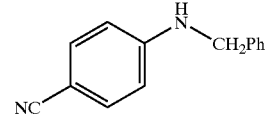 | 1/2 mol % (Pd/L) NaOtBu/Toln. 50° C., 24 hr | 76 |
| 4 | 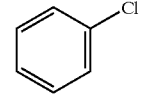 | ↑ | 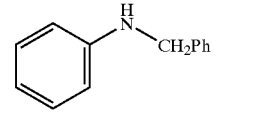 | 1/2 mol % (Pd/L) NaOtBu/Toln. 100° C., 24 hr | 93 |
| 5 | 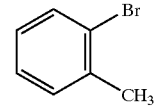 | ↑ | 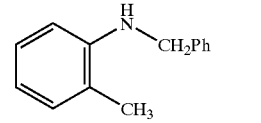 | 1/2 mol % (Pd/L) NaOtBu/Toln. 100° C. | 96 |

TABLE 9

Amination Reaction of Functionalized Aryl halides using by K₃PO₄/monoglyme as base and solvent

| Entry | Halide | amine | Product | Condition | Yield (%) |
|---|---|---|---|---|---|
| 1 | 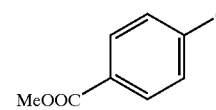 | 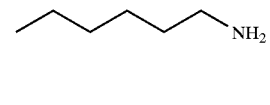 | 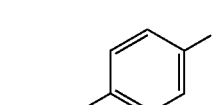 | 2/4 mol % (Pd/L) K3PO4, DME 100° C., 20 hr | 86 |

TABLE 9-continued

Amination Reaction of Functionalized Aryl halides using by $K_3PO_4$/monoglyme as base and solvent

| Entry | Halide | amine | Product | Condition | Yield (%) |
|---|---|---|---|---|---|
| 2 | (same as above) | N-methylaniline | MeOOC-C6H4-N(CH3)Ph | 1/2 mol % (Pd/L) K3PO4, DME 100° C. | 99 |
| 3 | (same as above) | aniline | MeOOC-C6H4-NH-Ph | ↑ | 95 |
| 4 | (same as above) | di-n-butylamine | MeOOC-C6H4-N(n-Bu)2 | ↑ | 96 |
| 5 | 4-chloronitrobenzene | morpholine | O2N-C6H4-morpholine | 1/2 mol % (Pd/L) K3PO4, DME 100° C., 20 hr | 56 |
| 6 | 4-chloronitrobenzene | aniline | O2N-C6H4-NH-Ph | ↑ | 95 |

Example 24

Table 2, Entries 1 and 2

Following the reaction procedure of Procedure A above, triphenyl amine was prepared, and had the following characteristics: $^1$H-NMR (400 MHz, CDCl$_3$): δ 7.26 (t, 6H, J=7.2 Hz), 7.11 (d, 6H, J=7.6 Hz), 7.02 (app.t, 3H, J=7.2 and 7.6 Hz). $^{13}$C{$^1$H}-NMR (100 MHz, CDCl$_3$): δ 147.83, 129.17, 124.14, 122.63. GC/MS (EI): m/z 245 (M$^+$).

Example 25

N-(4-methoxyphenyl)diphenylamine (Table 2, Entry 3)

According to the general procedure A described above, 4-chloroanisole (130 mg, 0.92 mmol) reacted with diphenylamine (169 mg, 1.00 mmol) at 80° C. for 12 h using 1 mol % of Pd(dba)$_2$/Ph$_5$FcP(t-Bu)$_2$ catalyst and sodium tert-butoxide to give the title compound (270 mg, 99%) as a solid: $^1$H-NMR (300 MHz, CDCl$_3$): δ 7.30 (app.t, 4H, J=7.5 and 8.1 Hz), 7.17 (app.t, 6H, J=8.4 and 9.0 Hz), 7.04 (app.t, 2H, J=7.2 and 6.9 Hz), 6.94 (d, 2H, J=9.0 Hz), 3.88 (s, 3H). $^{13}$C{$^1$H}-NMR (100 MHz, CDCl$_3$): δ 156.11, 148.13, 140.74, 129.04, 127.26, 122.84, 121.78, 114.71, 55.44. GC/MS(EI): m/z 275 (M$^+$).

Example 26

N-(2-tolyl)diphenylamine (Table 2, Entries 4 and 5)

According to the general procedure A, 2-bromotoluene (188 mg, 1.10 mmol) reacted with diphenylamine (169 mg, 1.00 mmol) to give the title compound (258 mg, 99%) as a white solid at room temperature for 4 h. Reaction of 2-chlorotoluene (70 mg, 0.55 mmol) with diphenylamine (85 mg, 0.50 mmol) proceeded at 80° C. for 21 h to give the title compound (134 mg, 99%). $^1$H-NMR (400 MHz, CDCl$_3$): δ 7.14–7.27 (m, 8H), 7.01–6.92 (m, 6H), 2.06 (s, 3H). $^{13}$C{$^1$H}-NMR (100 MHz, CDCl$_3$): δ 147.46, 145.37, 136.49, 131.67, 129.61, 128.99, 127.33, 125.95, 121.50, 121.33, 18.56. GC/MS(EI): m/z 259 (M$^+$).

Example 27

N-(4-cyanophenyl)diphenylamine (Table 2, Entry 6)

According to the general procedure A, 4-chlorobenzonitrile (76 mg, 0.55 mmol) reacted with diphenylamine (85 mg, 0.50 mmol) using 1 mol % of catalyst and sodium tert-butoxide (72 mg, 0.75 mmol) at 45° C. for 21 h to give the title compound (136 mg, 96%) as a white solid: $^1$H-NMR (400 MHz, CDCl$_3$): δ 7.43 (d, 2H, J=8.8 Hz, Ar—H), 7.35 (m, 4H), 7.17 (m, 6H), 6.97 (d, 2H, J=8.8 Hz). $^{13}$C{$^1$H}-NMR (100 MHz, CDCl$_3$): δ 151.56, 145.93, 133.16, 129.75, 126.14, 125.11, 119.69, 119.67, 102.46. GC/MS(EI): m/z 270 (M$^+$).

Example 28

N-(2-methoxyphenyl)diphenylamine (Table 2, Entry 7) N-(2-methoxyphenyl)diphenylamine According to the general procedure A, 2-chloroanisole (143 mg, 1.00 mmol) reacted with diphenylamine (177 mg, 1.05 mmol) using 0.5/1.0 mol % of Pd(dba)$_2$/Ph$_5$FcP(t-Bu)$_2$ and sodium tert-butoxide (106 mg, 1.10 mmol) in toluene (2 ml) at 100° C. for 5 h to give the title compound (270 mg, 95%): $^1$H-NMR (400 MHz, CDCl$_3$): δ 7.11–7.05 (m, 6H), 6.91–6.89 (m, 4H), 6.85–6.79 (m, 4H), 3.51 (s, 3H). $^{13}$C{$^1$H}-NMR (100 MHz, CDCl$_3$): δ 155.59, 147.62, 135.43, 130.10, 128.75, 126.68, 121.51, 121.49, 121.35, 113.18, 55.76. GC/MS(EI): m/z 244 (M$^+$–OMe), 182. Anal. Calcd for C$_{19}$H$_{17}$NO. C, 82.88; H, 6.22; N, 5.22. Found C, 83.02; H, 6.21; N, 5.22.

Example 29

N-(2-methylphenyl)morpholine (Table 3, Entry 1)

According to the general procedure B, 2-bromotoluene (171 mg, 1.00 mmol) reacted with morpholine (104 mg, 1.20 mmol) using 1 mol % of catalyst and sodium tert-butoxide (134 mg, 1.40 mmol) at room temperature for 43 h to give the title compound (70 mg, 40%) as an oil after purification: $^1$H-NMR (300 MHz, CDCl$_3$): δ 7.22–7.18 (m, 2H), 7.06–7.00 (m, 2H), 3.87 (t, 4H, J=4.5 Hz), 2.93 (t, 4H, J=4.5 Hz), 2.34 (s, 3H). GC/MS(EI): m/z 177 (M$^+$).

Example 30

N-(4-methoxyphenyl)morpholine (Table 3, Entry 2)

According to the general procedure B, 4-chloroanisole (82 mg, 0.55 mmol) reacted with morpholine (46 mg, 0.53 mmol) using 1 mol % of catalyst and sodium tert-butoxide (63 mg, 0.60 mmol) at 70° C. for 27 h to give the title compound (97 mg, 95%) as a solid: $^1$H-NMR (400 MHz, CDCl$_3$): δ 6.92–6.85 (m, 4H), 3.87 (t, 4H, J=4.8 Hz), 3.78 (s, 3H), 3.07 (t, 4H, J=4.8 Hz). $^{13}$C{$^1$H}-NMR (100 MHz, CDCl$_3$): δ 153.92, 145.60, 117.77, 114.47, 67.00, 55.52, 50.78. GC/MS(EI); m/z 193 (M$^+$).

Example 31

N-(3-methoxyphenyl)morpholine (Table 3, Entry 3)

According to the general procedure B, 3-bromoanisole (82 mg, 0.44 mmol) reacted with morpholine (36 mg, 0.41 mmol) using 1 mol % of catalyst and sodium tert-butoxide (42 mg, 0.44 mmol) at 100° C. for 21 h to give the title compound (76 mg, 96%) as an oil: $^1$H-NMR (300 MHz, CDCl$_3$): δ 7.21 (t, 1H, J=8.1 and 8.7 Hz), 6.57–6.45 (m, 3H), 3.87 (t, 4H, J=4.5 and 5.1 Hz), 3.81 (s, 3H), 3.17 (t, 4H, J=4.5 and 5.1 Hz). $^{13}$C{$^1$H}-NMR (100 MHz, CDCl$_3$): δ 160.00, 152.67, 129.83, 108.43, 104.68, 102.18, 66.86, 55.15, 49.25. GC/MS(EI): m/z 193 (M$^+$).

Example 32

N-(4-tert-butylphenyl)morpholine (Table 3, Entry 4)

According to the general procedure B, 4-tert-butylbromobenzene (94 mg, 0.44 mmol) reacted with morpholine (36 mg, 0.41 mmol) using 1 mol % of catalyst and sodium tert-butoxide (42 mg, 0.44 mmol) at 100° C. for 21 h to give the title compound (72 mg, 82%) as a white solid: $^1$H-NMR (300 MHz, CDCl$_3$): δ 7.35 (d, 2H, J=8.7 Hz), 6.91 (d, 2H, J=8.7 Hz), 3.89 (t, 4H, J=4.5 and 4.8 Hz), 3.17 (t, 4H, J=4.5 and 4.8 Hz), 1.34 (s, 9H). $^{13}$C{$^1$H}-NMR (100 MHz, CDCl$_3$): δ 148.89, 142.76, 125.95, 115.38, 66.99, 49.54, 33.94, 31.42. GC/MS(EI): m/z 219 (M$^+$), 204 (M$^+$–CH$_3$), 146 (M$^+$–morpholine).

Example 33

N-(4-methylphenyl)morpholine (Table 3, Entry 5)

According to the general procedure B, 4-methylchlorobenzene (71 mg, 0.56 mmol) reacted with morpholine (46 mg, 0.53 mmol) using 1 mol % of catalyst and sodium tert-butoxide (60 mg, 1.03 mmol) at 70° C. for 27 h to give the title compound (92 mg, 98%) as a solid: $^1$H-NMR (300 MHz, CDCl$_3$): δ 7.12 (d, 2H, J=8.7 Hz), 6.87 (d, 2H, J=8.7 Hz), 3.89 (t, 4H, J=4.8 Hz), 3.14 (t, 4H, J=4.8 Hz), 2.31 (s, 3H). $^{13}$C{$^1$H}-NMR (100 MHz, CDCl$_3$): δ 149.09, 129.64, 129.51, 115.97, 66.90, 49.86, 20.38. GC/MS (EI): m/z 177 (M$^+$).

Example 34

N-(4-cyanophenyl)morpholine (Table 3, Entry 6)

According to the general to procedure B, 4-chlorocyanobenzene (71 mg, 0.52 mmol) reacted with morpholine (53 mg, 0.61 mmol) using 1 mol % of catalyst and sodium tert-butoxide (58 mg, 0.60 mmol) at 45° C. for 27 h to give the title compound (77 mg, 82%) as a solid: $^1$H-NMR (400 MHz, CDCl$_3$): δ 7.49 (d, 2H, J=8.0 Hz), 6.85 (d, 2H, J=8.8 Hz), 3.84 (t, 4H, J=4.8 Hz), 3.27 (t, 4H, J=4.8 Hz). $^{13}$C{$^1$H}-NMR (100 MHz, CDCl$_3$): δ 153.36, 133.36, 119.76, 113.93, 100.69, 66.31, 47.15. GC/MS(EI): m/z 188 (M$^+$).

Example 35

N,N-dibutyl-4-tert-butylaniline (Table 4, Entry 1)

According to the general procedure B, 2-tert-butylbromobenzene (213 mg, 1.00 mmol) reacted with N,N-di-n-butylamine (130 mg, 1.00 mmol) using 1 mol % of catalyst and sodium tert-butoxide (115 mg, 1.20 mmol) at 60° C. to give the title compound (233 mg, 89%) as an oil: $^1$H-NMR (300 MHz, CDCl$_3$): δ 7.25 (d, 2H, J=8.7 Hz), 6.62 (d, 2H, J=8.7 Hz), 3.25 (t, 4H, J=7.2 and 8.1 Hz), 1.58 (m, 4H), 1.35 (M, 4H), 1.30 (s, 9H), 0.97 (t, 6H, J=7.2 Hz). $^{13}$C{$^1$H}-NMR (100 MHz, CDCl$_3$): δ 146.01, 137.59, 125.92, 111.29, 50.84, 33.61, 31.56, 29.53, 20.39, 14.02. GC/MS(EI): m/z 261 (M$^+$).

Example 36

N,N-dibutyl-(4-phenylcarbonyl)aniline (Table 4, Entry 2)

According to the general procedure B, 2-bromobenzophenone (265 mg, 1.02 mmol) reacted with N,N-di-n-butylamine (146 mg, 1.13 mmol) using 1 mol % of catalyst and sodium tert-butoxide (116 mg, 1.20 mmol) at room temperature to give the title compound (310 mg, 99%) as an oil: $^1$H-NMR (300 MHz, CDCl$_3$): δ 7.80 (d, 2H, J=8.7 Hz), 7.74 (d, 2H, J=7.5 Hz), 7.51–7.42 (m, 3H), 6.36 (d, 2H, J=9.0 Hz), 3.35 (t, 4H, J=7.5 and 7.8 Hz), 1.62 (m, 4H), 1.38 (m, 4H), 0.98 (t, 6H, J=7.5 and 7.2 Hz). $^{13}$C{$^1$H}-NMR (100 MHz, CDCl$_3$): δ 194.67, 151.39, 139.40, 132.91, 130.82, 129.25, 127.87, 123.79, 110.08, 50.67, 29.24, 20.19, 13.88. GC/MS (EI): m/z 309 (M$^+$), 266, 224, 210, 105, 77. Anal. Calcd for C$_{21}$H$_{27}$NO: C, 81.51; H, 8.79; N, 4.53. Found: C, 81.26; H, 8.89; N, 4.58.

Example 37

N,N-dibutyl-2-methylaniline (Table 4, Entry 3)

According to the general procedure B, 2-bromotoluene (171 mg, 1.00 mmol) reacted with N,N-di-n-butylamine (129 mg, 1.00 mmol) using 1 mol % of catalyst and sodium tert-butoxide (115 mg, 1.20 mmol) at 60° C. to give the title compound (79 mg, 37%) as an oil: $^1$H-NMR (300 MHz, CDCl$_3$): δ 7.20–7.08 (m, 3H), 6.98 (app.t, 1H), 2.94 (t, 4H), 1.41 (m, 4H), 1.27 (m, 4H), 0.88 (t, 6H). GC/MS (EI): m/z 219 (M$^+$).

Example 38

N,N-dibutyl-4-methoxylaniline (Table 4, Entry 4)

According to the general procedure B, 4-chloroanisole (150 mg, 1.05 mmol) reacted with N,N-di-n-butylamine (160 mg, 1.24 mmol) using 1 mol % of catalyst and sodium tert-butoxide (120 mg, 1.25 mmol) at 100° C. for 20 h to give the title compound (230 mg, 93%) as an colorless oil: $^1$H-NMR (400 MHz, CDCl$_3$): δ 6.74 (d, 2H, J=9.2 Hz), 6.58 (d, 2H, J=9.2 Hz), 3.68 (s, 3H), 3.11 (t, 4H, J=8.0 and 7.2 Hz), 1.45 (m, 4H), 1.26 (m, 4H), 0.86 (t, 6H, J=7.6 and 7.2 Hz). $^{13}$C{$^1$H}-NMR (100 MHz, CDCl$_3$): δ 150.96, 143.33, 114.79, 114.33, 55.82, 51.65, 29.46, 20.40, 14.02. GC/MS (EI): m/z 235 (M$^+$), 235, 192, 150.

Example 39

N,N-dibutyl-4-methylaniline (Table 4, Entry 5)

According to the general procedure B, 4-bromotoluene (94 mg, 0.55 mmol) reacted with N,N-di-n-butylamine (65 mg, 0.50 mmol) using 1 mol % of catalyst and sodium tert-butoxide (58 mg, 0.60 mmol) at 40° C. for 24 h to give the title compound (102 mg, 93%) as a colorless oil: $^1$H-NMR (300 MHz, CDCl$_3$): δ 7.07 (d, 2H, J=8.4 Hz), 6.64 (d, 2H, J=8.4 Hz), 3.28 (t, 4H, J=7.2 and 7.8 Hz), 2.30 (s, 3H), 1.60 (m, 4H), 1.40 (m, 4H), 1.00 (t, 6H, J=7.5 and 7.2 Hz). $^{13}$C{$^1$H}-NMR (100 MHz, CDCl$_3$): δ 146.17, 129.67, 124.34, 112.19, 50.99, 29.41, 20.38, 20.12, 14.01. GC/MS (EI): m/z 219 (M$^+$), 176, 134.

Example 40

N,N-dibutylaniline (Table 4, Entry 6)

According to the general procedure B, chlorobenzne (117 mg, 1.04 mmol) reacted with N,N-di-n-butylamine (158 mg, 1.21 mmol) using 0.5 mol % of Pd(OAc)$_2$ and 1.0 mol % of ligand and sodium tert-butoxide (118 mg, 1.20 mmol) at 100° C. for 20 h to give the title compound (200 mg, 94%) as a colorless oil: $^1$H-NMR (300 MHz, CDCl$_3$): δ 7.29 (m, 2H), 6.69–6.75 (m, 3H), 3.35 (t, 4H, J=7.5 and 7.8 Hz), 1.66 (m, 4H), 1.44 (m, 4H), 1.05 (t, 6H, J=7.2 Hz). $^{13}$C{$^1$H}-NMR (100 MHz, CDCl$_3$): δ 148.09, 129.12, 114.98, 111.58, 50.71, 29.35, 20.33, 13.99. GC/MS(EI): m/z 205 (M$^+$), 162, 120, 106, 77.

Example 41

N,N-dibutyl-4-cyanoaniline (Table 4, Entry 7)

According to the general procedure B, 4-chlorobenzonitrile (70 mg, 0.51 mmol) reacted with N,N-di-n-butylamine (77 mg, 0.60 mmol) using 1 mol % Pd(dba)$_2$, 2 mol % of ligand, and K$_3$PO$_4$ (254 mg, 1.20 mmol) at 100° C. in DME solvent to give the title compound (110 mg, 94%) as a colorless oil: $^1$H-NMR (300 MHz, CDCl$_3$): δ 7.43 (d, 2H, J=8.7 Hz), 6.58 (d, 2H, J=9.0 Hz), 3.28 (t, 4H, J=7.5 and 8.1 Hz), 1.58 (m, 4H), 1.36 (m, 4H), 0.97 (t, 6H, J=7.2 Hz). $^{13}$C{$^1$H}-NMR (100 MHz, CDCl$_3$): δ 150.59, 133.52, 120.88, 111.01, 96.20, 50.64, 29.08, 20.20, 13.89. GC/MS (EI): m/z 230 (M$^+$). Anal. Calcd for C$_{15}$H$_{22}$N$_2$: C, 78.21; H, 9.63; N, 12.16. Found: C, 78.22; H, 9.75; N, 12.29.

Example 42

N,N-dibutyl-3-methylaniline (Table 4, Entry 8)

According to the general procedure B, 3-chlorotoluene (127 mg, 1.00 mmol) reacted with N,N-di-n-butylamine (155 mg, 1.20 mmol) using 0.5 mol % Pd(OAc)$_2$, 1 mol % of ligand, and sodium tert-butoxide (115 mg, 1.20 mmol) at 100° C. for 27 h in toluene to give the title compound (208 mg, 94%) as a colorless oil: $^1$H-NMR (300 MHz, CDCl$_3$): δ 7.15 (t, 1H, J=Hz), 6.53 (app.bd, 3H, J=3.3 Hz), 3.31 (t, 4H, J=7.5 Hz), 2.37 (s, 3H), 1.63 (m, 4H), 1.42 (m, 4H), 1.02 (t, 6H, J=7.2 Hz). $^{13}$C{$^1$H}-NMR (100 MHz, CDCl$_3$): δ 148.27, 138.73, 129.02, 116.05, 112.39, 108.94, 50.74, 29.45, 22.02, 20.36, 14.01. GC/MS (EI): m/z 219 (M$^+$). Anal. Calcd for C$_{15}$H$_{25}$N: C, 82.13; H, 11.49; N, 6.38. Found: C. 81.85; H, 11.57; N, 6.47.

Example 43

N-(4-methoxyphenyl)-N-methylaniline (Table 5, Entry 1)

According to the general procedure B, 4-chloroanisole (146 mg, 1.02 mmol) reacted with N-methylaniline (130 mg, 1.20 mmol) using 0.5 mol % Pd(OAc)$_2$, 1 mol % of Ph$_5$FcP(t-Bu)$_2$, and sodium tert-butoxide (115 mg, 1.20 mmol) at 100° C. in toluene to give the title compound (203 mg, 93%) as a colorless oil: $^1$H-NMR (400 MHz, CDCl$_3$): 7.24 (t, 2H, J=7.3 Hz), 7.13 (d, 2H, J=8.79 Hz), 6.93 (d, 2H, J=8.79 Hz), 6.82 (app.d, 3H, J=7.4 Hz), 3.85 (s, 3H), 3.29 (s, 3H). $^{13}$C{$^1$H}-NMR (100 MHz, CDCl$_3$): δ 156.23, 149.68, 142.15, 128.88, 126.21, 118.27, 115.62, 114.71, 55.46, 40.44. GC/MS(EI): m/z 213 (M$^+$). Anal. Calcd for C$_{14}$H$_{15}$NO: C, 78.84; H, 7.09; N, 6.57. Found: C, 78.98; H, 7.12; N, 6.63.

Example 44

N-(o-tolyl)-N-methylaniline (Table 5, Entry 2)

According to the general procedure B, 2-chlorotoluene (129 mg, 1.02 mmol) reacted with N-methylaniline (133 mg, 1.20 mmol) using 0.5 mol % Pd(OAc)$_2$, 1 mol % of Ph$_5$FcP(t-Bu)$_2$, and sodium tert-butoxide (120 mg, 1.25 mmol) in toluene at 100° C. to give the title compound (180 mg, 89%) as a colorless oil: $^1$H-NMR (400 MHz, CDCl$_3$): δ 7.37–7.21 (m, 6H), 6.78 (t, 1H, J=7.25 Hz), 6.61 (d, 2H, J=7.86 Hz), 3.30 (s, 3H), 2.22 (s, 3H). $^{13}$C{$^1$H}-NMR (100 MHz, CDCl$_3$): δ 149.08, 146.74, 136.80, 131.32, 128.93, 128.30, 127.46, 126.38, 116.72, 112.76, 39.00, 17.83. GC/MS(EI): m/z 197 (M$^+$). Anal. Calcd for C$_{14}$H$_{15}$N: C, 85.24; H, 7.66; N, 7.10. Found: C, 85.09; H, 7.71; N, 7.24.

Example 45

N-(4-cyanophenyl)-N-methylaniline (Table 5, Entry 3)

According to the general procedure B, 4-chlorobenzonitrile (74 mg, 0.50 mmol) reacted with N-methylaniline (64 mg, 0.60 mmol) using 1 mol % of Pd(dba)$_2$, 2 mol % of Ph$_5$FcP(t-Bu)$_2$, and sodium tert-butoxide (58 mg, 0.60 mmol) in toluene at 45° C. to give the title compound (102 mg, 91%): $^1$H-NMR(400 MHz, CDCl$_3$): δ 7.47–7.39 (m, 4H), 7.28 (t, 1H), 7.21 (d, 2H), 6.74 (d, 2H, J=9.0 Hz), 3.36 (s, 3H). $^{13}$C{$^1$H}-NMR (100 MHz, CDCl$_3$): δ. GC/MS(EI): m/z 208 (M$^+$), 192.

Example 46

N-(4-tert-butylphenyl)-N-methylaniline (Table 5, Entry 4)

According to general procedure B, 4-tert-butylbromobenzene (117 mg, 0.55 mmol) reacted with N-methylaniline (54 mg, 0.50 mmol) using 1 mol % of Pd(dba)$_2$, 2 mol % of Ph$_5$FcP(t-Bu)$_2$, and sodium tert-butoxide (58 mg, 0.60 mmol) in toluene at 100° C. for 2 h to give the title compound (117 mg, 98%): $^1$H-NMR (300 MHz, CDCl$_3$): δ 7.36 (t, 2H, J=8.1 Hz), 7.29 (t, 2H, J=7.5 and 7.8 Hz), 7.04 (dd, 4H, J=8.1 Hz), 6.94 (t, 1H, J=7.2 Hz and 7.5 Hz), 3.34 (s, 3H), 1.38 (s, 9H). $^{13}$C{$^1$H}-NMR (100 MHz, CDCl$_3$): δ 149.17, 146.36, 144.77, 129.02, 126.05, 121.23, 120.18, 118.94, 40.20, 34.18, 31.45. GC/MS(EI): m/z 239 (M$^+$), 224

Example 47

4-methoxy-diphenylamine (Table 6, Entry 1)

According to the general procedure B, 4-chloroanisole (72 mg, 0.50 mmol) reacted with aniline (47 mg, 0.50 mmol) using 1 mol % of Pd(dba)$_2$, 2 mol % of Ph$_5$FcP(t-Bu)$_2$, and sodium tert-butoxide (59 mg, 0.60 mmol) in toluene at 70° C. to give the title compound (96 mg, 95%): $^1$H-NMR (300 MHz, CDCl$_3$): δ 7.26 (t, 2H, J=8.4 and 7.5 Hz), 7.12 (d, 2H, J=8.7 Hz), 6.86–6.97 (m, 5H), 5.55 (bs, 1H, —NH—), 3.84 (s, 3H). $^{13}$C{$^1$H}-NMR (100 MHz, CDCl$_3$): δ GC/MS(EI): m/z 199 (M$^+$).

Example 48

2-methyl-diphenylamine (Table 6, Entry 2)

According to the general procedure B, 2-chlorotoluene (65 mg, 0.51 mmol) reacted with aniline (48 mg, 0.52 mmol) using 1 mol % of Pd(dba)$_2$, 2 mol % of Ph$_5$FcP(t-Bu)$_2$, and sodium tert-butoxide (60 mg, 0.60 mmol) in toluene at 70° C. to give the title compound (92 mg, 97%) as an oil: $^1$H-NMR (300 MHz, CDCl$_3$): δ 7.19–7.27 (m, 4H, Ar—H), 7.14 (dd, 1H, J=7.2 and 7.6 Hz), 6.97–6.88 (m, 4H), 5.36 (bs, 1H, —NH—), 2.25 (s, 3H, Ar—CH$_3$). $^{13}$C{$^1$H}-NMR (100 MHz, CDCl$_3$): δ 143.86, 141.13, 130.88, 129.25, 128.19, 126.69, 121.89, 120.40, 118.65, 117.37, 17.87. GC/MS(EI): m/z 183 (M$^+$).

Example 49

4-cyanodiphenylamine (Table 6, Entry 3)

According to the general procedure B, 4-chlorobenzonitrile (138 mg, 1.00 mmol) reacted with aniline (112 mg, 1.20 mmol) using 0.5 mol % of Pd(dba)$_2$, 2 mol % of Ph$_5$FcP(t-Bu)$_2$, and K$_3$PO$_4$ (640 mg, 3.00 mmol) in DME at 100° C. to give the title compound (190 mg, 97%) as a white solid: $^1$H-NMR (400 MHz, CDCl$_3$): δ 7.47 (d, 2H, J=8.4 Hz), 7.37 (t, , J=7.6 and 8.4 Hz), 7.18 (d, 2H, J=8.4 Hz), 7.13 (t, , J=7.2 Hz), 6.99 (d, , J=8.4 Hz), 6.28 (bs, 1H). $^{13}$C{$^1$H}-NMR (100 MHz, CDCl$_3$): δ 147.99, 139.92, 133.64, 129.51, 123.77, 121.05, 119.96, 114.77, 101.05. GC/MS(EI): m/z 194 (M$^+$).

Example 50

Diphenylamine (Table 6, Entries 4 and 5)

According to general procedure B, chlorobenzene (57 mg, 0.50 mmol) reacted with aniline (48 mg, 0.50 mmol) using 1 mol % of Pd(dba)$_2$, 2 mol % of Ph$_5$FcP(t-Bu)$_2$, and sodium tert-butoxide (59 mg, 0.60 mmol) in toluene at 70° C. to give the title compound (73 mg, 86%) as a white solid. The coupling reaction of bromobenzene (158 mg, 1.00 mmol) with aniline (93 mg, 1.00mmol) occurred at room temperature over 4 h using 1 mol % of Pd(dba)$_2$/Ph$_5$FcP(t-Bu)$_2$ to give the title compound (166 mg, 98%): $^1$H-NMR (400 MHz, CDCl$_3$): δ 7.34 (t, 4H, J=7.8 Hz and 7.5 Hz), 7.14 (d, 4H, J=8.7 Hz), 7.00 (t, 2H, J=7.2 and 7.5 Hz), 5.74 (bs, 1H). $^{13}$C{$^1$H}-NMR (100 MHz, CDCl$_3$): δ 143.09, 129.32, 120.97, 117.78. GC/MS(EI): m/z 169 (M$^+$).

Example 51

N-n-hexyl-4-methoxyaniline (Table 7, Entry 1)

According to the general procedure B, 4-chloroanisole (72 mg, 0.50 mmol) reacted with n-hexylamine (80 μl, 0.60 mmol) using 2 mol % of Pd(OAc)$_2$, 4 mol % of Ph$_5$FcP(t-Bu)$_2$, and sodium tert-butoxide (59 mg, 0.60 mmol) in toluene at 70° C. for 8 h to give the title compound (96 mg, 92% as a colorless oil: $^1$H-NMR (400 MHz, CDCl$_3$): δ 6.79 (d, 2H, J=8.0 Hz), 6.60 (d, 2H, J=8.0 Hz), 3.76 (s, 3H, ArOMe), 3.07 (t, 2H, J=6.8 Hz), 1.61 (m, 2H), 1.39 (m, 2H), 1.33 (m, 2H), 0.91 (t, 3H, J=6.4 and 6.8 Hz). $^{13}$C{$^1$H}-NMR (100 MHz, CDCl$_3$): δ 151.92, 142.77, 114.83, 114.02, 55.80, 45.04, 31.66, 29.61, 26.87, 22.62, 14.05. GC/MS(EI): m/z 207 (M$^+$), 136. Anal. Calcd for C$_{13}$H$_{21}$NO: C, 75.32; H, 10.21; N, 6.76. Found: C, 75.56; H, 10.37; N, 6.78.

Example 52

N-n-hexyl-2-methylaniline (Table 7, Entries 2 and 3)

According to the general procedure B, 2-chlorotoluene (73 mg, 0.58 mmol) reacted with n-hexylamine (80 μl, 0.61 mmol) using 1 mol % of Pd(dba)$_2$, 2 mol % of Ph$_5$FcP(t-Bu)$_2$, and sodium tert-butoxide (59 mg, 0.60 mmol) in toluene at 70° C. for 8 h to give the title compound (102 mg, 92%) as a colorless oil: $^1$H-NMR (300 MHz, CDCl$_3$): δ 7.20 (t, 1H, J=7.5 and 7.8 Hz), 7.12 (d, 1H, J=7.2 Hz), 6.70 (dd, 2H, J=7.5 Hz), 3.51 (bs, 1H), 3.22 (t, 2H, J=7.2 Hz), 2.21 (s, 3H), 1.74 (m, 2H), 1.48 (m, 2H), 1.41 (m, 2H). $^{13}$C{$^1$H}-NMR (100 MHz, CDCl$_3$): δ 146.35, 129.94, 127.08, 121.60, 116.53, 109.52, 43.91, 31.64, 29.54, 26.90, 22.62, 17.43, 14.03. GC/MS(EI): m/z 191 (M$^+$), 121. Anal. Calcd for C$_{13}$H$_{21}$N: C, 81.62; H, 11.06; N, 7.32. Found: C, 81.52; H, 11.09; N, 7.37.

Example 53

N-n-hexyl-4-cyanoaniline (Table 7, Entry 4)

According to the general procedure B, 4-Chlorobenzonitrile (69 mg, 0.50 mmol) reacted with n-hexylamine (80 μl, 0.60 mmol) using 1 mol % of Pd(dba)$_2$, 2 mol % of Ph$_5$FcP(t-Bu)$_2$, and sodium tert-butoxide (58 mg, 0.60 mmol) in toluene at 70° C. for 8 h to give the title compound as a solid (79 mg, 78%). On the other hand, the reaction of 4-chlorobenzonitrile (69 mg, 0.50 mmol) with n-hexylamine (61 mg, 0.60) using K$_3$PO$_4$ and DME also occurred in 92% yield to afford the title compound (93 mg) at 100° C. for 13 h. $^1$H-NMR (300 MHz, CDCl$_3$): δ 7.39 (d, 2H, J=8.4 Hz), 6.54 (d, 2H, J=8.7 Hz), 4.34 (bs, 1H, —NH—), 3.13 (t, 2H, J=6.9 and 7.2 Hz). $^{13}$C{$^1$H}-NMR (100 MHz, CDCl$_3$): δ 151.43, 133.47, 120.60, 111.56, 97.69, 43.03, 31.37, 28.89, 26.55, 22.43, 13.88. GC/MS(EI): m/z 202 (M$^+$).

Example 54

N-n-hexyl-4-phenylcarbonylaniline (Table 7, Entry 5)

According to the general procedure B, 4-Bromobenzophenone (131 mg, 0.50 mmol) reacted with n-hexylamine (52 mg, 0.52 mmol) using 1 mol % of Pd(dba)$_2$, 2 mol % of Ph$_5$FcP(t-Bu)$_2$, and sodium tert-butoxide (58 mg, 0.60 mmol) in toluene at 50° C. for 13 h to give the title compound (134 mg, 93%) as a solid: $^1$H-NMR (300 MHz, CDCl$_3$): δ 7.74, (t, 4H, J=8.4 Hz), 7.53–7.43 (m, 3H), 6.58 (d, 2H, J=8.7 Hz), 4.46 (bs, 1H), 3.17 (t, 2H, J=6.6 Hz), 1.61 (m, 2H), 1.42–1.32 (m, 6H), 0.91 (t, 3H, J=6.6 Hz). $^{13}$C{$^1$H}-NMR (100 MHz, CDCl$_3$): δ 195.00, 152.27, 139.11, 132.93, 131.00, 129.30, 127.89, 125.42, 111.02, 43.17, 31.44, 29.09. GC/MS(EI): m/z 281 (M$^+$).

Example 55

N-n-hexyl-4-tert-butylaniline (Table 7, Entry 6)

According to the general procedure B, 4-tert-butylbromobenzene (108 mg, 0.51 mmol) reacted with n-hexylamine (80 μl, 0.60 mmol) using 1 mol % of Pd(OAc)$_2$, 2 mol % of Ph$_5$FcP(t-Bu)$_2$, and sodium tert-butoxide (59 mg, 0.60 mmol) in THF at 80° C. for 2 h to give the title compound (110 mg, 94%) as a colorless oil: $^1$H-NMR (300 MHz, CDCl$_3$): δ 7.26 (d, 2H, J=8.4 Hz), 6.62 (d, 2H, J=8.4 Hz), 3.51 (bs, 1H), 3.14 (t, 2H, J=7.2 Hz), 1.66 (m, 2H), 1.34–1.43 (m, 6H), 1.34 (s, 9H, t-Bu), 0.96 (t, 3H, J=6.3 and 6.9 Hz). $^{13}$C{$^1$H}-NMR (100 MHz, CDCl$_3$): δ 146.14, 139.75, 125.92, 112.35, 44.11, 33.76, 31.63, 31.53, 29.58, 26.86, 22.62, 14.05. GC/MS(EI): m/z 233 (M$^+$). Anal. Calcd for C$_{16}$H$_{27}$N: C, 82.34; H, 11.82; N, 6.00. Found: C,82.55; H, 11.82; N, 6.06.

Example 56

N-n-hexyl-2-methoxyaniline (Table 7, Entry 11)

According to the general procedure B, 2-Chloroanisole (72 mg, 0.51 mmol) reacted with n-hexylamine (80 μl, 0.60 mmol) using 1 mol % of Pd(OAc)$_2$, 2 mol % of Ph$_5$FcP(t-Bu)$_2$, and sodium tert-butoxide (58 mg, 0.60 mmol) in toluene at 100° C. to give the title compound (102 mg, 97%) as a colorless oil: $^1$H-NMR (400 MHz, CDCl$_3$): δ 6.93 (t, 1H, J=8.0 Hz, aryl coupling J=0.9 Hz), 6.82 (d, 1H, J=8.0 Hz), 6.66–6.73 (m, 2H), 4.30 (bs, 1H), 3.89 (s, 3H), 3.17 (t, 2H, J=7.2 Hz), 1.71 (m, 2H), 1.51–1.34 (m, 6H), 0.97 (t, 3H, J=6.4 and 6.8 Hz). $^{13}$C{$^1$H}-NMR (100 MHz, CDCl$_3$): δ 146.65, 138.39, 121.23, 116.03, 109.71, 109.24, 55.29, 43.63, 31.63, 29.43, 26.88, 22.58, 14.00. GC/MS(EI): m/z 207 (M$^+$). Anal. Calcd for C$_{13}$H$_{21}$NO: C, 75.23; H, 10.21; N, 6.76. Found: C,75.41; H, 10.25; N, 6.69.

Example 57

N-n-hexyl-3-methoxyaniline(Table 7, Entries 7 and 8)

3-Chloroanisole (74 mg, 0.52 mmol) reacted with n-hexylamine (65 mg, 0.64 mmol) according to procedure B using 1 mol % of Pd(dba)$_2$, 2 mol % of Ph$_5$FcP(t-Bu)$_2$, and sodium tert-butoxide (58 mg, 0.60 mmol) in toluene at 100° C. to give the title compound (103 mg, 95%) as a colorless oil. Also 3-bromoanisole was converted to the title amine in 85% yield by procedure A: $^1$H-NMR (400 MHz, CDCl$_3$): δ 6.99 (t, 1H, J=8.0 Hz), 6.19–6.13 (m, 2H), 6.08 (app.t, 1H, J=2.4 Hz), 3.70 (s, 3H), 3.55 (bs, 1H), 3.01 (t, 2H, J=7.2 Hz), 1.53 (m, 2H), 1.33 (m, 2H), 1.24 (m, 4H), 0.83 (t, 3H, J=6.8 Hz). $^{13}$C{$^1$H}-NMR (100 MHz, CDCl$_3$): δ 160.81, 149.91, 129.87, 105.86, 102.09, 98.53, 55.01, 43.95, 31.61, 29.47, 26.81, 22.60, 14.01. GC/MS(EI): m/z 207 (M$^+$), 136. Anal. Calcd for C$_{13}$H$_{21}$NO: C, 75.23; H, 10.21; N, 6.76. Found: C,75.25; H, 10.33; N, 6.86.

Example 58

N-n-hexyl-2,5-dimethylaniline (Table 7, Entry 9)

According to the general procedure B, 2-Chloro-p-xylene (73 mg, 0.52 mmol) reacted with n-hexylamine (62 mg, 0.61 mmol) using 1 mol % of Pd(dba)$_2$, 2 mol % of Ph$_5$FcP(t-Bu)$_2$, and sodium tert-butoxide (60 mg, 0.63 mmol) in toluene at 100° C. for 10 h to give the title compound (90 mg, 87%) as a colorless oil: $^1$H-NMR (400 MHz, CDCl$_3$): δ 7.00 (d, 1H, J=7.2 Hz), 6.54 (d, 1H, J=7.6 Hz), 6.51 (s, 1H), 3.45 (bs, 1H), 3.20 (dd, 2H, J=6.8 and 7.2 Hz), 2.37 (s, 3H), 2.16 (s, 3H), 1.73 (m, 2H), 1.49 (m, 2H), 1.41 (m, 4H), 0.99 (t, 1H, J=6.8 and 7.2 Hz). $^{13}$C{$^1$H}-NMR (100 MHz, CDCl$_3$): δ 146.23, 136.65, 129.77, 118.61, 117.14, 110.46, 43.92, 31.63, 29.56, 26.90, 22.63, 21.54, 16.98, 14.03. GC/MS(EI): m/z 205 (M$^+$).

Example 59

N-(2,6-dimethylphenyl)-n-hexylamine (Table 7, Entry 10)

According to the general procedure B, 2-Chloro-m-xylene (70 mg, 0.50 mmol) reacted with n-hexylamine (80 μl, 0.60 mmol) using 2 mol % of Pd(OAc)$_2$, 4 mol % of Ph$_5$FcP(t-Bu)$_2$, and sodium tert-butoxide (58 mg, 0.60 mmol) in toluene (1.5 ml) at 100° C. to give the title compound (100 mg, 97%) as a colorless oil: $^1$H-NMR (400 MHz, CDCl$_3$): δ 7.02 (d, 2H, J=7.2 Hz), 6.83 (t, 1H, J=7.2 Hz), 3.00 (t, 2H, J=7.2 and 7.6 Hz), 3.0 (bs, 1H), 2.32 (s, 6H), 1.61 (m, 2H), 1.45–1.31 (m, 6H), 0.93 (t, 3H, J=5.6 and 7.2 Hz). $^{13}$C{$^1$H}-NMR (100 MHz, CDCl$_3$): δ 146.37, 129.05, 128.75, 121.52, 48.69, 31.73, 31.14, 26.83, 22.62, 18.54, 14.03. GC/MS(EI): m/z 205 (M$^+$).

Example 60

N,N-di(4-tert-butylphenyl)-n-hexylamine (Table 7, Entry 12)

According to the general procedure B, 4-tert-butylbromobenzene (214 mg, 1.00 mmol) reacted with n-hexylamine (66 μl, 0.50 mmol) using 1 mol % of Pd(OAc)$_2$, 2 mol % of Ph$_5$FcP(t-Bu)$_2$, and sodium tert-butoxide (116 mg, 1.21 mmol) in toluene at 100° C. for 4 h to give the title compound (182 mg, 99%) as an oil: $^1$H-NMR (400 MHz, CDCl$_3$): δ 7.17 (d, 4H, J=8.4Hz), 6.82 (d, 4H, J=8.8 Hz), 3.55 (t, 2H, J=7.2 and 8.0 Hz), 1.57 (m, 2H), 1.22 (s, 18H), 0.79 (t, 3H, J=6.4 and 6.8 Hz). $^{13}$C{$^1$H}-NMR (100 MHz, CDCl$_3$): δ 145.68, 143.41, 125.93, 120.20, 52.38, 34.06, 31.67, 31.49, 27.55, 26.78, 22.70, 14.05. GC/MS(EI): m/z 365 (M$^+$). Anal. Calcd for C$_{26}$H$_{39}$N: C, 85.42; H, 10.75; N, 3.83. Found: C,85.22; H, 10.82; N, 3.86.

Example 61

2-(3-(N-n-hexyl)aminophenyl)-1,3-dioxolane

According to the general procedure B, 2-(3-bromophenyl)-1,3-dioxolane (115 mg, 0.50 mmol) reacted with n-hexylamine (80 μl, 0.60 mmol) using 1 mol % of Pd(dba)$_2$, 2 mol % of Ph$_5$FcP(t-Bu)$_2$, and sodium tert-butoxide (58 mg, 0.60 mmol) in toluene at 100° C. to give the title compound (118 mg, 94%) as a colorless oil: $^1$H-NMR (300 MHz, CDCl$_3$): δ 7.19 (t, 1H, J=7.8 Hz), 6.81 (d, 1H, J=6.9 Hz), 6.74 (s, 1H), 6.61 (m, 1H), 5.77 (s, 1H), 4.13 (m, 2H), 4.03 (m, 2H), 3.55 (bs, 1H), 3.13 (t, 2H, J=6.9 and 7.2 Hz), 1.62 (m, 2H), 1.45–1.33 (m, 6H), 0.92 (t, 3H, J=6.0 and 6.9 Hz). $^{13}$C{$^1$H}-NMR (100 MHz, CDCl$_3$): δ

148.53, 138.85, 129.21, 115.07, 113.48, 110.31, 103.88, 65.15, 43.98, 31.58, 29.43, 26.78, 22.59, 14.01. GC/MS (EI): m/z 249 (M$^+$). Anal. Calcd for $C_{15}H_{23}NO_2$: C, 72.25; H, 9.30; N, 5.62. Found: C, 72.19; H, 9.43; N, 5.70.

Example 62

N-(4-methoxyphenyl)benzylamine (Table 8, Entry 1)

According to the general procedure A, 4-chloroanisole (73 mg, 0.51 mmol) reacted with benzylamine (68 mg, 0.63 mmol) using 1 mol % of Pd(dba)$_2$, 2 mol % of Ph$_5$FcP(t-Bu)$_2$, and sodium tert-butoxide (60 mg, 0.63 mmol) in toluene at 100° C. for 4 h to give the title compound (100 mg, 93%) as a solid: $^1$H-NMR (500 MHz, CDCl$_3$): δ 6.63 (d, 2H, J=8.84 Hz), 6.81 (d, 2H, J=8.83 Hz), 7.41–7.35 (m, 4H), 7.30 (t, 1H, J=7.08 and 7.03 Hz), 4.31 (s, 2H), 3.77 (s, 3H). $^{13}$C{$^1$H}-NMR (125 MHz, CDCl$_3$): δ 152.18, 142.42, 139.66, 128.56, 127.52, 127.14, 114.89, 114.09, 55.78, 49.23. GC/MS(EI): m/z 213 (M$^+$).

Example 63

N-(4-methylphenyl)benzylamine (Table 8, Entry 2)

According to the general procedure A, 4-chlorotoluene (128 mg, 1.01 mmol) reacted with benzylamine (128 mg, 1.19 mmol) using 1 mol % of Pd(OAc)$_2$, 2 mol % of Ph$_5$FcP(t-Bu)$_2$, and sodium tert-butoxide (122 mg, 1.27 mmol) in toluene at 100° C. to give the title compound (189 mg, 95%) as a colorless oil: $^1$H-NMR (400 MHz, CDCl$_3$): δ 7.43–7.38 (m, 4H), 7.34–7.30 (m, 1H), 7.04 (d, 2H, J=8.26 Hz), 6.61 (d, 2H, J=8.37 Hz), 4.35 (s, 2H), 3.95 (bs, 1H), 2.29 (s, 3H). $^{13}$C{$^1$H}-NMR (100 MHz, CDCl$_3$): δ 145.85, 139.59, 129.70, 128.55, 127.45, 127.10, 126.68, 112.93, 48.56, 20.37. GC/MS(EI): m/z 197 (M$^+$). Anal. Calcd for $C_{14}H_{15}N$. C, 85.24; H, 7.66; N, 7.10. Found C, 85.29; H, 7.68; N, 7.14.

Example 64

N-(4-cyanophenyl)benzylamine (Table 8, Entry 3)

According to the general procedure A, 4-chlorobenzonitrile (69 mg, 0.50 mmol) reacted with benzylamine (54 mg, 0.50 mmol) using 1 mol % of Pd(dba)$_2$, 2 mol % of Ph$_5$FcP(t-Bu)$_2$, and sodium tert-butoxide (58 mg, 0.60 mmol) in toluene at 50° C. for 24 h to give the title compound (81 mg, 76%) as a solid: $^1$H-NMR (300 MHz, CDCl$_3$): δ 7.41 (d, 2H, J=8.7 Hz), 7.36 (m, 5H), 6.61 (d, 2H, J=8.4 Hz), 4.73 (bs, 1H), 4.39 (d, 2H, J=5.4 Hz). $^{13}$C{$^1$H}-NMR (100 MHz, CDCl$_3$): δ 151.05, 137.76, 133.67, 128.82, 127.64, 127.26, 120.36, 112.36, 98.99, 47.42. GC/MS(E): m/z 208 (M$^+$), 209.

Example 65

N-phenylbenzylamine (Table 8, Entry 4)

According to the general procedure A, chlorobenzene (58 mg, 0.51 mmol) reacted with benzylamine (68 mg, 0.64 mmol) using 1 mol % of Pd(dba)$_2$, 2 mol % of Ph$_5$FcP(t-Bu)$_2$, and sodium tert-butoxide (59 mg, 0.60 mmol) in toluene at 100° C. for 5 h to give the title compound (85 mg, 92%) as an oil. GC/MS(EI): m/z 183 (M$^+$), 184.

Example 66

N-(o-tolyl)benzylamine (Table 8, Entry 5)

According to the general procedure A, 2-chlorotoluene (66 mg, 0.52 mmol) reacted with benzylamine (68 mg, 0.64 mmol) using 1 mol % of Pd(dba)$_2$, 2 mol % of Ph$_5$FcP(t-Bu)$_2$, and sodium tert-butoxide (60 mg, 0.63 mmol) in toluene at 100° C. for 4 h to give the title compound (99 mg, 96%) as a solid after recrystallization from hexane: $^1$H-NMR (300 MHz, CDCl$_3$): δ 7.48–7.35 (m, 5H), 7.14 (m, 2H), 6.75 (t, 1H, J=7.2 and 7.5 Hz), 6.68 (d, 1H, J=7.8 Hz), 4.44 (s, 2H), 3.93 (bs, 1H), 2.24 (s, 3H). $^{13}$C{$^1$H}-NMR (100 MHz, CDCl$_3$): δ 146.01, 139.46, 130.02, 128.62, 127.50, 127.20, 127.12, 121.86, 117.13, 109.93, 48.26, 17.52. GC/MS(EI): m/z 197 (M$^+$), 120, 106. Anal. Calcd for $C_{14}H_{15}N$: C, 85.24; H, 7.66; N, 7.10. Found: C, 84.98; H, 7.64; N, 7.20.

Example 67

N-(4-methoxycarbonylphenyl)-n-hexylamine (Table 9, Entry 1)

According to the general procedure B, Methyl 4-chlorobenzoate (85 mg, 0.50 mmol) reacted with n-hexylamine (80 μl, 0.60 mmol) using 2 mol % of Pd(dba)$_2$, 4 mol % of Ph$_5$FcP(t-Bu)$_2$, K$_3$PO$_4$ (260 mg, 1.23 mmol) in toluene at 100° C. for 20 h to give the title compound (101 mg, 86%) as a solid: $^1$H-NMR (500 MHz, CDCl$_3$): δ 7.90 (d, 2H, J=8.8 Hz), 6.54 (d, 2H, J=8.8 Hz), 4.17 (bs, 1H), 3.85 (s, 3H, —COOMe), 3.15 (dd, 2H, J=7.0 and 12.3 Hz), 1.62 (m, 2H), 1.40 (m, 2H), 1.32 (m, 2H), 0.91 (t, 3H, J=6.9 Hz). $^{13}$C{$^1$H}-NMR (100 MHz, CDCl$_3$): δ 167.31, 152.13, 131.47, 117.85, 111.22, 51.38, 43.30, 31.50, 29.21, 26.68, 22.52, 13.94. GC/MS(EI): m/z 235 (M$^+$), 164. Anal. Calcd for $C_{14}H_{21}NO_2$: C, 71.46; H, 8.99; N, 5.95. Found: C, 71.54; H, 8.84; N, 5.79.

Example 68

4-methoxycarbonylphenyl-diphenylamine (Table 9, Entry 3)

According to the general procedure A, methyl 4-chlorobenzoate (88 mg, 0.52 mmol) reacted with aniline (57 mg, 0.61 mmol) using 1 mol % of Pd(dba)$_2$, 2 mol % of Ph$_5$FcP(t-Bu)$_2$, and K$_3$PO$_4$ (260 mg, 1.23 mmol) in DME at 100° C. for 24 h to give the title compound (111 mg, 96%) as a solid: $^1$H-NMR (400 MHz, CDCl$_3$): δ 7.94 (d, 2H, J=7.6 Hz), 7.35 (t, 2H, J=6.0 and 7.6 Hz), 7.19 (d, 2H, J=7.6 Hz), 7.08 (t, 1H, J=7.6 Hz), 7.01 (d, 2H, J=8.8 Hz), 6.27 (bs, 1H), 3.89 (s, 3H). $^{13}$C{$^1$H}-NMR (100 MHz, CDCl$_3$): δ 166.97, 148.06, 140.75, 131.36, 129.37, 122.91, 120.74, 120.27, 114.41, 51.65. GC/MS(EI): m/z 227 (M$^+$).

Example 69

N-(4-methoxycarbonylphenyl)-N-methylaniline (Table 9, Entry 2)

According to the general procedure B, methyl 4-chlorobenzoate (172 mg, 1.00 mmol) reacted with N-methylaniline (130 mg, 1.20 mmol) using 1 mol % of Pd(OAc)$_2$, 2 mol % of Ph$_5$FcP(t-Bu)$_2$, and K$_3$PO$_4$ (640 mg, 3.02 mmol) in DME at 100° C for 20 h to give the title compound (240 mg, 97%) as a solid: $^1$H-NMR (500 MHz, CDCl$_3$): δ 7.89 (d, 2H, J=9.05 Hz), 7.41 (t, 2H, J=7.68 and 8.17 Hz), 7.24–7.21 (m, 3H), 6.79 (d, 2H, J=9.06 Hz), 3.88 (s, 3H), 3.37 (s, 3H). $^{13}$C{$^1$H}-NMR (125 MHz, CDCl$_3$): δ 167.09, 152.44, 147.41, 130.91, 129.70, 125.50, 125.24, 119.08, 113.70, 51.47, 40.09. GC/MS(EI): m/z 241 (M$^+$). Anal. Calcd for $C_{15}H_{15}NO_2$: C, 74.67; H, 6.27; N, 5.81. Found: C, 74.74; H, 6.34; N, 5.80.

Example 70

4-nitro-diphenylamine (Table 9, Entry 6)

According to the general procedure B, 4-chloronitrobenzene (80 mg, 0.51 mmol) reacted with aniline (57 mg, 0.60 mmol) using 1 mol % of Pd(dba)$_2$, 2 mol % of Ph$_5$FcP(t-Bu)$_2$, and K$_3$PO$_4$ (254 mg, 1.21 mmol) in DME at 100° C. to give the title compound (102 mg, 95%) as a yellow solid: $^1$H-NMR (400 MHz, CDCl$_3$): δ 8.12 (d, 2H, J=7.2 Hz), 7.40 (t, 2H, J=7.2 and 8.8 Hz), 6.96 (d, 2H, J=7.2 Hz), 7.24–7.18 (m, 3H), 6.48 (bs, 1H). $^{13}$C{$^1$H}-NMR (125 MHz, CDCl$_3$): δ 150.26, 139.51, 139.44, 129.64, 126.18, 124.54, 121.83, 113.59. GC/MS(EI): m/z 214 (M$^+$). Anal. Calcd for C$_{12}$H$_{10}$N$_2$O$_2$: C, 67.28; H, 4.71; N, 13.08. Found: C, 67.45; H, 4.75; N, 13.02.

Example 71

4-nitrophenylmorpholine (Table 9, Entry 5)

According to the general procedure B, 4-chloronitrobenzene (80 mg, 0.51 mmol) reacted with morpholine (53 mg, 0.60 mmol) using 1 mol % of Pd(dba)$_2$, 2 mol % of Ph$_5$FcP(t-Bu)$_2$, and K$_3$PO$_4$ (256 mg, 1.21 mmol) in DME at 100° C. to give the title compound (58 mg, 56%) as a yellow solid: $^1$H-NMR (400 MHz, CDCl$_3$): δ 8.11 (d, 2H, J=9.6 Hz), 6.82 (d, 2H, J=9.6 Hz), 3.85 (t, 4H, J=5.2 Hz), 3.37 (t, 4H, J=5.2 Hz). $^{13}$C{$^1$H}-NMR (125 MHz, CDCl$_3$): δ 154.91, 138.80, 125.76, 112.50, 66.26, 47.00. GC/MS(EI): m/z 208 (M$^+$).

Example 72

N,N-di-n-butyl(4-methoxycarbonyl)aniline (Table 9, Entry 4)

According to the general procedure A, methyl 4-chlorobenzoate (86 mg, 0.50 mmol) reacted with di-n-butylamine (77 mg, 0.60 mmol) using 1 mol % of Pd(dba)$_2$, 2 mol % of Ph$_5$FcP(t-Bu)$_2$, and K$_3$PO$_4$ (255 mg, 1.20 mmol) in DME at 100° C. to give the title compound (128 mg, 96%) as an oil: $^1$H-NMR (400 MHz, CDCl$_3$): δ 7.87 (d, 2H, J=8.8 Hz), 6.58 (d, 2H, J=8.8 Hz), 3.85 (s, 3H), 3.32 (t, 4H, J=7.6 and 8.0 Hz), 1.60 (m, 4H), 1.37 (m, 4H), 0.97 (t, 6H, J=7.2 and 7.6 Hz). $^{13}$C{$^1$H}-NMR (100 MHz, CDCl$_3$): δ 167.40, 151.26, 131.36, 115.78, 110.13, 51.33, 50.63, 29.20, 20.20, 13.91. GC/MS(EI): m/z 232 (M$^+$-OMe), 220 (M$^+$-propyl), 178. Anal. Calcd for C$_{16}$H$_{25}$NO$_2$: C, 72.96; H, 9.57; N, 5.32. Found: C, 73.06; H, 9.44; N, 5.35.

C. Reactions of Aryl Halides and Boronic Acids

The method of the invention may also be practiced with various aryl halides and boronic acid compounds using Suzuki coupling procedures. The aryl halides employed in this embodiment of the invention may include aryl halides that are electron deficient, electron rich, or electron neutral. In addition, the boronic acid compounds may be aromatic or aliphatic.

General Procedure A

A 4 ml vial was charged with 4-bromobenzophenone (268 mg, 1.03 mmol), o-tolylboronic acid (152 mg, 1.12 mmol), KF (116 mg, 2.00 mmol), Pd(dba)$_2$ (5.8 mg, 1 mol %), and Ph$_5$FcP(t-Bu)$_2$ (7.1 mg, 2 mol %). Anhydrous toluene (2 ml) was added to the mixture, and the vial was sealed with a cap containing PTFE septum and removed from the drybox. The reaction solution was stirred at room temperature for 18 h. After the starting aryl halide was consumed, the reaction solution was directly absorbed onto silica gel and the coupling product was isolated by eluting with hexane/ethyl acetate to give 275 mg (98%) of 4-(2-methylphenyl) benzophenone as a solid:

General Procedure B

A 4 mL vial was charged with 4-tert-butylbromobenzene (213 mg, 1.00 mmol), Pd(dba)$_2$ (5.8 mg, 0.01 mmol, 1 mol %), Ph$_5$FcP(t-Bu)$_2$ (14.2 mg, 0.02 mmol, 2 mol %), K$_3$PO$_4$ (430 mg, 2.02 mmol, powdered) and n-butylboronic acid (124 mg, 1.21 mmol). Anhydrous toluene (2 mL) and a stirring bar were added, and the vial was then sealed with a cap containing a PTFE septum and removed from the drybox. The reaction mixture was stirred at 100° C. for 2.5 h. After the starting aryl halide was consumed as determined by GC, the reaction solution was cooled to room temperature. The reaction solution was then adsorbed onto silica gel directly, and the product was isolated by eluting with ethyl acetate/hexanes to give 175 mg (92%) of 4-tert-butyl-1-n-butylbenzene as colorless oil. Kugelrohl distillation was used for further purification.

General Procedure C

A 4 ml vial was charged with 4-tert-butylbromobenzene (1.00 mmol), Pd(dba)$_2$ (0.01 mmol, 1 mol %), Ph$_5$FcP(t-Bu)$_2$ (0.02 mmol, 2 mol %), KF (2.02 mmol, powdered) and n-butylboronic acid (1.21 mmol). Anhydrous THF (2 ml) and a stirring bar were added, and the vial was sealed with a cap containing a PTFE septum and removed from the drybox. The reaction mixture was stirred at room temperature for 18 h. After a starting aryl halide was consumed as determined by GC, the reaction solution was cooled to room temperature. Then the reaction solution was adsorbed onto silica gel directly, and the product was isolated by eluting with ethyl acetate/hexanes to give 220 mg (98%) of 4-tert-butyl-1-n-butylbenzene as a colorless oil. Kugelrohl distillation was used for further purification.

TABLE 10

Suzuki Coupling Reaction of Electron Deficient Aryl Bromides using by Pd/Ph$_5$FcP(t-Bu)$_2$ catalyst at room temperature.

| Entry | Halide | Boronic Acid | Product | Condition[a] | Yield (%)[b] |
|---|---|---|---|---|---|
| 1 | PhOC—C$_6$H$_4$—Br | 2-CH$_3$-C$_6$H$_4$-B(OH)$_2$ | PhOC—C$_6$H$_4$—C$_6$H$_4$-CH$_3$ | 1 mol % (Pd/L) KF(2)/Toln. RT, 18 hr | 98 |

TABLE 10-continued

Suzuki Coupling Reaction of Electron Deficient Aryl Bromides using by Pd/Ph$_5$FcP(t-Bu)$_2$ catalyst at room temperature.

| Entry | Halide | Boronic Acid | Product | Condition[a] | Yield (%)[b] |
|---|---|---|---|---|---|
| 2 | 4-PhOC-C$_6$H$_4$-Br | C$_6$H$_5$-B(OH)$_2$ | 4-PhOC-C$_6$H$_4$-C$_6$H$_5$ | 0.0005 mol % (Pd/L) K$_3$PO$_4$/Toln. 100° C., 1 hr | 94 |
| 3 | 4-NC-C$_6$H$_4$-Cl | 4-F$_3$C-C$_6$H$_4$-B(OH)$_2$ | 4-NC-C$_6$H$_4$-C$_6$H$_4$-CF$_3$-4 | 0.5 mol % (Pd/L) KF(2)/THF. RT, 28 hr | 96 |
| 4 | 4-NC-C$_6$H$_4$-Cl | 4-MeO-C$_6$H$_4$-B(OH)$_2$ | 4-NC-C$_6$H$_4$-C$_6$H$_4$-OMe-4 | 1 mol % (Pd/L) KF(3)/THF RT | 94 |
| 5 | 4-NC-C$_6$H$_4$-Br | 4-OHC-C$_6$H$_4$-B(OH)$_2$ | 4-NC-C$_6$H$_4$-C$_6$H$_4$-CHO-4 | 0.5/1.0 mol % (Pd/L) KF(3)/THF 40° C., 12 hr | 97 |
| 6 | 4-O$_2$N-C$_6$H$_4$-Cl | 4-MeO-C$_6$H$_4$-B(OH)$_2$ | 4-O$_2$N-C$_6$H$_4$-C$_6$H$_4$-OMe-4 | 0.5 mol % (Pd/L) KF(2.2)/THF 50° C., 17 h | 98 |
| 7 | 4-O$_2$N-C$_6$H$_4$-Br | 2-CH$_3$-C$_6$H$_4$-B(OH)$_2$ | 4-O$_2$N-C$_6$H$_4$-C$_6$H$_4$-CH$_3$-2 | 0.5 mol % (Pd/L) KF(2)/THF. 50° C., 22 hr | 98 |
| 8 | 4-OHC-C$_6$H$_4$-Br | 4-Cl-C$_6$H$_4$-B(OH)$_2$ | 4-OHC-C$_6$H$_4$-C$_6$H$_4$-Cl-4 | 0.5/1.0 mol % (Pd/L) KF(3)/THF RT, 5 hr | 99 |

[a]Reaction Conditions: ArBr 0.4 or 0.5 mmol, ArB(OH)$_2$ entry 1–3; 1.1 mol equiv. To ArBr, entry 4–8, 1.3 mol equiv., solvent 2 mL.
[b]All reaction yields were isolated yields

TABLE 11

Coupling Reaction of Electron Neutral Aryl Bromides using Pd/Ph₅FcP(tBu)₂ Catalyst at Room Temperature

| Entry | Halide | Boronic Acid[a] | Product | Condition | Yield (%)[b] |
|---|---|---|---|---|---|
| 1 | PhBr | 2-MeC₆H₄B(OH)₂ | 2-methylbiphenyl | 1 mol % (Pd/L), KF(3), THF, RT, 2 days | 95 |
| 2 | PhBr | 4-MeOC₆H₄B(OH)₂ | 4-methoxybiphenyl | 1 mol % (Pd/L), KF(3), THF, RT, 16 hr | 95 |
| 3 | PhBr | 1-naphthylB(OH)₂ | 1-phenylnaphthalene | 1 mol % (Pd/L), KF(3), THF, RT, 17 hr | 99 |
| 4 | 1-bromonaphthalene | 1-naphthylB(OH)₂ | 1,1'-binaphthalene | 1 mol % (Pd/L), KF(3), THF, RT, 2 days | 97 |
| 5 | PhBr | 4-ClC₆H₄B(OH)₂ | 4-chlorobiphenyl | 0.5/1 (Pd/L), K₃PO₄, Toln. 100° C. | 78 |

[a]1.3 mol. equiv. of aryl boronic acids were used.
[b]all reaction yields were isolated yield.

TABLE 12

Suzuki Coupling Reaction of Electron rich Aryl Bromides using by Pd/Ph₅FcP(t-Bu)₂ catalyst at room temperature

| Entry | Halide | Boronic Acid[a] | Product | Condition | Yield (%) |
|---|---|---|---|---|---|
| 1 | 2-bromoanisole | 2-MeC₆H₄B(OH)₂ | 2-methoxy-2'-methylbiphenyl | 1 mol % (Pd/L), KF(2)/Toln. 100° C., 16 hr | 98 |
| 2 | 2-bromoanisole | 4-CF₃C₆H₄B(OH)₂ | 2-methoxy-4'-trifluoromethylbiphenyl | 1 mol % (Pd/L), KF(3)/Toln. RT, 3 hr | 97 |

TABLE 12-continued

Suzuki Coupling Reaction of Electron rich Aryl Bromides using by Pd/Ph$_5$FcP(t-Bu)$_2$ catalyst at room temperature

| Entry | Halide | Boronic Acid[a] | Product | Condition | Yield (%) |
|---|---|---|---|---|---|
| 3 | 2-bromoanisole | 4-chlorophenylboronic acid | 2-methoxy-4'-chlorobiphenyl | 0.5/1.0 mol % (Pd/L) KF(3)/THF RT, 5 hr | 95 |
| 4 | 3-bromoanisole | 1-naphthylboronic acid | 1-(3-methoxyphenyl)naphthalene | 0.5/1 mol % (Pd/L) KF(3)/dioxane 100° C., 18 hr | 99 |
| 5 | 5-bromo-1,3-benzodioxole | 2-methylphenylboronic acid | 5-(2-methylphenyl)-1,3-benzodioxole | 1 mol % (Pd/L) KF(2)/Toln. RT, 3 hr | 99 |
| 6 | 5-bromo-1,3-benzodioxole | 4-formylphenylboronic acid | 5-(4-formylphenyl)-1,3-benzodioxole | 1/2 mol % (Pd/L) KF(3)/dioxane 100° C., 18 hr | 85 |
| 7 | 4-bromo-t-butylbenzene | 2-methylphenylboronic acid | 4-t-butyl-2'-methylbiphenyl | 1 mol % (Pd/L) K$_3$PO$_4$(2)/Toln. 80° C., 15 hr | 97 |

[a]1.3 mol equiv. of aryl boronic acids were used

TABLE 13

Suzuki Coupling Reaction of Hindered Aryl Bromides using by Pd/Ph$_5$FcP(t-Bu)$_2$ catalyst at room temperature

| Entry | Halide | Boronic Acid[a] | Product | Condition | Yield (%)[b] |
|---|---|---|---|---|---|
| 2 | 2-bromo-1,4-dimethylbenzene | 4-chlorophenylboronic acid | 4'-chloro-2,5-dimethylbiphenyl | 1/2 mol % (Pd/L) K$_3$PO$_4$(3)/Toln. 100° C., 14 hr | 95 |

TABLE 13-continued

Suzuki Coupling Reaction of Hindered Aryl Bromides using by Pd/Ph₅FcP(t-Bu)₂ catalyst at room temperature

| Entry | Halide | Boronic Acid[a] | Product | Condition | Yield (%)[b] |
|---|---|---|---|---|---|
| 5 | 2-bromotoluene | 2-methylphenylboronic acid | 2,2'-dimethylbiphenyl | 1 mol % (Pd/L) KF(3)/THF RT, 14 hr | 98 |
| 6 | 2-bromo-1,3-dimethylbenzene | 2-methylphenylboronic acid | 2,2',6-trimethylbiphenyl | 2/4 mol % (Pd/L) K₃PO₄(3)/Toluene 100° C. | 89 |

[a] 1.1–1.5 mol equiv. of aryl boronic acids were used.
[b] all reaction yields were isolated yields and calculated based on weight of biphenyl

TABLE 14

Suzuki Coupling Reaction of Aryl Bromides

| Entry | Halide | Boronic Acid[a] | Product | Condition | Yield (%)[b] |
|---|---|---|---|---|---|
| 1 | 2-bromochlorobenzene | phenylboronic acid | 2-chlorobiphenyl | 1/2 mol % (Pd/L) KF(3)/THF RT, 14 hr | 88 |
| 2 | 2-bromophenylacetic acid | 2-methylphenylboronic acid | 2'-methyl-2-biphenylacetic acid | 1/2 mol % (Pd/L) KF(3)/THF RT | 90 |
| 3 | 2-bromo-1,3-dichlorobenzene | 2-methylphenylboronic acid | 2,6-dichloro-2'-methylbiphenyl | 1/2 mol % (Pd/L) K₃PO₄(3)/Toln. 100° C., 14 hr | 76 |

[a] 1.1–1.5 mol equiv. of aryl boronic acids were used.
[b] all reaction yields were isolated yields and calculated based on weight of biphenyl

TABLE 15

Suzuki Coupling Reaction of Electron Deficient Aryl Chlorides using by Pd/Ph$_5$FcP(t-Bu)$_2$ catalyst

| Entry | Halide | Boronic Acid[a] | Product | Condition | Yield (%)[b] |
|---|---|---|---|---|---|
| 2 | 4-Cl-C$_6$H$_4$-CN | 2-CH$_3$-C$_6$H$_4$-B(OH)$_2$ | 4-NC-C$_6$H$_4$-C$_6$H$_4$-2-CH$_3$ | 1/2 mol % (Pd/L) KF(3)/THF 45° C. | 94 |
| 3 | 4-Cl-C$_6$H$_4$-CHO | 2-CH$_3$-C$_6$H$_4$-B(OH)$_2$ | 4-OHC-C$_6$H$_4$-C$_6$H$_4$-2-CH$_3$ | 1/2 mol % (Pd/L) KF(3)/THF 45° C., 15 hr | 96 |
| 4 | 4-Cl-C$_6$H$_4$-CHO | C$_6$H$_5$-B(OH)$_2$ | 4-OHC-C$_6$H$_4$-C$_6$H$_5$ | 1/2 mol % (Pd/L) KF(3)/THF 45° C., 15 hr | 96 |
| 5 | 4-Cl-C$_6$H$_4$-CHO | 4-MeO-C$_6$H$_4$-B(OH)$_2$ | 4-OHC-C$_6$H$_4$-C$_6$H$_4$-4-OMe | 1/2 mol % (Pd/L) KF(3)/THF 50° C., 15 hr | 94 |
| 6 | 4-Cl-C$_6$H$_4$-COOMe | 4-MeO-C$_6$H$_4$-B(OH)$_2$ | 4-MeOOC-C$_6$H$_4$-C$_6$H$_4$-4-OMe | 1/2 mol % (Pd/L) KF(3)/THF 100° C. | 89 |
| 7 | 4-Cl-C$_6$H$_4$-COOMe | 2-CH$_3$-C$_6$H$_4$-B(OH)$_2$ | 4-MeOOC-C$_6$H$_4$-C$_6$H$_4$-2-CH$_3$ | 1/2 mol % (Pd/L) KF(3)/THF 100° C. | 92 |
| 8 | 4-Cl-C$_6$H$_4$-CONH$_2$ | 2-CH$_3$-C$_6$H$_4$-B(OH)$_2$ | 4-H$_2$NOC-C$_6$H$_4$-C$_6$H$_4$-2-CH$_3$ | 1/2 mol % (Pd/L) KF(3)/THF 45° C. | 91 |

[a] 1.1–1.5 mol equiv. of aryl boronic acids were used.
[b] all reaction yields were isolated yields and calculated based on weight of biphenyl

TABLE 16

Suzuki Coupling Reaction of Electron Neutral Aryl Chlorides using by Pd/Ph$_5$FcP(t-Bu)$_2$ catalyst

| Entry | Halide | Boronic Acid[a] | Product | Condition | Yield (%)[b] |
|---|---|---|---|---|---|
| 2 | Ph-Cl | Ph-B(OH)$_2$ | biphenyl | 0.5/1 mol % (Pd/L) KF(3)/THF 45° C. | 96 |

[a] 1.1–1.5 mol equiv. of aryl boronic acids were used.
[b] all reaction yields were isolated yields and calculated based on weight of biphenyl

TABLE 17

Suzuki Coupling Reaction of Electron rich Aryl Chlorides using by Pd/Ph$_5$FcP(t-Bu)$_2$ catalyst

| Entry | Halide | Boronic Acid[a] | Product | Condition | Yield (%)[b] |
|---|---|---|---|---|---|
| 2 | 4-MeO-C$_6$H$_4$-Cl | 2-CH$_3$-C$_6$H$_4$-B(OH)$_2$ | 4-MeO-2'-CH$_3$-biphenyl | 1 mol % (Pd/L) KF(3)/Toluene 80° C., 3 days | 99 |
| 3 | 3-MeO-C$_6$H$_4$-Cl | 2-CH$_3$-C$_6$H$_4$-B(OH)$_2$ | 3-MeO-2'-CH$_3$-biphenyl | 3 mol % (Pd/L) K$_3$PO$_4$(3)/Toluene 80° C., 23 hr | 87 |
| 4 | 3-MeO-C$_6$H$_4$-Cl | 4-MeO-C$_6$H$_4$-B(OH)$_2$ | 3-MeO-4'-OMe-biphenyl | 1 mol % (Pd/L) KF(3)/Toluene 80° C., 26 hr | 97 |

[a] 1.1–1.5 mol equiv. of aryl boronic acids were used.
[b] all reaction yields were isolated yields and calculated based on weight of biphenyl

TABLE 18

Suzuki Coupling Reaction of Hindered Aryl Chlorides

| Entry | Halide | Boronic Acid[a] | Product | Condition | Yield (%)[b] |
|---|---|---|---|---|---|
| 5 | 2,4-(CH$_3$)$_2$-C$_6$H$_3$-Cl (2-Cl, 1,4-diMe) | 2-CH$_3$-C$_6$H$_4$-B(OH)$_2$ | trimethyl biphenyl | 2.5/5.0 mol % (Pd/L) Cs$_2$CO$_3$(2)/dioxane 100° C., 3 days | 80% |

[a] 1.1–1.5 mol equiv. of aryl boronic acids were used.
[b] all reaction yields were isolated yields and calculated based on weight of biphenyl

TABLE 19

Suzuki Coupling Reaction with n-butylboronic acid using Pd/Ph$_5$FcP(t-Bu)$_2$ catalyst

| Entry | Aryl Halide | boronic acid | Product | Condition | Yield (%) |
|---|---|---|---|---|---|
| 1 | 4-t-Bu-C$_6$H$_4$-Br | n-Bu-B(OH)$_2$ a) | 4-t-Bu-C$_6$H$_4$-n-Bu | 1/2 mol % (Pd/L) K$_3$PO$_4$/Toln 100° C., 20 hr | 92 |
| 3 | 4-MeO-C$_6$H$_4$-Br | ↑ | 4-MeO-C$_6$H$_4$-n-Bu | 1/2 mol % (Pd/L) K$_3$PO$_4$/Toln 100° C. | 83 |
| 5 | 2-MeO-C$_6$H$_4$-Cl | ↑ | 2-MeO-C$_6$H$_4$-n-Bu | 1/2 mol % (Pd/L) K$_3$PO$_4$/Toln 100° C. | 94 |
| 6 | 4-NC-C$_6$H$_4$-Cl | ↑ | 4-NC-C$_6$H$_4$-n-Bu | 1/2 mol % (Pd/L) K$_3$PO$_4$/Toln 100° C. | 97 |
| 7 | 3-MeO-C$_6$H$_4$-Cl | ↑ | 3-MeO-C$_6$H$_4$-n-Bu | 1/2 mol % (Pd/L) K$_3$PO$_4$/Toln 100° C. | 86 |

TABLE 20

Suzuki Coupling Reaction with iso-butylboronic acid using Pd/Ph$_5$FcP(t-Bu)$_2$ catalyst

| Entry | Aryl Halide | boronic acid | Product | Condition | Yield (%) |
|---|---|---|---|---|---|
| 1 | 4-t-Bu-C$_6$H$_4$-Br | iso-Bu-B(OH)$_2$ a) | 4-t-Bu-C$_6$H$_4$-CH(CH$_3$)CH$_2$CH$_3$ | 1/2 mol % (Pd/L) K$_3$PO$_4$/Toln. 100° C., 22 hr | 55 |

TABLE 21

Kumada Coupling Reaction with Cyclohexylmagnesium Chloride using Pd/Ph$_5$FcP(tBu)$_2$ catalyst

| Entry | Aryl Halide | boronic acid | Product | Condition | Yield (%)[a] |
|---|---|---|---|---|---|
| 1 | 4-t-Bu-C$_6$H$_4$-Br | Cyclohexyl-MgCl | 4-t-Bu-C$_6$H$_4$-Cyclohexyl | 1/2 mol % (Pd/L) THF, RT to 50° C. | 45 |

Example 73

4-(2-methylphenyl)benzophenone (Table 10, Entry 1)

Prepared as described above. $^1$H-NMR (300 MHz, CDCl$_3$): δ 7.91 (m, 4H), 7.60–7.50 (m, 5H), 7.33 (m, 4H), 2.35 (s, 3H, Ar—CH$_3$). GC/MS(EI): m/z 272 (M$^+$). Anal. Calcd for C$_{20}$H$_{16}$O: C, 88.20; H, 5.92. Found: C, 88.47; H, 6.09.

Example 74

4-phenylbenzophenone (Table 10, Entry 2)

According to the general procedure described above, 4-Bromobenzophenone (131 mg, 0.50 mmol) reacted with phenylboronic acid (92 mg, 0.75 mmol) using 0.0005 mol % of Pd(dba)2, 0.002 mol % of Ph$_5$FcP(t-Bu)$_2$, and K$_3$PO$_4$ (318 mg, 1.50 mmol) in toluene solvent at 100° C. for 1 hr to title compound (121 mg, 94%) as a solid: $^1$H-NMR (400 MHz, CDCl$_3$): δ 7.92 (d, 2H, J=8.4 Hz), 7.87 (d, 2H, J=7.2 Hz), 7.73 (d, 2H, J=8.4 Hz), 7.18 (d, 2H, J=6.8 Hz), 7.63 (m, 1H), 7.51 (m, 3H), 7.43 (m, 2H). $^{13}$C{$^1$H}-NMR (100 MHz, CDCl$_3$): δ 196.30, 145.16, 139.89, 137.68, 136.15, 132.34, 130.69, 129.96, 128.92, 128.26, 128.14, 127.25, 126.91. GC/MS(EI): m/z 181 (M−77$^+$). Anal. Calcd for C$_{19}$H$_{14}$O: C, 88.34; H, 5.46. Found: C, 88.26; H, 5.62.

Example 75

4-(4-trifluoromethylphenyl)benzonitrile (Table 10, Entry 3)

4-Chlorobenzonitrile (141 mg, 1.02 mmol) reacted with p-trifluoromethylphenylboronic acid using by 1/2 mol % of Pd(OAc)$_2$/Ph$_5$FcP(t-Bu)$_2$ and KF (182 mg, 3.00 mmol) in THF solvent to give the title compound (236 mg, 96%) as a white solid after recrystallization from hexane: $^1$H-NMR (500 MHz, CDCl$_3$): δ 7.78 (d, 2H, J=8.23 Hz), 7.76 (d, 2H, J=8.48 Hz), 7.71 (app.d, 4H, J=8.18 Hz). $^{13}$C{$^1$H}-NMR (100 MHz, CDCl$_3$): δ 111.92, 118.57, 142.61, 144.09, 123.95 (q, J=270.2 Hz), 126.04 (q, J=3.6 Hz), 127.60, 127.93, 130.63 (q, J=32.5 Hz), 132.76. $^{19}$F{$^1$H}-NMR (MHz, CDCl$_3$): δ −63.0. GC/MS(EI): m/z 247 (M$^+$).

Example 76

4-(4-methoxyphenyl)benzonitrile (Table 10, Entry 4)

4-Chlorobenzonitrile (140 mg, 1.02 mmol) reacted with p-methoxyphenylboronic acid (200 mg, 1.32 mmol) using 1/2 mol % of Pd(OAc)$_2$/Ph$_5$FcP(t-Bu)$_2$ and KF (182 mg, 3.00 mmol) in THF solvent to give the title compound (197 mg, 94%) as white solid after recrystallization from hexane: $^1$H-NMR (400 MHz, CDCl$_3$): δ 7.70 (d, 2H, J=8.41 Hz), 7.65 (d, 2H, J=8.40 Hz), 7.55 (d, 2H, J=8.80 Hz), 7.02 (d, 2H, J=8.79 Hz), 3.88 (s, 3H). $^{13}$C{$^1$H}-NMR (125 MHz, CDCl$_3$): δ 160.18, 145.17, 132.52, 131.45, 128.31, 127.06, 119.04, 114.52, 110.07, 55.35. GC/MS(EI): m/z (M$^+$).

Example 77

4-(4-methoxyphenyl)nitrobenzene (Table 10, Entry 6)

4-Chloronitrobenzene (164 mg, 1.04 mmol) reacted with p-methoxyphenylboronic acid (200 mg, 1.32 mmol) using 1/2 mol % of Pd(OAc)$_2$/Ph$_5$FcP(t-Bu)$_2$ and KF (182 mg, 3.00 mmol) in THF solvent at 50° C. for 17 h to give the title compound (234 mg, 98%) as a solid: $^1$H-NMR (400 MHz, CDCl$_3$): δ 8.27 (d, 2H, J=8.76 Hz), 7.69 (d, 2H, J=8.76 Hz), 7.59 (d, 2H, J=8.70 Hz), 7.03 (d, 2H, J=8.71 Hz), 3.88 (s, 3H). $^{13}$C{$^1$H}-NMR (100 MHz, CDCl$_3$): δ 160.40, 147.15, 146.47, 130.99, 128.52, 127.01, 124.10, 114.56, 55.39. GC/MS(EI): m/z (M$^+$).

Example 78

4-(2-methylphenyl)nitrobenzene (Table 10, Entry 7)

4-Chloronitrobenzene (80 mg, 0.51 mmol) reacted with o-methylphenylboronic acid (85 mg, 0.63 mmol) using 0.5/1.0 mol % of Pd(OAc)$_2$/Ph$_5$FcP(t-Bu)$_2$ and KF (87 mg, 1.55 mmol) in THF solvent at 50° C. for 22 h to give the title compound (107 mg, 98%): $^1$H-NMR (500 MHz, CDCl$_3$): δ 8.30 (d, 2H, J=6.90 Hz, aryl coupling 1.8 Hz), 7.51 (d, 2H, J=6.92 Hz, aryl coupling 1.8 Hz), 7.35–7.23 (m, 4H), 2.29 (s, 3H, Ar—CH$_3$). $^{13}$C{$^1$H}-NMR (125 MHz, CDCl$_3$): δ 148.80, 146.86, 139.60, 135.04, 130.70, 130.09, 129.39, 128.45, 126.11, 123.40, 20.31. GC/MS(EI): m/z 213 (M$^+$), 165, 152.

Example 79

4-(4-chlorophenyl)benzaldehyde (Table 10, Entry 8)

4-Bromobenzaldehyde (95 mg, 0.51 mmol) reacted with 4-chlorophenylboronic acid (101 mg, 0.65 mmol) using 0.5/1.0 mol % of Pd(dba)$_2$/Ph$_5$FcP(t-Bu)$_2$ and KF (87 mg, 1.55 mmol) in THF solvent at room temperature to give the title compound (110 mg, 99%) as a white solid: $^1$H-NMR (400 MHz, CDCl$_3$): δ 10.07 (s, 1H, —CHO), 7.96 (d, 2H, J=7.04 Hz), 7.73 (d, 2H, J=7.04 Hz), 7.58 (d, 2H, J=7.16 Hz), 7.46 (d, 2H, J=7.27 Hz). $^{13}$C{$^1$H}-NMR (100 MHz, CDCl$_3$): δ 191.80, 145.84, 138.10, 135.35, 134.70, 130.34, 129.20, 128.58, 127.51. GC/MS(EI): m/z 216 (M$^+$), 218, 152.

Example 80

4-(4-cyanophenyl)benzaldehyde (Table 10, Entry 5)

4-Bromobenzonitrile (73 mg, 0.40 mmol) reacted with 4-formylphenylboronic acid (90 mg, 0.60 mmol) using 0.5/1.0 mol % of Pd(dba)$_2$/Ph$_5$FcP(t-Bu)$_2$ and KF (70 mg, 1.21 mmol) in THF solvent at 40° C. to give the title compound (83 mg, 97%) as a white solid: $^1$H-NMR (500 MHz, CDCl$_3$): δ 10.10 (s, 1H), 8.01 (d, 2H, J=8.25 Hz), 7.80–7.74 (m, 6H). $^{13}$C{$^1$H}-NMR (125 MHz, CDCl$_3$): δ 191.57, 144.90, 144.14, 136.14, 132.78, 130.41, 128.03, 127.91, 118.52, 112.17. GC/MS(EI): m/z 207 (M$^+$), 206.

Example 81

2-methylbiphenyl (Table 11, Entry 1)

2-Bromobenzene (80 mg, 0.51 mmol) reacted with 2-methylphenylboronic acid (90 mg, 0.66 mmol) using 1.0 mol % of Pd(dba)$_2$/Ph5FcP(t-Bu)$_2$ and KF (87 mg, 1.55 mmol) in THF solvent at room temperature to give the title compound (80 mg, 95%) as a colorless oil: $^1$H-NMR (400 MHz, CDCl$_3$): δ 7.51–7.47 (m, 2H), 7.44–7.40 (m, 3H), 7.36–7.32 (m, 4H), 2.36 (s, 3H). $^{13}$C{$^1$H}-NMR (100 MHz, CDCl$_3$): δ 141.91, 141.89, 135.30, 130.27, 129.76, 129.16, 128.03, 127.22, 126.72, 125.73, 20.46. GC/MS(EI): m/z 168 (M$^+$), 153.

Example 82

4-methoxybiphenyl (Table 11, Entry 2)

Bromobenzene (79 mg, 0.50 mmol) reacted with 4-methoxyphenylboronic acid (99 mg, 0.65 mmol) using 1 mol % of Pd(dba)$_2$/Ph$_5$FcP(t-Bu)$_2$ and KF (87 mg, 1.50 mmol) in THF solvent at room temperature to give the title compound (87 mg, 95%) as a white solid. The reaction of 4-chloroanisole (71 mg, 0.50 mmol) with phenylboronic acid (92 mg, 0.75 mmol) gave the title compound (74 mg, 80%) using 1/2 mol % of Pd(dba)$_2$/Ph$_5$FcP(t-Bu)$_2$ and KF in THF solvent at 40° C. $^1$H-NMR (400 MHz, CDCl$_3$): δ 7.61 (m, 4H), 7.48 (t, 2H, J=7.6 Hz), 7.37 (app.t, 1H, J=7.2 Hz), 7.04 (d, 2H, J=8.8 Hz), 3.90 (s, 3H). $^{13}$C{$^1$H}-NMR (100 MHz, CDCl$_3$): δ 159.09, 140.76, 133.69, 128.66, 128.08, 126.67, 126.60, 114.14, 55.26. GC/MS(EI): m/z 184 (M$^+$). Anal. Calcd for C$_{13}$H$_{12}$O: C, 84.75; H, 6.56. Found: C, 84.86; H, 6.76.

Example 83

1-phenylnaphthalene (Table 11, Entry 3)

Bromobenzene (82 mg, 0.52 mmol) reacted with 1-naphtylboronic acid (110 mg, 0.64 mmol) using 1 mol % of Pd(dba)$_2$/Ph$_5$FcP(t-Bu)$_2$ and KF (90 mg, 1.55 mmol) in THF (2 ml) at room temperature to give the title compound (106 mg, 99%) as a colorless oil: $^1$H-NMR (400 MHz, CDCl$_3$): δ 7.99–7.91 (m, 3H), 7.60–7.47 (m, 9H). $^{13}$C{$^1$H}-NMR (100 MHz, CDCl$_3$): δ 140.71, 140.21, 133.75, 131.57, 130.05, 128.23, 127.60, 127.21, 126.90, 125.99, 125.74, 125.36. GC/MS(EI): m/z 204 (M$^+$). Anal. Calcd for C$_{16}$H$_{12}$: C, 94.08; H, 5.92. Found: C, 93.96; H, 6.11.

Example 84

1,1'-bisnaphthalene (Table 11, Entry 4)

1-Bromonaphthalene (108 mg, 0.52 mmol) reacted with 1-naphtylboronic acid (112 mg, 0.65 mmol) using 1 mol % of Pd(dba)$_2$/Ph$_5$FcP(t-Bu)$_2$ and KF (87 mg, 1.50 mmol) in THF (2 ml) at room temperature to give the title compound (128 mg, 97%) as a solid: $^1$H-NMR (400 MHz, CDCl$_3$): δ 7.98 (d, 1H, J=3.45 Hz), 7.96 (d, 1H, J=3.39 Hz), 7.61 (t, 1H, J=7.30 and 7.83 Hz), 7.52–7.47 (m, 2H), 7.41 (d, 1H, J=8.36 Hz), 7.31 (t, 1H, J=7.39 and 7.62 Hz). $^{13}$C{$^1$H}-NMR (100 MHz, CDCl$_3$): δ 138.43, 133.49, 132.82, 128.12, 127.87, 127.81, 126.54, 125.95, 125.78, 125.36. GC/MS(EI): m/z (M$^+$).

Example 85

4-Chloro-1,1'-biphenyl (Table 11, Entry 5)

Bromobenzene (80 mg, 0.51 mmol) reacted with 4-chlorophenylboronic acid (103 mg, 0.66 mmol) using 0.5/1.0 mol % of Pd(dba)$_2$/Ph$_5$FcP(t-Bu)$_2$ and K$_3$PO$_4$ (318 mg, 1.50 mmol) in toluene at 100° C. to give the title compound (75 mg, 78%) as a white solid: $^1$H-NMR (400 MHz, CDCl$_3$): δ 7.41–7.62 (m, 9H). $^{13}$C{$^1$H}-NMR (100 MHz, CDCl$_3$): δ 139.95, 139.62, 133.33, 128.88, 128.86, 128.36, 127.56, 126.96. GC/MS(EI): m/z 188 (M$^+$), 152

Example 86

2-methoxy-2'-methyl-1,1'-biphenyl (Table 12, Entry 1)

2-Bromoanisole (187 mg, 1.00 mmol) reacted with 2-methylphenylboronic acid (150 mg, 1.10 mmol) using 1 mol % of Pd(dba)$_2$/Ph$_5$FcP(t-Bu)$_2$ and KF (116 mg, 2.0 mmol) in toluene at 100° C. to give the title compound (193 mg, 98%) as a colorless oil: 1H-NMR (400 MHz, CDCl$_3$): δ 7.43 (t, 1H, J=8.2 Hz, aryl coupling J=1.75 Hz), 7.36–7.24 (m 5H), 7.10 (t, 1H, J=7.4 Hz, aryl coupling 0.91 Hz), 7.05 (d, 1H, J=8.2 Hz), 3.84 (s, 3H), 2.24 (s, 3H). $^{13}$C{$^1$H}-NMR (100 MHz, CDCl$_3$): δ 156.53, 138.58, 136.77, 130.95, 130.77, 129.95, 129.52, 128.51, 127.25, 125.40, 120.38, 110.56, 55.31, 19.89. GC/MS(EI): m/z 198 (M$^+$). Anal. Calcd for C$_{14}$H$_{14}$O: C, 84.81; H, 7.12. Found: C, 84.97; H, 7.11.

Example 87

2-methoxy-4'-trifluoromethyl-1,1'-biphenyl (Table 12, Entry 2)

2-Bromoanisole (98 mg, 0.52 mmol) reacted with 4-trifluoromethylphenylboronic acid (145 mg, 0.76 mmol) using 1 mol % of Pd(dba)$_2$/Ph$_5$FcP(t-Bu)$_2$ and KF (90 mg, 1.55 mmol) in THF at room temperature for 3 h to give the title compound (128 mg, 97%). $^1$H-NMR (300 MHz, CDCl$_3$): δ $^{13}$C{$^1$H}-NMR (100 MHz, CDCl$_3$): δ. GC/MS (EI): m/z (M$^+$).

Example 88

2-methoxy-4'-chloro-1,1'-biphenyl (Table 12, Entry 3)

2-Bromoanisole (97 mg, 0.52 mmol) reacted with 4-chlorophenylboronic acid (102 mg, 0.65 mmol) using 0.5/1.0 mol % of Pd(dba)$_2$/Ph$_5$FcP(t-Bu)$_2$ and KF (8.8 mg, 1.57 mmol) in THF (2 ml) at room temperature to give the title compound (108 mg, 95%): $^1$H-NMR (400 MHz, CDCl$_3$): δ 7.51 (d, 2H, J=8.4 Hz), 7.42 (d, 2H, J=8.0 Hz), 7.46–7.32 (m, 2H), 7.08 (t, 1H, J=7.6 Hz, aryl coupling J=1.2), 7.03 (d, 1H, J=8.0 Hz), 3.85 (s, 3H). $^{13}$C{$^1$H}-NMR (100 MHz, CDCl$_3$): δ 156.27, 136.86, 132.79, 130.81, 130.60, 129.33, 128.94, 128.10, 120.85, 111.16, 55.47. GC/MS(EI): m/z 218 (M$^+$), 220 (M$^+$+2, Cl isotope peak), 168, 139. Anal. Calcd for C$_{13}$H$_{11}$ClO: C, 71.40; H, 5.07. Found: C, 71.47; H, 5.21.

Example 89

2-methyl-3',4'-methylenedioxy-1,1'-biphenyl (Table 12, Entry 5)

4-Bromo-1,2-(methylenedioxy)benzene (201 mg, 1.02 mmol) reacted with 2-methylphenylboronic acid (150 mg, 1.10 mmol) using 1 mol % of Pd(dba)$_2$/Ph$_5$FcP(t-Bu)$_2$ and KF (116 mg, 2.00 mmol) in toluene at room temperature for 3 h to give the title compound (218 mg, 99%): $^1$H-NMR (300 MHz, CDCl$_3$): δ 7.31–7.27 (m, 4H), 6.94–6.82 (m, 3H), 6.04 (s, 2H), 2.35 (s, 3H). $^{13}$C{$^1$H}-NMR (125 MHz, CDCl$_3$): δ 147.24, 146.39, 141.52, 135.84, 135.42, 130.26, 129.79, 127.10, 125.69, 122.44, 109.76, 107.98, 100.95, 20.45. GC/MS(EI): m/z 212 (M$^+$), 181, 153. Anal. Calcd for C$_{14}$H$_{12}$O$_2$: C, 79.23; H, 5.70. Found: C, 79.36; H, 5.73.

Example 90

2-methyl-4'-tert-butylbiphenyl (Table 12, Entry 7)

4-tert-butylbromobenzene (220 mg, 1.03 mmol) reacted with 2-methylphenylboronic acid (178 mg, 1.31 mmol) using 1 mol % of Pd(dba)$_2$/Ph$_5$FcP(t-Bu)$_2$ and K$_3$PO$_4$ (424 mg, mmol) in toluene at 80° C. to give the title compound (223 mg, 97%) as a colorless oil: $^1$H-NMR (300 MHz, CDCl$_3$): δ 7.49 (d, 2H, J=8.4 Hz), 7.34–7.30 (m, 6H), 2.36 (s, 3H), 1.44 (s, 9H). $^{13}$C{$^1$H}-NMR (125 MHz, CDCl$_3$): δ 149.50, 141.79, 138.88, 135.42, 130.26, 129.88, 128.81, 127.00, 125.69, 124.92, 34.51, 31.42, 20.58. GC/MS(EI): m/z (M$^+$). Anal. Calcd for C$_{17}$H$_{20}$: C, 91.01; H, 8.99. Found: C, 90.72; H, 8.88.

Example 91

4-formyl-3',4'-methylenedioxybiphenyl (Table 12, Entry 6)

4-Bromo-1,2-(methylenedioxy)benzene (80 mg, 0.40 mmol) reacted with 4-chlorophenylboronic acid (90 mg, 0.60 mmol) using 1/2 mol % of Pd(dba)$_2$/Ph$_5$FcP(t-Bu)$_2$ and KF (70 mg, 1.20 mmol) in 1,2-dioxane at 100° C. to give the title compound (77 mg, 85%) as a solid: $^1$H-NMR (400 MHz, CDCl$_3$): δ 10.05 (s, 1H), 7.93 (d, 2H, J=8.0 Hz), 7.68 (d, 2H, J=7.6 Hz), 7.14 (d, 2H), 7.13 (bs, 1H), 6.04 (s, 2H). $^{13}$C{$^1$H}-NMR (100 MHz, CDCl$_3$): δ 191.84, 148.38, 148.08, 146.81, 134.83, 133.88, 130.28, 127.26, 121.25, 108.78, 107.63, 101.41. GC/MS(EI): m/z 226 (M$^+$), 139. Anal. Calcd for C$_{14}$H$_{10}$O$_3$: C, 74.33; H, 4.46. Found: C, 74.19; H, 4.67.

Example 92

1-(3-methoxyphenyl)naphthalene (Table 12, Entry 4)

3-Bromoanisole (75 mg, 0.40 mmol) reacted with 1-naphthylboronic acid (103 mg, 0.60 mmol) using 0.5/1.0 mol % of Pd(dba)$_2$/Ph$_5$FcP(t-Bu)$_2$ and KF (70 mg, 1.20 mmol) in 1,2-dioxane at 100° C. to give the title compound (108 mg, 99%) as a colorless oil: $^1$H-NMR (500 MHz, CDCl$_3$): δ 7.96 (d, 2H, J=8.49 Hz), 7.93 (d, 2H, J=7.96 Hz), 7.89 (d, 2H, J=8.20 Hz), 7.56–7.50 (m, 2H), 7.48–7.41 (m, 3H), 7.13–7.11 (m, 1H), 7.08 (m, 1H), 7.03–7.00 (m, 1H), 3.88 (s, 3H). $^{13}$C{$^1$H}-NMR (125 MHz, CDCl$_3$): δ 159.45, 142.15, 140.09, 133.75, 131.57, 129.20, 128.22, 127.67, 126.74, 126.04, 126.01, 125.75, 125.31, 122.57, 115.61, 112.86, 55.28. GC/MS(EI): m/z 234 (M$^+$), 203, 189.

Example 93

2,5-dimethyl-2'-methylbiphenyl (Table 19, Entry 5)

2-Chloro-p-xylene (56 mg, 0.40 mmol) reacted with 2-methylphenylboronic acid (82 mg, 0.60 mmol) using 2.5/5.0 mol % of Pd(dba)$_2$/Ph$_5$FcP(t-Bu)$_2$ and Cs$_2$CO$_3$ (391 mg, 1.20 mmol) in 1,2-dioxane at 100° C. to give the title compound (63 mg, 80%): $^1$H-NMR (300 MHz, CDCl$_3$): δ 7.12–7.18 (m, 6H), 6.97 (s, 1H), 2.37 (s, 3H), 2.10 (s, 3H), 2.05 (s, 3H). $^{13}$C{$^1$H}-NMR (125 MHz, CDCl$_3$): δ 141.74, 141.45, 135.77, 134.86, 132.60, 129.94, 129.72, 129.65, 129.26, 127.81, 127.02, 125.47, 20.92, 19.81, 19.28. GC/MS(EI): m/z 196 (M$^+$).

Example 94

2-methyl-4'-methoxybiphenyl (Table 17, Entry 2)

4-Chloroanisole (74 mg, 0.52 mmol) reacted with 2-methylphenylboronic acid (102 mg, 0.75 mmol) using 1 mol % of Pd(dba)$_2$/Ph$_5$FcP(t-Bu)$_2$ and KF (87 mg, 1.50 mmol) in toluene at 80° C. to give the title compound (104 mg, 99%) as a colorless oil: $^1$H-NMR (400 MHz, CDCl$_3$): δ 7.35–7.31 (m, 6H), 7.04 (d, 2H, J=8.8 Hz), 3.92 (s, 3H), 2.37 (s, 3H). $^{13}$C{$^1$H}-NMR (125 MHz, CDCl$_3$): δ 158.43, 141.47, 135.40, 134.28, 130.25, 130.19, 129.85, 126.91, 125.71, 113.41, 55.19, 20.52. GC/MS(EI): m/z 198 (M$^+$).

Example 95

2,2'-dimethyl-1,1'-biphenyl (Table 13, Entry 5)

2-Bromotoluene (87 mg, 0.51 mmol) reacted with 2-methylphenylboronic acid (88 mg, 0.65 mmol) using 1 mol % of Pd(dba)$_2$/Ph$_5$FcP(t-Bu)$_2$ and KF (87 mg, 1.50 mmol) in THF solvent at room temperature to give the title compound (91 mg, 98%) as a colorless oil: $^1$H-NMR (300 MHz, CDCl$_3$): δ 7.29–7.35 (m, 6H), 7.20 (d, 2H, J=6.3 Hz), 2.15 (s, 6H).). $^{13}$C{$^1$H}-NMR (100 MHz, CDCl$_3$): δ 141.56, 135.76, 129.77, 129.25, 127.12, 125.51, 19.81. GC/MS(EI): m/z 182 (M$^+$).

Example 96

2,5-dimethyl-4'-chlorobiphenyl (Table 13, Entry 2)

2-Bromo-m-xylene (77 mg, 0.42 mmol) reacted with 4-chlorophenylboronic acid (94 mg, 0.60 mmol) using 1/2 mol % of Pd(dba)$_2$/Ph$_5$FcP(t-Bu)$_2$ and K$_3$PO$_4$ (254 mg, 1.20 mmol) in toluene at 100° C. to give the title compound (85 mg, 95%) as a colorless oil: $^1$H-NMR (400 MHz, CDCl$_3$): δ 7.27 (d, 2H, J=8.0 Hz), 7.14 (d, 2H, J=8.0 Hz), 7.06 (d, 1H, J=7.6 Hz), 6.98 (bs, 1H), 6.92 (s, 1H), 2.25 (s, 3H), 2.11 (s, 3H). $^{13}$C{$^1$H}-NMR (100 MHz, CDCl$_3$): δ 140.44, 135.30, 132.66, 132.04, 130.46, 130.33, 128.23, 128.18, 20.88, 19.88. GC/MS(EI): m/z 216 (M$^+$), 181, 166, 89.

Example 97

2,6dimethyl-2'-methyl-1,1'-biphenyl (Table 13, Entry 6)

2-Bromo-m-xylene (186 mg, 1.01 mmol) reacted with 2-methylphenylboronic acid (164 mg, 1.21 mmol) using 2/4 mol % of Pd(dba)$_2$/Ph$_5$FcP(t-Bu)$_2$ and K$_3$PO$_4$ (640 mg, 3.00 mmol) in toluene at 100° C. to give the title compound (170 mg, 87%) as a colorless oil: $^1$H-NMR (400 MHz, CDCl$_3$): δ 7.31–7.25 (m, 3H), 7.20–7.11 (m, 3H), 7.03 (m, 1H), 1.98 (s, 3H), 1.96 (s, 6H).

Example 98

2-chloro-1,1'-biphenyl (Table 14, Entry 1)

2-Bromochlorobenzene (96 mg, 0.50 mmol) reacted with phenylboronic acid (79 mg, 0.65 mmol) using 1/2 mol % of Pd(dba)$_2$/Ph$_5$FcP(t-Bu)$_2$ and KF (87 mg, 1.50 mmol) in THF at room temperature to give the title compound (88 mg, 93%) as a white solid: $^1$H-NMR (400 MHz, CDCl$_3$): δ 7.40–7.19 (m, 9H). $^{13}$C{$^1$H}-NMR (100 MHz, CDCl$_3$): δ 140.45, 139.33, 132.43, 131.32, 129.88, 129.39, 128.47, 127.99, 127.55, 126.77. GC/MS(EI):188 (M$^+$), 190, 152, 76.

Example 99

2-methylcarbonyloxy-2'-methyl-1,1'-biphenyl (Table 14, Entry 2)

2-Bromophenylacetic acid (86 mg, 0.40 mmol) reacted with 2-methylboronic acid (84 mg, 0.60 mmol) using 1/2 mol % of Pd(dba)$_2$/Ph$_5$FcP(t-Bu)$_2$ and KF (92 mg, 1.60 mmol) in THF solvent at room temperature to give the title compound (81 mg, 90%):

Example 100

2,6-dichloro-2'-methyl-1,1'-biphenyl (Table 14, Entry 3)

1-Bromo-2,6-dichlorobenzene (90 mg,-0.40 mmol) reacted with 2-methylphenylboronic acid (82 mg, 0.60 mmol) using 2/4 mol % of Pd(dba)$_2$/Ph$_5$FcP(t-Bu)$_2$ and K$_3$PO$_4$ (254 mg, 1.20 mmol) in toluene at 100° C. to give the title compound (88 mg, 76%): $^1$H-NMR (400 MHz, CDCl$_3$):

δ 8.07 (d, 2H, J=8.07 Hz), 7.28–7.18 (m, 3H), 7.15 (t, 1H, J=8.13 Hz), 7.00 (d, 1H, J=7.25 Hz), 1.99 (s, 3H). $^{13}C\{^1H\}$-NMR (125 MHz, CDCl$_3$): δ 139.23, 136.91, 136.16, 135.09, 129.90, 129.04, 129.01, 128.39, 127.88, 125.81, 19.30. GC/MS(EI): (M$^+$).

Example 101

4-formyl-2'-methyl-1,1'-biphenyl (Table 15, Entry 3)

4-Chlorobenzaldehyde (144 mg, 1.02 mmol) reacted with 2-methylphenylboronic acid (204 mg, 1.50 mmol) using 1/2 mol % of Pd(OAc)$_2$/Ph$_5$FcP(t-Bu)$_2$ and KF (180 mg, 3.10 mmol) in THF at 50° C. to give the title compound (189 mg, 96%) as a white solid: $^1$H-NMR (400 MHz, CDCl$_3$): δ 9.98 (s, 1H), 7.85 (d, 2H, J=8.2 Hz), 7.41 (d, 2H, J=8.1 Hz), 7.22–7.13 (m, 4H), 2.19 (s, 3H). $^{13}C\{^1H\}$-NMR (100 MHz, CDCl$_3$): δ 191.98, 148.36, 140.51, 135.06, 134.87, 130.54, 129.88, 129.55, 129.42, 128.03, 125.94, 20.34. GC/MS(EI): m/z 196 (M$^+$), 165, 167, 152. Anal. Calcd for C$_{14}$H$_{12}$O: C, 85.68; H, 6.16. Found: C, 85.64; H, 6.39.

Example 102

4-formyl-1,1'-biphenyl (Table 15, Entry 4)

4-Chlorobenzaldehyde (144 mg, 1.02 mmol) reacted with phenylboronic acid (185 mg, 1.36 mmol) using 1/2 mol % of Pd(OAc)$_2$/Ph$_5$FcP(t-Bu)$_2$ and KF (178 mg, 3.18 mmol) in THF at 50° C. to give the title compound (180 mg, 96%) as a colorless oil: $^1$H-NMR (400 MHz, CDCl$_3$): δ 8.05 (s, 1H), 7.96 (d, 2H, J=8.32 Hz), 7.76 (d, 2H, J=8.22 Hz), 7.65 (d, 2H, J=7.08 Hz), 7.52–7.14 (m, 3H). $^{13}C\{^1H\}$-NMR (100 MHz, CDCl$_3$): δ 191.88, 147.10, 139.62, 135.11, 130.21, 128.96, 128.42, 127.61, 127.30. GC/MS(EI): m/z 182 (M$^+$), 152. Anal. Calcd for C$_{13}$H$_{10}$O: C, 85.69; H. 5.53. Found: C, 85.69; H, 5.77.

Example 103

4-formyl-4'-methoxy-1,1'-biphenyl (Table 15, Entry 5)

4-Chlorobenzaldehyde (141 mg, 1.00 mmol) reacted with 4-methoxyphenylboronic acid (200 mg, 1.32 mmol) using 1/2 mol % of Pd(OAc)$_2$/Ph$_5$FcP(t-Bu)$_2$ and KF (180 mg, 3.10 mmol) in THF (2 ml) at 50° C. to give the title compound (202 mg, 94%) as a solid: $^1$H-NMR (400 MHz, CDCl$_3$): δ. $^{13}C\{^1H\}$-NMR (100 MHz, CDCl$_3$): δ 191.90, 160.78, 146.77, 134.63, 132.03, 130.31, 128.48, 127.04, 114.45, 55.38.: GC/MS (EI): m/z 212 (M$^+$).

Example 104

4-methyloxycarbonyl-4'-methoxy-1,1'-biphenyl (Table 15, Entry 6)

Methyl 4-chlorobenzoate (171 mg, 1.00 mmol) reacted with 4-methoxyphenylboronic acid (200 mg, 1.31 mmol) using 1/2 mol % of Pd(dba)$_2$/Ph$_5$FcP(t-Bu)$_2$ and KF (180 mg, 3.10 mmol) in THF at 100° C. for 4 h to give the title compound (210 mg, 89%) as a white solid: $^1$H-NMR (500 MHz, CDCl$_3$): δ 8.09 (d, 2H, J=8.35 Hz), 7.63 (d, 2H, J=8.30 Hz), 7.59 (d, 2H, J=8.71 Hz), 7.01 (d, 2H, J=8.73 Hz), 3.95 (s, 3H), 3.88 (s, 3H). $^{13}C\{^1H\}$-NMR (100 MHz, CDCl$_3$): δ 167.02, 159.77, 145.14, 132.32, 130.05, 128.31, 128.16, 126.40, 114.31, 55.32, 52.03. GC/MS (EI): m/z 242 (M$^+$), 211, 139.

Example 105

4-methyloxycarbonyl-2'-methyl-1,1'-biphenyl (Table 15, Entry 7)

Methyl 4-chlorobenzoate (172 mg, 1.01 mmol) reacted with 2-methylphenylboronic acid (210 mg, 1.54 mmol) using 1/2 mol % of Pd(dba)$_2$/Ph$_5$FcP(t-Bu)$_2$ and KF (190 mg, 3.39 mmol) in THF at 100° C. to give the title compound (209 mg, 92%) as a colorless oil: $^1$H-NMR (400 MHz, CDCl$_3$): δ 8.13 (d, 2H, J=8.24 Hz), 7.44 (d, 2H, J=8.20 Hz), 7.33–7.25 (m, 4H), 3.98 (s, 3H), 2.30 (s, 3H). $^{13}C\{^1H\}$-NMR (100 MHz, CDCl$_3$): δ 166.98, 146.69, 140.79, 135.10, 130.44, 129.47, 129.36, 129.21, 128.53, 127.78, 125.85, 52.06, 20.33. GC/MS(EI): m/z 226 (M$^+$), 195, 165, 152. Anal. Calcd for C$_{15}$H$_{14}$O$_2$: C, 79.62; H, 6.24. Found C, 79.33; H, 6.26.

Example 106

4-carbamide-2'-methyl-1,1'-biphenyl (Table 15, Entry 8)

4-Chlorobenzamide (62 mg, 0.40 mmol) reacted with 2-methylphenylboronic acid (82 mg, 0.60 mmol) using 1/2 mol % of Pd(dba)$_2$/Ph$_5$FcP(t-Bu)$_2$ and KF (70 mg, 1.20 mmol) in THF at 45° C. to give the title compound (77 mg, 91%) as a white solid: $^1$H-NMR (400 MHz, DMSO-d$_6$): δ 8.05 (bs, 1H), 7.95 (d, 2H, J=8.1 Hz), 7.42 (d, 2H, J=7.93 Hz), 7.31–7.22 (m, 4H), 2.23 (s, 3H). $^{13}C\{^1H\}$-NMR (100 MHz, DMSO-d$_6$): δ 167.67, 144.12, 140.52, 134.69, 132.78, 130.44, 129.42, 128.84, 127.68, 127.45, 126.03, 20.14.

Example 107

1,1'-biphenyl (Table 16, Entry 2)

Chlorobenzene (56 mg, 0.50 mmol) reacted with phenylboronic acid (92 mg, 0.75 mmol) using 0.5/1.0 mol % of Pd(dba)$_2$/Ph$_5$FcP(t-Bu)$_2$ and KF (87 mg, 1.50 mmol) in THF solvent at 45° C. to give the title compound (74 mg, 96%) as a white solid.

Example 108

3-methoxy-2'-methyl-1,1'-biphenyl (Table 17, Entry 3)

3-3-Chloroanisole (71 mg, 0.50 mmol) reacted with 2-methylphenylboronic acid (82 mg, 0.60 mmol) using 3 mol % of Pd(dba)$_2$/Ph$_5$FcP(t-Bu)$_2$ and K$_3$PO$_4$ (318 mg, 1.50 mmol) in toluene at 80° C. to give the title compound (86 mg, 87%) as a colorless oil: $^1$H-NMR (400 MHz, CDCl$_3$): δ 7.39 (t, 1H, J=7.6 and 8.0 Hz), 7.33–7.30 (m, 4H), 6.99–6.94 (m, 3H), 3.89 (s, 3H), 2.35 (s, 3H). $^{13}C\{^1H\}$-NMR (100 MHz, CDCl$_3$): δ 159.23, 143.32, 141.75, 135.27, 130.25, 129.60, 129.00, 127.26, 125.67, 121.63, 114.78, 112.23, 55.16, 20.42. GC/MS (EI): m/z 198 (M$^+$), 167 (M$^+$-OMe). Anal. Calcd for C$_{14}$H$_{14}$O: C, 84.81; H, 7.12. Found C, 84.72; H, 7.09.

Example 109

3-methoxy-4'-methoxy-1,1'-biphenyl (Table 17, Entry 4)

3-Chloroanisole (76 mg, 0.54 mmol) reacted with 4-methoxyphenylboronic acid (117 mg, 0.77 mmol) using 1 mol % of Pd(dba)$_2$/Ph$_5$FcP(t-Bu)$_2$ and KF (87 mg, 1.50 mmol) in toluene at 80° C. to give the title compound (112 mg, 97%) as a colorless oil: $^1$H-NMR (300 MHz CDCl$_3$): δ 7.57 (d, 2H, J=8.7 Hz), 7.37 (t, 1H, J=7.8 and 8.1 Hz), 7.17 (m, 2H), 7.01 (d, 2H, J=8.7 Hz), 6.88–6.97 (m, 1H), 3.89 (s, 3H), 3.88 (s, 3H). $^{13}C\{^1H\}$-NMR (100 MHz, CDCl$_3$): δ 159.86, 159.17, 142.28, 135.51, 129.66, 128.13, 119.21, 114.09, 112.44, 111.93. GC/MS (EI): m/z 214 (M+), 199, 171, 128. Anal. Calcd for C$_{14}$H$_4$O$_2$: C, 78.48; H, 6.59. Found C, 78.46: H, 6.62.

Example 110

4-cyano-2'-methyl-1,1'-biphenyl (Table 15, Entry 2)

4-Chlorobenzonitrile (55 mg, 0.40 mmol) reacted with 2-methylphenylboronic acid (82 mg, 0.60 mmol) using 1 mol % of Pd(dba)$_2$/Ph$_5$FcP(t-Bu)$_2$ and KF (70 mg, 1.21 mmol) in THF at 45° C. to give the title compound (72 mg, 94%) as a white solid: $^1$H-NMR (300 MHz, CDCl$_3$): δ 7.73 (d, 2H, J=8.1 Hz), 7.46 (d, 2H, J=8.4 Hz), 7.27–7.34 (m, 3H), 7.21, (d, 1H, J=6.9 Hz), 2.80 (s, 3H). $^{13}$C{$^1$H}-NMR (100 MHz, CDCl$_3$): δ 146.76, 139.97, 135.00, 131.94, 130.64, 129.97, 129.39, 128.26, 126.07, 118.93, 110.70, 20.28. GC/MS (EI): m/z 193 (M+), 165.

Example 111

4-carbonyloxymethyl-1,1'-biphenyl (not show in Table form)

Methyl 4-chlorobenzoate (85 mg, 0.50 mmol) reacted with phenylboronic acid (92 mg, 0.75 mmol) using 0.001/0.004 mol % of Pd(dba)$_2$/Ph$_5$FcP(t-Bu)$_2$ and K$_3$PO$_4$ (320 mg, 1.51 mmol) in toluene at 100° C. to give the title compound (85 mg, 80%) as a white solid: $^1$H-NMR (400 MHz, CDCl$_3$): δ 8.13 (d, 2H, J=8.45 Hz), 7.68 (d, 2H, J=8.46 Hz), 7.65 (m, 2H), 7.48 (app.t, 2H, J=7.68 Hz), 7.41 (app.t, 1H, J=7.3 Hz), 3.96 (s, 3H).). $^{13}$C{$^1$H}-NMR (100 MHz, CDCl$_3$): δ 166.97, 145.58, 139.94, 130.06, 128.89, 128.82, 128.10, 127.24, 127.01, 52.11. GC/MS (EI): m/z 212 (M+), 181, 152.

Example 112

4-tert-butyl-1-n-butylbenzene (Table 19, Entry 1)

Synthesis of this compound followed procedure A above. $^1$H-NMR(400 MHz, CDCl$_3$): δ 7.39 (d, 2H, J=8.2 Hz), 7.21 (d, 2H, J=8.2 Hz), 2.67 (t, 2H, J=7.6 and 8.0 Hz), 1.69 (m, 2H), 1.45 (m, 2H), 1.40 (s, 9H), 1.02 (t, 3H, J=7.6 Hz). $^{13}$C{$^1$H}-NMR (100 MHz, CDCl$_3$): δ 148.23, 139.80, 128.01, 125.07, 35.12, 34.29, 33.67, 31.42, 22.48, 14.00. GC/MS (ED: m/z 190 (M+), 175 (M+–CH$_3$). Anal. Calcd. for C$_{14}$H$_{22}$: C, 88.35; H, 11.65. Found: C, 88.05; H, 11.56.

Example 113

4-tert-butyl-1-iso-butylbenzene (Table 20, Entry 1)

According to the procedure A, 4-tert-butylbromobenzne was converted to the title compound as a colorless oil (105 mg, 55%): $^1$H-NMR(400 MHz, CDCl$_3$): δ 7.35 (d, 2H, J=7.24 Hz), 7.16 (d, 2H, J=7.61 Hz), 2.62 (m, 1H), 1.62 (m, 2H), 1.36(s, 9H), 1.27 (d, 3H, J=6.28 Hz), 0.88 (t, 3H, J=6.90 and 7.08 Hz). $^{13}$C{$^1$H}-NMR (100 MHz, CDCl$_3$): δ 148.35, 144.56,126.59, 125.02, 41.03, 34.29, 31.42, 31.21, 21.66, 12.31. GC/MS (EI): m/z 190 (M+), 175 (M+–CH$_3$), 161. Anal. Calcd. for C$_{14}$H$_{22}$: C, 88.35; H, 11.65. Found: C, 88.09; H, 11.68.

Example 114

4-n-butylanisole (Table 19, Entry 3)

According to the procedure A, 4-bromoanisole was converted to the title compound as a colorless oil (132 mg, 83%): $^1$H-NMR (500 MHz, CDCl$_3$): δ 7.13 (d, 2H, J=8.48 Hz), 6.86 (d, 2H, J=8.55 Hz), 3.82 (s, 3H), 2.59 (t, 2H, J=7.65 and 7.79 Hz), 1.60 (m, 2H), 1.40 (m, 2H), 0.96 (t, 3H, J=7.34 Hz). $^{13}$C{$^1$H}-NMR (125 MHz, CDCl$_3$): δ 157.59, 134.99, 129.22, 113.62, 55.20, 34.70, 33.89, 22.29, 13.63. GC/MS (EI): m/z 164 (M+), 121 (M+-propyl), 91. Anal. Calcd. for C$_{11}$H$_{16}$O: C, 80.44; H, 9.82., Found: C, 80.18; H, 9.87.

Example 115

2-n-butylanisole (Table 19, Entry 5)

According to the procedure A, 2-chloroanisole was converted to the title compound as a colorless oil (80 mg, 94%): $^1$H-NMR (400 MHz, CDCl$_3$): δ 7.22–7.15 (m, 2H), 6.91 (t, 1H, J=7.2 Hz, aryl coupling 0.8 Hz), 6.87 (d, 2H, J=8.0 Hz), 3.85 (s, 3H), 2.64 (t, 2H, J=7.2and 8.0 Hz), 1.58 (m, 2H), 1.40 (m, 2H), 0.96 (t, 3H, J=7.2 and 7.6Hz). $^{13}$C{$^1$H}-NMR (100 MHz, CDCl$_3$): δ 157.39, 131.27, 129.70, 126.71, 120.24, 110.14, 55.22, 32.05, 29.84, 22.66, 14.03. GC/MS (EI): m/z 164 (M+), 121 (M+-propyl). Anal. Calcd. for C$_{11}$H$_{16}$O: C, 80.44; H, 9.82. Found: C, 80.64; H, 9.96.

Example 116

2-n-butyltoluene

According to the procedure A, 2-chlorotoluene was converted to the title compound as a colorless oil (65 mg, 88%): $^1$H-NMR (400 MHz, CDCl$_3$): δ 7.14 (m, 4H), 2.63 (t, 2H, J=7.6 and 8.0 Hz), 2.34 (s, 3H), 1.61 (m, 2H), 1.45 (m, 2H), 0.99 (t, 3H, J=6.8 and 7.2Hz). $^{13}$C{$^1$H}-NMR (100 MHz, CDCl$_3$): δ 141.06, 135.80, 130.04, 128.77, 125.79, 125.67, 33.02, 32.46, 22.75, 19.26, 14.02. GC/MS (EI): m/z 148 (M+), 105 (M+-propyl).

Example 117

4-n-butylcyanobenzene (Table 19, Entry 6)

According to the procedure A, 4-chlorobenzonitrile was converted to the title compound as a colorless oil (80 mg, 97%): $^1$H-NMR (400 MHz, CDCl$_3$): δ 7.55 (d, 2H, J=7.6 Hz), 7.27 (d, 2H, J=7.6 Hz), 2.66 (t, 2H, J=7.6 Hz), 1.60(m, 2H), 1.35 (m, 2H), 0.93 (t, 3H, J=7.2 and 7.6 Hz). $^{13}$C{$^1$H}-NMR (100 MHz, CDCl$_3$): δ 148.48, 131.96, 129.10, 119.10, 109.31, 35.70, 32.99, 22.15, 13.77. GC/MS (EI): m/z 159 (M+), 117. Anal. Calcd. for C$_{11}$H$_{13}$N: C,82.97; H, 8.23; N, 8.80. Found: C, 83.19; H, 8.25; N, 8.83.

Example 118

3-n-butylanisole (Table 19, Entry 7)

According to the procedure A, 3-chloroanisole was converted to the title compound as a colorless oil (161 mg, 94%): $^1$H-NMR (400 MHz, CDCl$_3$): δ $^{13}$C{$^1$H}-NMR (100 MHz, CDCl$_3$): δ 159.52, 144.56, 129.12, 120.84, 114.16, 110.75, 55.07, 35.70, 33.53, 22.36, 13.94. GC/MS (EI): m/z 164 (M+), 122.

D. Reactions of Aryl Halides and Malonates or Cyanoacetates

The method of the invention may be used to produce arylated cyanoacetates and arylated malonates as shown in Tables 22 and 23 respectively.

TABLE 22

Arylation of Ethyl Cyanoacetate.[a]

[Scheme: Ethyl cyanoacetate + ArX → 2-aryl ethyl cyanoacetate; 2% Pd(dba)₂/4% Ligand, Na₃PO₄, Toluene, 6 h, 70° C.]

| Entry | Aryl halide | Yield (%) |
|---|---|---|
| 1 | 4-CF₃-C₆H₄-Br | 87[b] |
| 2 | 4-Ph-C₆H₄-Br (biphenyl bromide) | 91[b] |
| 3 | 2-naphthyl-Br | 91[b] |
| 4 | 6-chloro-1,3-benzodioxole | 86[c] |
| 5 | 2-methoxychlorobenzene | 81[c] |

[a]Reactions conducted in duplicate on a 1.0 mmol scale in toluene using 1.1 equiv. of ethyl cyanoacetate, 1.0 equiv. of aryl halide, and 3.0 equiv. of Na₃PO₄;
[b]1.0 mol % Pd(dba)₂ used;
[c]1.0 mol % (Pd(allyl)Cl)₂ used at 100° C. for 12 h. Yields are an average of two runs.

TABLE 23

Reaction of Diethyl Malonate with Aryl Chlorides[a]

[Scheme: Diethyl malonate + ArCl → 2-aryl diethyl malonate; 2% Pd(dba)₂, 4% ligand, K₃PO₄, Toluene, 100° C., 16–21 h]

| Entry | Aryl Chloride | Yield (%) |
|---|---|---|
| 1 | C₆H₅-Cl | 81 |
| 2 | 4-MeO-C₆H₄-Cl | 86 |
| 3 | 6-chloro-1,3-benzodioxole | 85 |
| 4 | 4-CF₃-C₆H₄-Cl | 89 |
| 5 | 2-methoxychlorobenzene | 87 |

[a]Reactions conducted in duplicate on a 1 mmol scale in toluene using 1.1 equiv. of ethyl malonate, 1.0 equiv. of aryl chloride, and 3.0 equiv of K₃PO₄. Yields are an average of two runs.

General Procedure for the Arylation of Ethyl Cyanoacetate (Table 22)

Method A

Into a screw-capped vial containing ethyl cyanoacetate (1.1 mmol) and aryl bromide (1.0 mmol) was added phosphine (0.040 mmol), Pd(dba)₂ (0.020 mmol) or [Pd(allyl)Cl]₂ (0.010 mmol), and Na₃PO₄ (followed by toluene (3.0 mL). The vial was sealed with a cap containing a PTFE septum and removed from the dry box. The heterogeneous reaction mixture was stirred at 70° C. and monitored by GC. After complete conversion of the aryl bromide, the crude reaction was filtered through a plug of Celite and concentrated in vacuo. The residue was purified by chromatography on silica gel (1:3 dichloromethane/hexanes).

Method B

Into a screw-capped vial containing ethyl cyanoacetate (1.1 mmol) and aryl chloride (1.0 mmol), was added P(t-Bu)₃ (0.040 mmol), [Pd(allyl)Cl]₂ (0.010 mmol), and Na₃PO₄ (3.0 mmol), followed by toluene (3.0 mL). The vial was sealed with a cap containing a PTFE septum and removed from the dry box. The heterogeneous reaction mixture was stirred at 100° C. and monitored by GC. After complete conversion of the aryl chloride, the crude reaction was filtered through a plug of Celite and concentrated in vacuo. The residue was purified by chromatography on silica gel (1:3 dichloromethane/hexanes).

Example 119

Ethyl 2-(4-Trifluoromethylphenyl)cyanoacetate (Table 22, Entry 1)

Method A of the above general procedure was followed using 4-bromobenzotrifluoride (226 mg, 1.01 mmol), ethyl cyanoacetate (123 mg, 1.09 mmol), pentaphenylferrocenyl ligand (14 mg, 0.020 mmol) and Pd(dba)$_2$ (6.0 mg, 0.010 mmol). The reaction mixture was purified by column chromatography on silica gel (1:3 dichloromethane/hexanes) to give the desired product (213 mg, 82%) as a colorless oil: $^1$H NMR (CDCl$_3$) δ 7.71–7.69 (m, 2H), 7.63–7.60 (m, 2H), 4.80 (s, 1H), 4.27 (dq, 7.2, 1.2 Hz, 2H), 1.30 (t, 7.2 Hz, 3H). $^{13}$C{$^1$H} NMR (CDCl$_3$) δ 164.28, 133.81, 131.66 (q, 33.0 Hz), 128.55, 126.38 (q, 3.7 Hz), 123.68 (q, 272.3 Hz), 115.00, 63.78, 43.52, 13.89.

Example 120

Ethyl 2-(4-Biphenyl)cyanoacetate (Table 22, Entry 2)

Method A of the above general procedure was followed using 4-bromobiphenyl (233 mg, 1.00 mmol), ethyl cyanoacetate (124 mg, 1.10 mmol), pentaphenylferrocenyl ligand (28 mg, 0.040 mmol) and Pd(dba)$_2$ (11.6 mg, 0.0200 mmol). The reaction mixture was purified by column chromatography on silica gel (1:3 dichloromethane/hexanes) to give the desired product (234 mg, 88%) as a colorless oil: $^1$H NMR (CDCl$_3$) δ 7.64–7.62 (m, 2H), 7.58–7.56 (m, 2H), 7.54–7.52 (m, 2H), 7.46–7.43 (m, 2H), 7.39–7.35 (m, 1H), 4.76 (s, 1H), 4.31–4.20 (m, 2H), 1.29 (t, 7.2 Hz, 3H). $^{13}$C{$^1$H} NMR (CDCl$_3$) δ 164.98, 142.19, 139.91, 128.91, 128.83, 128.33, 127.99, 127.84, 127.12, 115.68, 63.40, 43.40, 13.91.

Example 121

Ethyl 2-(2-Naphthyl)cyanoacetate (Table 22, Entry 3)

Method A of the above general procedure was followed using 2-bromonaphthalene (208 mg, 1.00 mmol), ethyl cyanoacetate (123 mg, 1.09 mmol), pentaphenylferrocenyl ligand (14.0 mg, 0.020 mmol) and Pd(dba)$_2$ (6.0 mg, 0.010 mmol). The reaction mixture was purified by column chromatography on silica gel (1:3 dichloromethane/hexanes) to give the desired product (2194 mg, 91%) as a colorless oil: $^1$H NMR (CDCl$_3$) δ 7.94 (s, 1H), 7.89–7.82 (m, 3H), 7.55–7.50 (m, 3H), 4.88 (s, 1H), 4.29–4.20 (m, 2H), 1.26 (t, 7.2 Hz, 3H). $^{13}$C{$^1$H} NMR (CDCl$_3$) δ 165.00, 133.21, 133.16, 129.35, 128.07, 127.76, 127.51, 127.21, 127.08, 126.96, 124.81, 115.75, 63.38, 43.90, 13.89.

Example 122

Ethyl 2-(3,4-Methylenedioxyphenyl)cyanoacetate (Table 22, Entry 4)

Method B of the above general procedure was followed using 4-chloro-1,2-(methylenedioxy)benzene (157 mg, 1.00 mmol) and ethyl cyanoacetate (124 mg, 1.10 mmol). The reaction mixture was purified by column chromatography on silica gel (1:3 dichloromethane/hexanes) to give the desired product (191 mg, 82%) as a colorless oil: $^1$H NMR (CDCl$_3$) δ 6.93–6.90 (m, 2H), 6.83–6.80 (m, 1H), 6.00 (s, 2H), 4.62 (s, 1H), 4.30–4.19 (m, 2H), 1.29 (t, 7.2 Hz, 3H). $^{13}$C{$^1$H} NMR (CDCl$_3$) δ 165.07, 148.46, 148.44, 123.33, 121.76, 115.75, 108.79, 108.25, 101.68, 63.34, 43.31, 13.92. Anal. Calcd. for C$_{12}$H$_{11}$NO$_4$: C, 61.80; H, 4.75; N, 6.01. Found: C, 62.08: H, 4.62: N, 6.13.

Example 123

Ethyl 2-(2-Methoxyphenyl)cyanoacetate (Table 22, Entry 5)

Method B of the above general procedure was followed using 2-chloroanisole (143 mg, 1.01 mmol) and ethyl cyanoacetate (125 mg, 1.11 mmol). The reaction mixture was purified by column chromatography on silica gel (1:3 dichloromethane/hexanes) to give the desired product (191.4 mg, 87%) as a colorless oil: $^1$H NMR (CDCl$_3$) δ 7.40–7.35 (m, 2H), 7.03–6.99 (m, 1H), 6.93 (d, 8.0 Hz, 1H), 5.03 (s, 1H), 4.30–4.22 (m, 2H), 3.86 (s, 3H), 1.29 (t, 7.2 Hz, 3H). $^{13}$C{$^1$H} NMR (CDCl$_3$) δ 165.19, 156.48, 130.73, 129.44, 121.11, 119.11, 115.92, 111.12, 62.97, 55.72, 38.18, 13.97.

General Procedure for the Arylation of Diethyl Malonate with Aryl Chlorides (Table 23)

To a screw-capped vial containing diethyl malonate (1.1 mmol) and aryl chloride (1.0 mmol) was added phosphine (0.040 mmol), Pd(dba)$_2$ (0.020 mmol), and K$_3$PO$_4$ (3.0 mmol) followed by toluene (3.0 mL). The vial was sealed with a cap containing a PTFE septum and removed from the dry box. The heterogeneous reaction mixture was stirred at 100° C. and monitored by GC. After complete conversion of the aryl halide, the crude reaction was filtered through a plug of Celite and concentrated in vacuo. The residue was purified by chromatography on silica gel (1:2 dichloromethane/hexanes).

Example 124

Diethyl 2-Phenylmalonate (Table 23, Entry 1)

$^1$H NMR (CDCl$_3$) δ 7.43–7.34 (m, 5H), 4.62 (s, 1H), 4.27–4.18 (m, 4H), 1.27 (t, 7.2 Hz, 6H). $^{13}$C{$^1$H} NMR (CDCl$_3$) δ 168.17, 132.81, 129.27, 128.59, 128.20, 61.80, 57.96, 14.01.

Example 125

Diethyl 2-(4-Methoxyphenyl)malonate (Table 23, Entry 2)

$^1$H NMR (CDCl$_3$) δ 7.34–7.28 (m, 2H), 6.99–6.95 (m, 1H), 6.90–6.88 (m, 1H), 5.11 (s, 1H), 4.28–4.17 (m, 4H), 3.82 (s, 3H), 1.26 (t, 7.2 Hz, 6H). $^{13}$C{$^1$H} NMR (CDCl$_3$) δ 168.63, 156.89, 129.43, 129.33, 121.87, 120.67, 110.66, 61.60, 55.61, 51.28, 14.06.

Example 126

Diethyl 2-(3,4-Methylenedioxyphenyl)malonate (Table 23, Entry 3)

$^1$H NMR (CDCl$_3$) δ 6.96 (d, 1.6 Hz, 1H), 6.81 (dd, 8.0, 1.6 Hz, 1H), 6.77 (d, 8.0 Hz, 1H), 5.96 (s, 2H), 4.52 (s, 1H), 4.27–4.15 (m, 4H), 1.27 (t, 7.2 Hz, 6H). $^{13}$C{$^1$H} NMR (CDCl$_3$) δ 168.25, 147.82, 147.62, 126.31, 122.96, 109.58, 108.21, 101.23, 61.84, 57.45, 14.03. Anal. Calcd. for C$_{14}$H$_{16}$O$_6$: C, 59.99; H, 5.75. Found: C, 60.01: H, 5.80.

Example 127

Diethyl 2-(4-Trifluoromethylphenyl)malonate (Table 23, Entry 4)

$^1$H NMR (CDCl$_3$) δ 7.63 (d, 8.4 Hz, 2H), 7.55 (d, 8.4 Hz, 2H), 4.68 (s, 1H), 4.29–4.17 (m, 4H), 1.27 (t, 7.2 Hz, 6H). $^{13}$C{$^1$H} NMR (CDCl$_3$) δ 167.54, 136.64, 130.49 (q, 32.5 Hz), 129.83, 125.55 (q, 3.7 Hz), 124.02 (q, 272.2 Hz), 62.18, 57.71, 14.00.

Example 128

Diethyl 2-(2-Methoxyphenyl)malonate (Table 23, Entry 5)

$^1$H NMR (CDCl$_3$) δ 7.34–7.28 (m, 2H), 6.99–6.95 (m, 1H), 6.90–6.88 (m, 1H), 5.11 (s, 1H), 4.28–4.17 (m, 4H), 3.82 (s, 3H), 1.26 (t, 7.2 Hz, 6H). $^{13}$C{$^1$H} NMR (CDCl$_3$) δ 168.63, 156.89, 129.43, 129.33, 121.87, 120.67, 110.66, 61.60, 55.61, 51.28, 14.06.

E. Reactions of Aryl Halides with Carbamates, Indoles, Organomagnesium and Organozinc Compounds The method of the present invention may also be used to react aryl halides with carbamates, indoles, organomagnesium and organozinc compounds as shown in Tables 24 and 25.

TABLE 24

Amination Reaction of Aryl Halides with Carbamates and Indole using Pd/Ph₅FcP(tBu)₂ Catalyst

| Entry | Halide | amine | Product | Condition | Yield (%) |
|---|---|---|---|---|---|
| 1 | 4-MeO-C₆H₄-Br | indole | 1-(4-methoxyphenyl)indole | 2/4 mol % (Pd/L) Cs₂CO₃/Toluene 100° C., 15 h | 84 |
| 2 | 2-Br-C₆H₄-CH₃ | H₂N-C(O)-OtBu | 2-CH₃-C₆H₄-NH-C(O)-Ot-Bu | 1/2 mol % (Pd/L) PhONa/Toluene 100° C. | 89 |
| 3 | C₆H₅-Br | H₂N-C(O)-OtBu | C₆H₅-NH-C(O)-Ot-Bu | 0.5/1 mol % (Pd/L) K₃PO₄/Toluene 80° C. | 99 |
| 4 | C₆H₅-Cl | H₂N-C(O)-OtBu | C₆H₅-NH-C(O)-Ot-Bu | 1/2 mol % (Pd/L) PhONa/Toluene 100° C. | 86 |

TABLE 25

Cross-Coupling Reaction of Aryl Halides with Grignard Reagent using Pd/Ph₅FcP(tBu)₂ Catalyst

| Entry | Halide | Grignard | Product | Condition | Yield (%) |
|---|---|---|---|---|---|
| 1 | 4-t-Bu-C₆H₄-Br | PhCH₂MgCl | 4-t-Bu-C₆H₄-CH₂-Ph | 1/2 mol % (Pd/L) Et₂O, r.t. | 97 |
| 2 | 4-MeO-C₆H₄-Cl | " | 4-MeO-C₆H₄-CH₂-Ph | 1/2 mol % (Pd/L) Et₂O—THF, r.t. to 45° C. | 75 |
| 3 | 2-Me-C₆H₄-Cl | " | 2-Me-C₆H₄-CH₂-Ph | 1/2 mol % (Pd/L) Et₂O—THF, r.t. to 100° C. | 88 |
| 4 | 4-t-Bu-C₆H₄-Br | sec-BuZnCl | 4-t-Bu-C₆H₄-sec-Bu | 1/2 mol % (Pd/L) Et₂O, r.t. | 76 |

Pd/L = Pd(dba)₂/Ph₅FcP(t-Bu)₂

F. Reactions of Aryl Halide with Olefins

The method of the present invention may also be used to react aryl halides with olefins using Heck chemistry as shown in Tables 24 and 25.

General Methods $^1$H and $^{13}$C NMR spectra were recorded on a Bruker DPX 400 MHz Spectrometer, General Electric QE 300 MHz spectrometer, or a General Electric Omega 500 spectrometer with tetramethylsilane or residual protiated solvent used as a reference. Elemental analyses were performed by Robertson Microlabs, Inc., Madison, N.J. Yields for final product in Table 26 refer to isolated yields of compounds of greater than 95% purity, as determined by $^1$H-NMR and capillary gas chromatography (GC). All $^{31}$P and $^{13}$C NMR spectra were proton decoupled. GC analyses were performed on a HP-5890 series II instrument equipped with an HP3395 intelligent recorder. GC/MS spectra were recorded on a HP5890 instrument equipped with a HP5971A Mass Spectral Analyzer. Both GC and GC/MS were performed using a HP-1 methyl silicone column. Yields reported in Table 26 are an average of two runs. Methyl acrylate, 2-bromoanisole, 4-bromoanisole, 4-bromotoluene, 1-bromonapthalene, 4-bromobenzotrifluoride, bromobenzene, and 2-(3-bromophenyl)-1,3-dioxolane were purchased from Aldrich and used without further purification. Dioxane and dimethylformamide were purchased as anhydrous grade and stored in a drybox. Propyl methyl ketone and butyronitrile were purchased from Aldrich and degassed before use. Triethylamine was purchased from Aldrich and dried over molecular sieves before use. Ether, toluene, tetrahydrofuran, benzene, and pentane were distilled from sodium/benzophenone.

General Procedure for Room Temperature Palladium Catalyzed Heck Reactions

The reaction conditions and results are shown in Table 26. A typical procedure is given for the reaction of Entry 1 in Table 26.

A 4 mL vial was charged with 4-bromoanisole (187 mg, 1.00 mmol), Pd(dba)$_2$ (14.4 mg, 0.0250 mmol), Ph$_5$FcP(t-Bu)$_2$ (35.5 mg, 0.0500 mmol), and 1 mL of anhydrous DMF. The vial was sealed with a cap containing a PTFE septum and removed from the drybox. NEt$_3$ (167 μL, 1.20 mmol) was added by syringe. The reaction was stirred at room temperature for 20 h. The reaction mixture was then poured into a saturated lithium chloride solution and extracted (3×10 mL) with ether. The ether was evaporated under vacuum, and the product was isolated by flash chromatography, eluting with 15% ethyl acetate/hexanes, to give 176 mg (92%) of 3-(4-methoxy-phenyl)acrylic acid methyl ester.

TABLE 26

Room Temperature Heck Reactions of Aryl Bromides[a]

| Entry | Ar | Yield (%) |
|---|---|---|
| 1 | 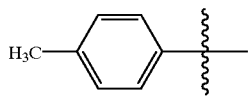 | 91 |
| 2 | 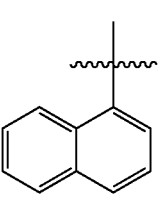 | 91 |
| 3 | 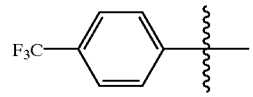 | 95 |

TABLE 26-continued

Room Temperature Heck Reactions of Aryl Bromides[a]

| Entry | Ar | Yield (%) |
|---|---|---|
| 4 | 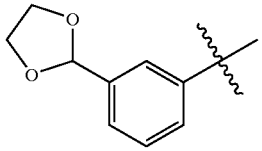 | 88 |
| 5 | 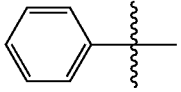 | 89 |
| 6 | 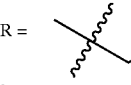 | 94 |

R = $\text{—CH=CH—C(O)OMe}$  L = Ph$_5$FcP(t-Bu)$_2$

[a]Reactions conducted on a 1 mM scale in DMF for 20 H using 1.0 equiv. of aryl halide, 1.1 equiv. of vinyl substrate, 2.5 mol % Pd(dba)$_2$, 5.0 mol % L, and 1.1 equiv. Net$_3$. Isolated yields are an average of two runs.

Spectroscopic Data of Products in Table 26
  Table 26, Entry 1
  The $^1$H NMR spectroscopic data of 3-(4-methoxy-phenyl) acrylic acid methyl ester were identical to that published previously (Littke, A. F.; Fu, G. C. J. Org. Chem. 1999, 64, 10–11).
  Table 26, Entry 2
  The $^1$H NMR spectroscopic data of 3-p-tolyl-acrylic acid methyl ester was identical to that published previously (Lewis, F. D.; Oxman, J. D.; Gibson, L. L.; Hampsch, H. L.; Quinllen, S. L. J. Am. Chem. Soc. 1986, 108, 3005–3015).
  Table 26, Entry 3
  The $^1$H NMR spectroscopic data of 3-napthalen-1-yl-acrylic acid methyl ester was identical to that published previously (Lee, T.; Jones, J. B. J. Am. Chem. Soc. 1997, 119, 10260–10268)
  Table 26, Entry 4
  The $^1$H NMR spectroscopic data of 3-(4-trifluoromethyl-phenyl)-acrylic acid methyl ester was identical to that published previously (Lewis, F. D.; Oxman, J. D.; Gibson, L. L.; Hampsch, H. L.; Quillen, S. L. J. Am. Chem. Soc. 1986, 108, 3005–3015).
  Table 26, Entry 5
  3-(3-[1,3]dioxolan-2-yl-phenyl)-acrylic acid methyl ester. $^1$H NMR (400 MHz, CDCl$_3$): δ 3.80 (s, 3H), 4.03–4.16 (m, 4H), 5.82 (s, 1H), 6.47 (d, J=15.8 Hz, 1H), 7.40 (dd, J=7.7, 7.8 Hz, 1H), 7.49–7.53 (m, 2H), 7.65 (s, 1H), 7.70 (d, J=16.0 Hz, 1H) ppm. $^{13}$C NMR (100 MHz, CDCl$_3$): δ 51.67, 65.29, 103.1, 118.2, 125.9, 128.3, 128.8, 128.9, 134.5, 138.7, 144.4, 167.2. MS: m/z, 233 (M$^+$−1).
  Table 26, Entry 6
  The $^1$H NMR spectroscopic data of 3-phenyl-acrylic acid methyl ester was identical to that of authentic material (Aldrich).

Although the invention has been shown and described with respect to illustrative embodiments thereof, it should be appreciated that the foregoing and various other changes, omissions and additions in the form and detail thereof may be made without departing from the spirit and scope of the invention as delineated in the claims. All patents, patent applications, and literature publications mentioned are herein incorporated by reference in their entireties.

What is claimed is:

1. A transition metal catalyst, comprising:

a Group 8 metal; and a ligand having the structure

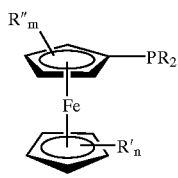

wherein

R, R', and R" are organic groups having 1–15 carbon atoms, n=1–5, and m=0–4.

2. The transition metal catalyst of claim 1, wherein R is t-Bu, R' is phenyl, n=4 or 5, and m=0.

3. The transition metal catalyst of claim 1, wherein R is t-Bu, R' is MeO—$C_6H_4$, n=5, and m=0.

4. The transition metal catalyst of claim 1, wherein R is t-Bu, R' is $F_3C$—$C_6H_4$, n=5, and m=0.

5. The transition metal catalyst of claim 1, wherein R is t-Bu, R' is methyl, n=5, and m=0.

6. The transition metal catalyst of claim 1, wherein R is t-Bu, R" is o-tolyl, n=4, and m=0.

7. A method of forming a compound having an aromatic or vinylic carbon-oxygen, carbon-nitrogen, or carbon-carbon bond, comprising the step of:

reacting a first substrate and a second substrate in the presence of a transition metal catalyst, wherein said first substrate comprises an aryl halide reagent or an aryl sufonate reagent, and said second substrate comprises an alcohol reagent, an alkoxide reagent, a silanol reagent, a siloxide reagent, an amine reagent, an organoboron reagent, an organozinc reagent, an organomagnesium reagent, a malonate reagent, a cyanoacetate reagent, or an olefinic reagent, and wherein said transition metal catalyst comprises a Group 8 metal and a ligand having the structure

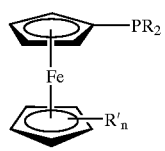

wherein R and R' are organic groups having 1–15 carbon atoms, and n=1–5; under reaction conditions effective to form said compound, wherein said compound has an aromatic carbon-oxygen, carbon-nitrogen, or carbon-carbon bond between said first substrate and said second substrate.

8. The method of claim 7, wherein said first substrate is selected from the group consisting of:

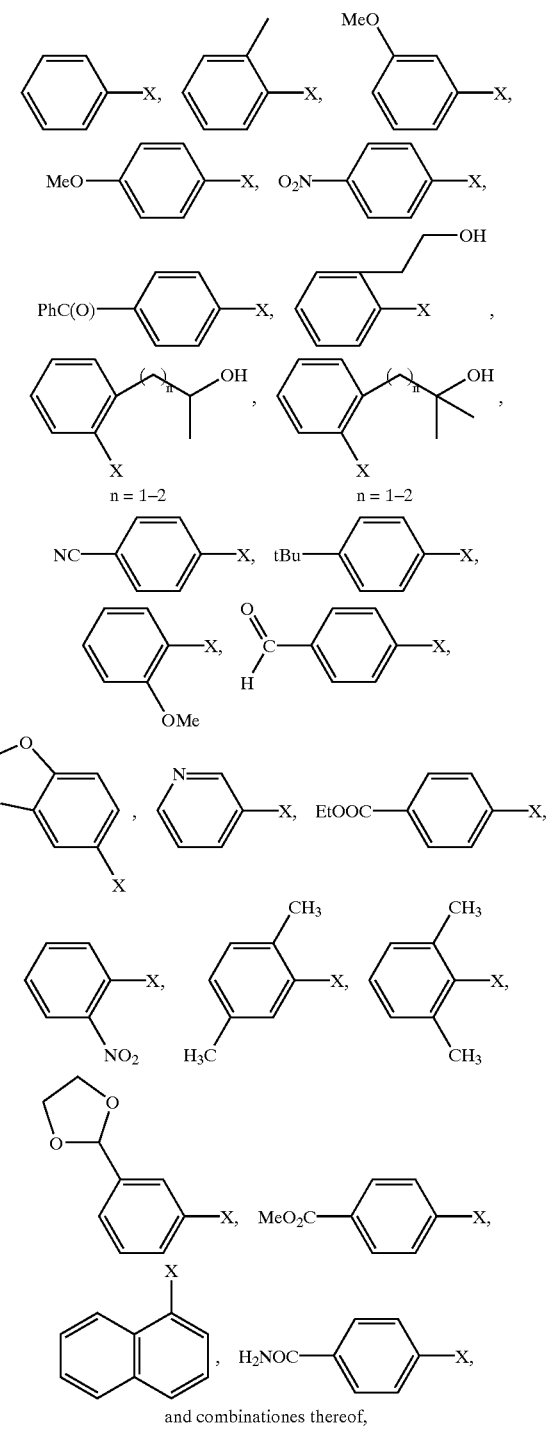

and combinationes thereof, wherein X is selected from the group consisting of bromine, chlorine, fluorine, and iodine.

9. The method of claim 7, wherein said second substrate is selected from the group consisting of NaO—$C_6H_4$—OMe, NaO-tBu, NaO—Si-(tBu)$Me_2$, HO—$C_6H_4$—OMe, HO-tBu, HO—Si-(tBu)$Me_2$, morpholine, dibutylamine, aniline, n-butylamine, n-hexylamine, methylaniline, aminotoluene, organoboronic acid, indole, and combinations thereof.

10. The method of claim 9, wherein said organoboronic acid is selected from the group consisting of o-tolylboronic acid, phenylboronic acid, p-trifluoromethylphenylboronic acid, p-methoxyphenylboronic acid, o-methoxyphenylboronic acid, 4-chlorophenylboronic acid, 4-formylphenylboronic acid, 2-methylphenylboronic acid, 4-methoxyphenylboronic acid, 1-naphthylboronic acid, and combinations thereof.

11. The method of claim 7, wherein said organozinc reagent is selected from the group consisting of n-butylzinc chloride, secbutylzinc chloride, phenylzinc chloride, and combinations thereof.

12. The method of claim 7, wherein said organomagnesium reagent is selected from the group consisting of butylmagnesium bromide, phenylmagnesium chloride, and combinations thereof.

13. The method of claim 7, wherein said malonate reagent is diethyl malonate.

14. The method of claim 7, wherein said cyanoacetate reagent is ethyl cyanoacetate.

15. The method of claim 7, wherein said olefinic reagent is selected from the group consisting of styrene, n-butyl acrylate, methyl acrylate, and combinations thereof.

16. The method of claim 7, wherein said reacting step further takes place in the presence of a base selected from the group consisting of alkali metal hydroxides, alkali metal alkoxides, metal carbonates, alkali metal amides, alkali metal aryl oxides, alkali metal phosphates, tertiary amines, tetraalkylammonium hydroxides, diaza organic bases, and combinations thereof.

17. The method of claim 7, wherein said Group 8 metal is selected from the group consisting of palladium, platinum, nickel, and combinations thereof.

18. The method of claim 7, wherein in said ligand, R is t-Bu, R' is phenyl, and n=4 or 5.

19. The method of claim 7, wherein in said ligand, R is t-Bu, R' is MeO—C₆H₄, and n=5.

20. The method of claim 7, wherein in said ligand, R is t-Bu, R' is F₃C—C₆H₄, and n=5.

21. The method of claim 7, wherein in said ligand, R is t-Bu, R' is methyl, and n=5.

22. The method of claim 7, wherein in said ligand, R is t-Bu, R" is o-tolyl, and n=4.

23. The method of claim 7, wherein said transition metal catalyst is prepared from an alkene or diene complex of said Group 8 transition metal complex combined with said ligand.

24. The method of claim 23, wherein said alkene complex of the Group 8 transition metal is di(benzylidene)acetone.

25. The method of claim 7, wherein said transition metal catalyst is prepared in situ in said reaction.

26. The method of claim 7, wherein said transition metal catalyst is anchored or supported on a support.

27. The method of claim 7, wherein said reaction conditions comprise reaction times from about 30 minutes to about 24 hours, and reaction temperatures from about 22° C. to about 150° C.

28. The method of claim 7, wherein said reaction conditions further comprise a solvent selected from the group consisting of aromatic hydrocarbons, chlorinated aromatic hydrocarbons, ethers, water, aliphatic alcohols, and combinations thereof.

29. A method of forming a compound having an aromatic carbon-oxygen, carbon-nitrogen, or carbon-carbon bond, comprising the step of:

reacting a first substrate and a second substrate in the presence of a transition metal catalyst, wherein said first substrate comprises an aryl halide reagent or an aryl sufonate reagent selected from the group consisting of:

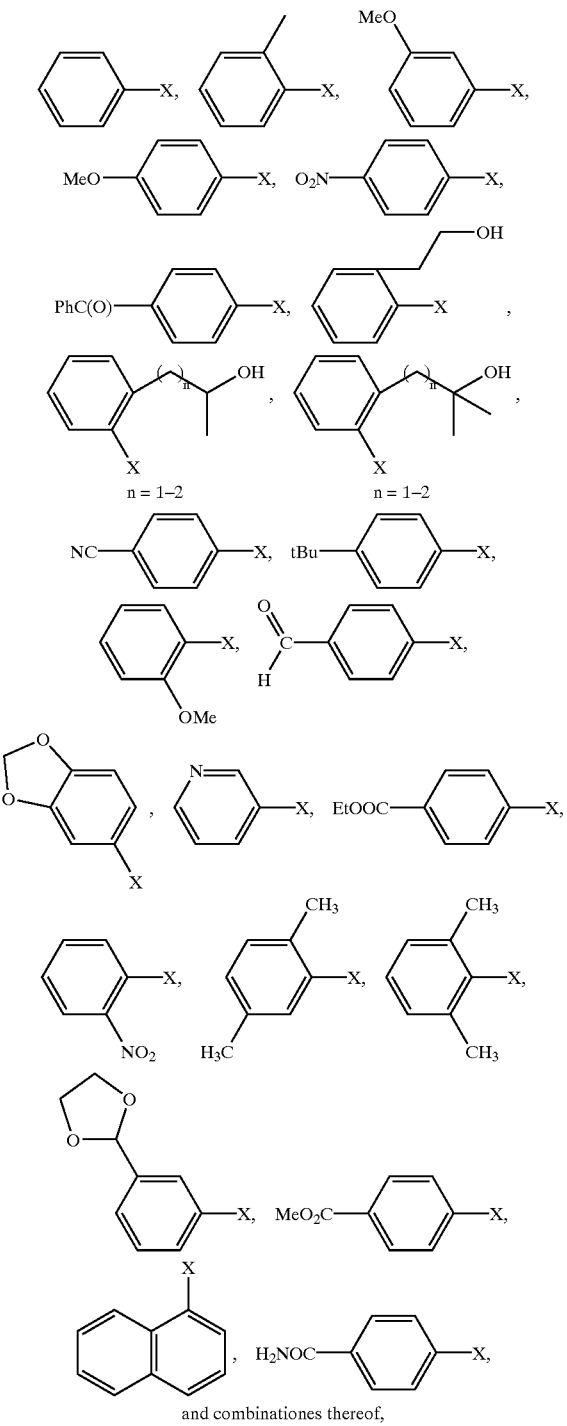

and combinationes thereof, wherein X is selected from the group consisting of bromine, chlorine, fluorine, iodine, and sulfonate; and said second substrate is selected from the group consisting of NaO—C₆H₄—OMe, NaO-tBu, NaO—Si-(tBu)Me₂, HO—C₆H₄—OMe, HO-tBu, HO—Si-(tBu)Me₂, morpholine, dibutylamine, aniline, n-butylamine, n-hexylamine, methylaniline, aminotoluene, organoboron reagents, organozinc reagents, organomagnesium reagents, indoles, ethyl cyanoacetate, diethyl malonate, methyl acrylate, and combinations thereof; and wherein said transition metal catalyst comprises a Group 8 metal selected from the group consisting of palladium, platinum, and nickel, and a ligand having the structure

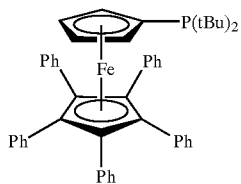

in a solvent selected from the group consisting of aromatic hydrocarbons, chlorinated aromatic hydrocarbons, ethers, water, aliphatic alcohols, and combinations thereof, under reaction conditions effective to form said compound, wherein said compound has an aromatic carbon-oxygen, carbon-nitrogen, or carbon-carbon bond between said first substrate and said second substrate.

30. The method of claim 29, wherein said organoboron reagent is an organoboronic acid selected from the group consisting of o-tolylboronic acid, phenylboronic acid, p-trifluoromethylphenylboronic acid, p-methoxyphenylboronic acid, o-methoxyphenylboronic acid, 4-chlorophenylboronic acid, 4-formylphenylboronic acid, 2-methylphenylboronic acid, 4-methoxyphenylboronic acid, 1-naphthylboronic acid, and combinations thereof.

31. The method of claim 29, wherein said organozinc reagent is selected from the group consisting of n-butylzinc chloride, secbutylzinc chloride, phenylzinc chloride, and combinations thereof.

32. The method of claim 29, wherein said organomagnesium reagent is selected from the group consisting of butylmagnesium bromide, phenylmagnesium chloride, and combinations thereof.

33. The method of claim 29, wherein said transition metal catalyst is prepared from an alkene or diene complex of said Group 8 transition metal complex combined with said ligand.

34. The method of claim 33, wherein said alkene complex of the Group 8 transition metal is di(benzylidene)acetone.

35. The method of claim 29, wherein said reacting step further takes place in the presence of a base selected from the group consisting of alkali metal hydroxides, alkali metal alkoxides, metal carbonates, alkali metal amides, alkali metal aryl oxides, alkali metal phosphates, tertiary amines, tetraalkylammonium hydroxides, diaza organic bases, and combinations thereof.

36. The method of claim 29, wherein said transition metal catalyst is prepared in situ in said reaction.

37. The method of claim 29, wherein said transition metal catalyst is anchored or supported on a support.

38. The method of claim 29, wherein said reaction conditions comprise reaction times from about 30 minutes to about 24 hours, and reaction temperatures from about 22° C. to about 150° C.

* * * * *